(12) United States Patent
Johnson et al.

(10) Patent No.: US 9,187,406 B2
(45) Date of Patent: Nov. 17, 2015

(54) CURCUMIN ANALOGUES AS ZINC CHELATORS AND THEIR USES

(75) Inventors: Francis Johnson, Setautek, NY (US); Lorne Golub, Smithtown, NY (US)

(73) Assignees: The Research Foundation of State University of New York, Albany, NY (US); Chem-Master International, Inc., East Setautek, NY (US)

( * ) Notice: Subject to any disclaimer, the term of this patent is extended or adjusted under 35 U.S.C. 154(b) by 974 days.

(21) Appl. No.: 13/319,478

(22) PCT Filed: May 14, 2010

(86) PCT No.: PCT/US2010/034971
§ 371 (c)(1),
(2), (4) Date: Dec. 7, 2011

(87) PCT Pub. No.: WO2010/132815
PCT Pub. Date: Nov. 18, 2010

(65) Prior Publication Data
US 2012/0095051 A1   Apr. 19, 2012

Related U.S. Application Data

(60) Provisional application No. 61/216,392, filed on May 15, 2009.

(51) Int. Cl.
| | | |
|---|---|---|
| C07D 213/50 | (2006.01) | |
| C07C 225/22 | (2006.01) | |
| C07C 49/255 | (2006.01) | |
| C07C 69/738 | (2006.01) | |
| C07C 235/78 | (2006.01) | |
| C07C 237/20 | (2006.01) | |

(52) U.S. Cl.
CPC .............. *C07C 225/22* (2013.01); *C07C 49/255* (2013.01); *C07C 69/738* (2013.01); *C07C 235/78* (2013.01); *C07C 237/20* (2013.01); *C07D 213/50* (2013.01)

(58) Field of Classification Search
CPC .. C07C 225/22; C07C 49/255; C07C 69/738; C07C 235/78; C07C 237/20; C07D 213/50
See application file for complete search history.

(56) References Cited

U.S. PATENT DOCUMENTS

| | | | |
|---|---|---|---|
| 8,236,852 | B2 | 8/2012 | Shih et al. |
| 2001/0051184 | A1 | 12/2001 | Heng |
| 2004/0253329 | A1 | 12/2004 | Mae et al. |
| 2005/0267221 | A1 | 12/2005 | Wellem |
| 2006/0258752 | A1 | 11/2006 | Vander Jagt et al. |
| 2006/0276536 | A1 | 12/2006 | Vander Jagt et al. |
| 2007/0060644 | A1 | 3/2007 | Vander Jagt et al. |
| 2008/0161391 | A1 | 7/2008 | Lee et al. |
| 2008/0200478 | A1 | 8/2008 | Robinson |
| 2010/0010232 | A1 | 1/2010 | Neupert et al. |
| 2010/0152493 | A1 | 6/2010 | Shibata et al. |
| 2011/0044895 | A1 | 2/2011 | Berry et al. |
| 2011/0152382 | A1 | 6/2011 | Heng |
| 2012/0095051 | A1 | 4/2012 | Johnson et al. |
| 2015/0073021 | A1 | 3/2015 | Antonelli et al. |

FOREIGN PATENT DOCUMENTS

| | | |
|---|---|---|
| DE | 25 01 220 A1 | 7/1976 |
| JP | 2008-137914 A | 6/2008 |
| WO | WO 00/70949 A1 | 11/2000 |
| WO | WO 03/088927 A2 | 10/2003 |
| WO | WO 2008/045534 A2 | 4/2008 |
| WO | WO 2008/048410 A2 | 4/2008 |
| WO | WO 2008/085984 A1 | 7/2008 |
| WO | WO 2010/121007 A1 | 10/2010 |
| WO | WO 2010/132815 A1 | 12/2010 |
| WO | WO 2011/142795 A9 | 11/2011 |
| WO | WO 2013/059203 A1 | 4/2013 |
| WO | WO 2014/005089 A2 | 1/2014 |

OTHER PUBLICATIONS

Written Opinion of the International Search Authority issued Jul. 12, 2010 in connection with International Application No. PCT/2010/034971.

International Preliminary Report on Patentability Chapter I issued Nov. 15, 2011 in connection with International Application No. PCT/2010/034971.

Extended European Search Report issued Oct. 18, 2012 in connection with European Application No. EP 10775624.9.

Communication Pursuant to Rules 70(2) and 70a(2) EPC issued Nov. 6, 2012 by the European Patent Office in connection with European Application No. EP 10775624.9.

Amendment in Response to Nov. 6, 2012 Communication Pursuant to Rules 70(2) and 70a(2) EPC filed May 6, 2013 in connection with European Application No. EP 10775624.9.

International Search Report issued Jan. 17, 2013 in connection with International Application No. PCT/US2012/060437.

(Continued)

*Primary Examiner* — Samantha Shterengarts
(74) *Attorney, Agent, or Firm* — Gary J. Gershik; Cooper & Dunham LLP

(57) ABSTRACT

This invention provides a compound having the structure

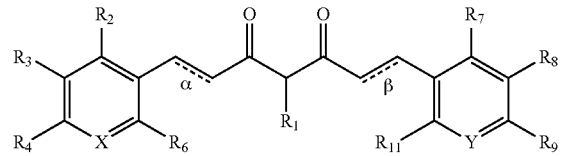

wherein α, β, X, Y, and $R_1$-$R_{11}$ are defined herein. This invention also provides a pharmaceutical composition comprising the above compounds, a method of inhibiting the activity and/or levels of a matrix metalloproteinase (MMP), a method of inhibiting the production of a cytokine in a population of cells, a method of inhibiting the production of a growth factor in a population of cells, and a method of inhibiting NFκ-B activation in a population of cells.

14 Claims, 25 Drawing Sheets

(56) References Cited

OTHER PUBLICATIONS

Pill-Hoon Bong (1999) "Spectral and photophysical behaviours of curcumin and curcuminoids." Bull. Korean Chem. Soc., vol. 21, No. 1, pp. 81-86.

Jankun et al. (2006) "Synthetic curcuminoids modulate the arachidonic acid metabolism of human platelet 12-lipoxygenase and reduce sprout formation of human endothelial cells", Molecular Cancer Therapeutics, vol. 5, No. 5, pp. 1371-1382.

Matthes et al. (1980) "Cytotoxic components of Zingiber Zerumbet, Curcuma Zedoaria and C. Domestica", Phytochemistry, vol. 19, pp. 2643-2650.

Shao et al. (2006) "Facile preparation of new unsymmetrical curcuma derivatives by solid-phase synthesis strategy" Tetrahedron Letters, vol. 47, No. 24, pp. 4085-4089.

Weber et al. (2006) "Activation of NFkappaB is inhibited by curcumin and related enones" Bioorganic & Medicinal Chemistry, vol. 14, No. 7, pp. 2450-2461.

Zhang et al. (2008) "Synthesis and cytotoxic activity of novel curcumin analogues" Chinese Chemical Letters, vol. 19, No. 3, pp. 281-285.

Written Opinion of the International Search Authority issued Jan. 17, 2013 in connection with International Application No. PCT/US2012/060437.

International Preliminary Report on Patentability Chapter I issued Apr. 22, 2014 in connection with International Application No. PCT/US2012/060437.

Extended European Search Report ssued Feb. 3, 2015 in connection with European application No. 12841310.1.

International Search Report issued Feb. 14, 2014 in connection with International Application No. PCT/US2013/048710.

Written Opinion of the International Search Authority issued Feb. 14, 2014 in connection with International Application No. PCT/US2013/048710.

International Preliminary Report on Patentability Chapter I issued Feb. 14, 2014 in connection with International Application No. PCT/US2013/048710.

Office Action issued Mar. 12, 2015 in connection with U.S Appl. No. 14/352,277.

International Search Report issued by the International Searching Authority (ISA/O.E.P.M.) on Jul. 12, 2010 in connection with International Application No. PCT/US2010/034971.

Curcumin

Tetrahydrocurcumin

**1,10-o-phenanthroline
(4,5-diazaphenanthrene)**

A.

92kDa →
72kDa →
62kDa →

NDC   UD   D + Cpd 1 (100 mg/kg)   D + Cpd 1 (500 mg/kg)

B.

CURCUMIN ANALOGUES AS ZINC CHELATORS AND THEIR USES

This application is a §371 National Stage of PCT International Application No. PCT/US2010/034971, filed May 14, 2010, claiming priority of Provisional Application No. 61/216,392, filed May 15, 2009, the contents of which are hereby incorporated by reference into this application.

This application claims the benefit of U.S. Provisional Application No. 61/216,392, filed May 15, 2009, the content of which is hereby incorporated by reference in its entirety.

Throughout this application, certain publications are referenced in parentheses. Full citations for these publications may be found immediately preceding the claims. The disclosures of these publications in their entireties are hereby incorporated by reference into this application in order to describe more fully the state of the art to which this invention relates.

BACKGROUND OF THE INVENTION

For decades, soon after the first of the matrix metalloproteinases (MMPs), known as collagenase-1 or MMP-1, was discovered in the early 1960s (1), academics and industry have been trying to develop safe and effective pharmaceuticals to inhibit these calcium- and zinc-dependent neutral proteinases which are expressed and activated in excessive levels during a variety of diseases (see (2) and (3) for reviews). The rationale for this drug development strategy lies in the fact that collagen and the other connective tissue constituents: (a) are collaboratively degraded by these MMPs (now numbering more than 25 genetically distinct types, "22 found in the human genome" (2)); and (b) are found virtually everywhere in the body (e.g., skin, bone, tendons and ligaments, cornea of the eye, cartilage of the joints), and the excessive destruction of these constituents is a key event in the pathogenesis of numerous diseases ranging from inflammatory conditions (e.g., rheumatoid arthritis, atherosclerosis, periodontitis), to metabolic bone diseases (e.g., postmenopausal osteoporosis, diabetes-induced osteopenia), to cancer invasion, metastasis and angiogenesis (2, 4).

Matrix metalloproteinases (MMPs) are a collective of over thirty zinc-containing endopeptidases that include the gelatinases, stromelysins, and collagenases, released as inactive zymogens and becoming active only when the propeptide is cleaved (5). The gelatinases include MMP-2 and MMP-9, and the stromelysins include MMP-3, -7, 10, and -11. The collagenases include MMP-1, -8, and -13 (5). The MMPs, when constitutively expressed or induced by pro-inflammatory agents, such as cytokines, hormones, bacterial products, endotoxins, among others, can degrade all components of the extracellular matrix (5). Under physiological conditions, MMPs are regulated by endogenous inhibitors, particularly the tissue inhibitors of metalloproteinases (TIMPs) (5, 6a).

Aberrant MMP activity and expression has been implicated in a number of pathological conditions, including rheumatoid arthritis (RA), osteoarthritis (OA), metastases, periodontal disease, angiogenesis, emphysema, multiple sclerosis (5), and cardiovascular disease, such as atherosclerosis, myocardial infarction, arterial restenosis after angioplasty and aneurysm development (6a). Recent research has also implicated MMPs in asthma attacks, chronic obstructive pulmonary disease, and premature skin aging (6a) and inflammatory skin disease (6b, 6c). Their involvement in the epidermal growth factor-receptor activation pathway leading to cardiac hypertrophy has also been reported (6a). It is believed that an imbalance between the active enzymes and their natural inhibitors leads to the accelerated destruction of connective tissue and the potential for using specific enzyme inhibitors as therapeutic agents to redress this balance has led to intensive research focused on the design, synthesis and molecular deciphering of low-molecular-mass inhibitors of this family of proteins (7).

At least 56 MMP inhibitors have been pursued as clinical candidates since the late 1970's, and as of 2006, only 1 inhibitor, a sub-antimicrobial (low-dose) doxycycline formulation (Periostat® for periodontal disease), has been approved (8). Early clinical studies with other known MMP inhibitors, in particular a series of hydroxamic acids, have revealed a severe adverse side-effect frequently referred to as the musculoskeletal syndrome (MSS), which is a tendonitis-like fibromyalgia (8). In subsequent MMP inhibitor clinical trials, efforts to avoid MSS coupled with an inability to assess the therapeutic index (ie., the ratio between the dose required for efficacy vs. toxicology), may have resulted in dose selection beneath the minimal effective dose, hampering MMP inhibitor development (8).

Therefore, there is a need for the development of new MMP inhibitors.

Curcumin (diferuloylmethane, FIG. 1), the major component in curcuma/turmeric, is an antioxidant polyphenol from the plant *Curcuma longa* and is commonly used as a spice component. Curcumin has been used to treat inflammation and exerts antiproliferative and proapoptotic effects against various tumors in vitro and in vivo, and it has been found to suppress carcinogenesis of the breast and other organs (9, 10). Bachmeier and coworkers have reported downregulation of the inflammatory cytokines CXCL1 and CXCL2 in breast cancer cells via NFκB (9). Oral curcumin efficacy in vivo has been shown in models for many conditions with oxidative damage and inflammation, including many types of cancer, diabetes, atherosclerosis, arthritis, stroke, peripheral neuropathy, inflammatory bowel disease, and brain trauma (11). Curcumin, along with its tetrahydro derivative, tetrahydrocurcumin (THC, FIG. 1.), has been shown to inhibit IL-1β in an acute brain inflammation model while curcumin was more effective than THC in attenuating plaque pathogenesis in studies of curcumin efficacy in models of neuroinflammation, which is implicated in the pathogenesis of many neurodegenerative disorders, including Alzheimer's disease (AD) (11).

Curcumin has also been shown to inhibit MMPs. Curcumin (at 15 μM concentration) has been observed to exert a significant inhibitory effect on MMP-2 activity which was not reversible even after cells were grown for 28 days without curcumin (12). It is known that highly metastatic cells become less aggressive when MMP-2 expression or activity is reduced and previous studies have also shown that curcumin reduces MMP-2 expression in breast carcinoma cell lines (12). This reduction of MMP-2 activity could be an important reason for anti-metastatic property of curcumin (12). In addition, curcumin has also been shown to inhibit MMP-9 expression in human astroglioma cells (13). Analogues and derivatives of curcumin have previously been described for use against various cancers (14, 15, 16, 17) as well as pancreatitis (18).

While curcumin has been shown to have multiple beneficial effects, poor oral absorption of curcumin in both humans and animals has raised several concerns that this may limit its clinical impact (11).

Herein, novel chemically-modified curcumins as inhibitors of matrix metalloproteinases and pro-inflammatory cytokine production are disclosed.

SUMMARY OF THE INVENTION

This invention provides a compound having the structure

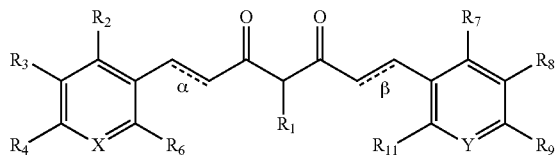

wherein
bond α and β are each, independently, present or absent;
X is $CR_5$ or N; Y is $CR_{10}$ or N;
$R_1$ is H, $CF_3$, halogen, $-NO_2$, $-OCF_3$, $-OR_{12}$, $-NHCOR_{12}$, $-SR_{12}$, $-SO_2R_{13}$, $-COR_{14}$, $-CSR_{14}$, $-CNR_{14}$, $-C(=NR_{12})R_{14}$, $-C(=NH)R_{14}$, $-SOR_{12}$, $-POR_{12}$, $-P(=O)(OR_{12})(OR_{13})$, or $-P(OR_{12})(OR_{13})$,
wherein $R_{12}$ and $R_{13}$ are each, independently, H, $C_{1-10}$ alkyl, $C_{2-10}$ alkenyl, $C_{2-10}$ alkynyl, aryl, heteroaryl, or heterocyclyl;
$R_{14}$ is $C_{2-10}$ alkyl, $C_{2-10}$ alkenyl, $C_{2-10}$ alkynyl, heteroaryl, heterocyclyl, methoxy, $-OR_{15}$, $-NR_{16}R_{17}$, or

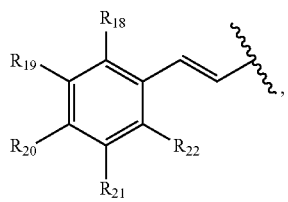

wherein $R_{15}$ is H, $C_{3-10}$ alkyl, $C_{2-10}$ alkenyl, $C_{2-10}$ alkynyl;
$R_{16}$ and $R_{17}$ are each, independently, H, alkyl, $C_{2-10}$ alkenyl, $C_{2-10}$ alkynyl, aryl, heteroaryl, or heterocyclyl;
$R_{18}$, $R_{19}$, $R_{21}$, and $R_{22}$ are each independently H, halogen, $-NO_2$, $-CN$, $-NR_{23}R_{24}$, $-SR_{23}$, $-SO_2R_{23}$, $-CO_2R_{23}$, $-OR_{25}$, $CF_3$, $-SOR_{23}$, $-POR_{23}$, $-C(=S)R_{23}$, $-C(=NH)R_{23}$, $-C(=NR_{24})R_{23}$, $-C(=N)R_{23}$, $-P(=O)(OR_{23})(OR_{24})$, $-P(OR_{23})(OR_{24})$, $-C(=S)R_{23}$, $C_{1-10}$ alkyl, $C_{2-10}$ alkenyl, $C_{2-10}$ alkynyl, aryl, heteroaryl, or heterocyclyl;
wherein $R_{23}$, $R_{20}$, and $R_{25}$ are each, independently, H, $C_{1-10}$ alkyl, $C_{2-10}$ alkenyl, $C_{2-10}$ alkynyl, aryl, heteroaryl, or heterocyclyl;
$R_{20}$ is halogen, $-NO_2$, $-CN$, $-NR_{26}R_{27}$, $CF_3$, $C_{1-10}$ alkyl, $C_{2-10}$ alkenyl, $C_{2-10}$ alkynyl, aryl, heteroaryl, or heterocyclyl;

wherein $R_{26}$ and $R_{27}$ are each, independently, H, $C_{1-10}$ alkyl, $C_{2-10}$ alkenyl, $C_{2-10}$ alkynyl, aryl, heteroaryl, or heterocyclyl;
$R_2$, $R_3$, $R_3$, $R_5$, $R_6$, $R_7$, $R_8$, $R_9$, $R_{10}$, and $R_{11}$ are each independently, H, halogen, $-NO_2$, $-CN$, $-NR_{28}R_{29}$, $-NHR_{28}R_{29}^+$, $-SR_{29}$, $-SO_2R_{28}$, $-OR_{28}$, $-CO_2R_{28}$, $CF_3$, $C_{1-10}$ alkyl, $C_{2-10}$ alkenyl, $C_{2-10}$ alkynyl, aryl, heteroaryl, or heterocyclyl;
wherein $R_{28}$ and $R_{29}$ are each, H, $CF_3$, $C_{1-10}$ alkyl, $C_{2-10}$ alkenyl, $C_{2-10}$ alkynyl, or $-C(=O)$-heterocyclyl; and
wherein when $R_1$ is H, $R_3$, $R_4$, $R_5$, $R_8$, $R_9$, or $R_{10}$, is halogen, $-NO_2$, $-CN$, $-NR_{28}R_{29}$, $-NHR_{28}R_{29}^+$, $-SR_{28}$, $-SO_2R_{28}$, $-CO_2R_{28}$, $CF_3$, $C_{1-10}$ alkyl, $C_{2-10}$ alkenyl, $C_{2-10}$ alkynyl, aryl, heteroaryl, or heterocyclyl;
wherein $R_{28}$ and $R_{29}$ are each, H, $CF_3$, $C_{1-10}$ alkyl, $C_{2-10}$ alkenyl, $C_{2-10}$ alkynyl, or $-C(=O)$-heterocyclyl; and
wherein each occurrence of alkyl, alkenyl, or alkynyl is branched or unbranched, unsubstituted or substituted;
or a salt thereof.

This invention provides a pharmaceutical composition comprising a pharmaceutically acceptable carrier and of the above compounds.

This invention also provides a method of inhibiting the activity and/or levels of a matrix metalloproteinase (MMP) comprising contacting the matrix metalloproteinase or a cell producing an MMP or MMPs with any one of the above compounds so as to inhibit the activity of a matrix metalloproteinase.

This invention further provides a method of inhibiting the production of a cytokine in a population of mammalian cells comprising contacting the population of cells with any one of the above compounds so as to inhibit production of a cytokine.

This invention yet further provides a method of inhibiting the production of a growth factor in a population of mammalian cells comprising contacting the population of cells with the any one of the above compounds so as to inhibit production of a growth factor.

This invention provides a method of inhibiting NFκ-B activation in a population of cells comprising contacting the population of cells with any one of the above compounds so as to inhibit NFκ-B activation.

This invention provides a method of increasing water solubility, metal binding ability, MMP inhibition activity, cytokine inhibition activity, growth factor inhibition activity, or NFκB activation inhibition activity of curcumin comprising synthesizing a compound having the structure

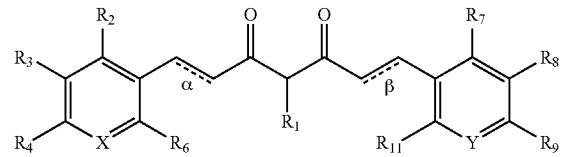

wherein
bond α and β are each, independently, present or absent;
X is $CR_5$ or N; Y is $CR_{10}$ or N;
$R_1$ is H or an electron-withdrawing group;
$R_2$, $R_3$, $R_4$, $R_5$, $R_6$, $R_7$, $R_8$, $R_9$, $R_{10}$, and $R_{11}$ are each independently, H, halogen, $-NO_2$, $-CN$, $-NR_{28}R_{29}$, $-NHR_{29}R_{29}^+$, $-SR_{28}$, $-SO_2R_{28}$, $-OR_{28}$, $-CO_2R_{28}$, $CF_3$, $C_{1-10}$ alkyl, $C_{2-10}$ alkenyl, $C_{2-10}$ alkynyl, aryl, heteroaryl, or heterocyclyl;

wherein $R_{28}$ and $R_{29}$ are each, H, $CF_3$, $C_{1-10}$ alkyl, $C_{2-10}$ alkenyl, $C_{2-10}$ alkynyl, or —C(=O)-heterocyclyl; and wherein when $R_1$ is H, $R_3$, $R_4$, $R_5$, $R_8$, $R_9$, or $R_{10}$, is halogen, —$NO_2$, —CN, —$NR_{28}R_{29}$, —$NHR_{28}R_{29}^+$, —$SR_{28}$, —$SO_2R_{28}$, —$CO_2R_{28}$, $CF_3$, $C_{1-10}$ alkyl, $C_{2-10}$ alkenyl, $C_{2-10}$ alkynyl, aryl, heteroaryl, or heterocyclyl;

wherein $R_{28}$ and $R_{29}$ are each, H, $CF_3$, $C_{1-10}$ alkyl, $C_{2-10}$ alkenyl, $C_{2-10}$ alkynyl, or —C(=O)-heterocyclyl; and wherein each occurrence of alkyl, alkenyl, or alkynyl is branched or unbranched, unsubstituted or substituted;

or a salt thereof.

DETAILED DESCRIPTION OF THE INVENTION

Figure 1:
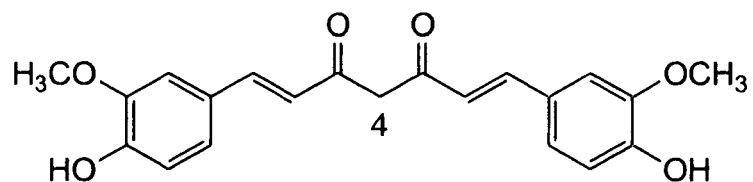
FIG. 1. Chemical structures of curcumin, tetrahydrocurcumin (THC), and 1,10-O-phenanthroline.
Figure 1:
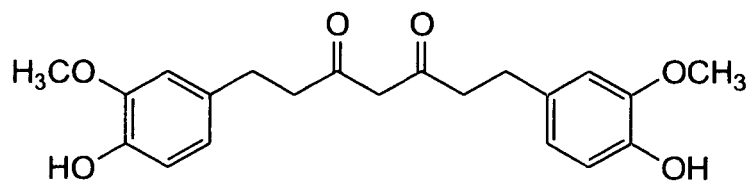
Figure 1:
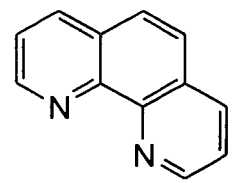

This invention provides a compound having the structure

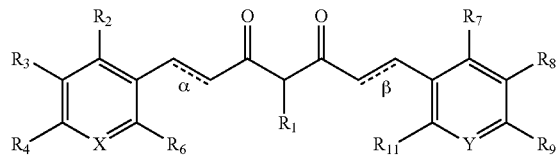

wherein
bond α and β are each, independently, present or absent;
X is $CR_5$ or N; Y is $CR_{10}$ or N;
$R_1$ is H, $CF_3$, halogen, —$NO_2$, —$OCF_3$, —$OR_{12}$, —NH-$COR_{12}$, —$SR_{12}$, —$SO_2R_{13}$, —$CSR_{14}$, —$CNR_{14}$, —C(=$NR_{12}$)$R_{14}$, —C(=NH)$R_{14}$, —$SOR_{12}$, —$POR_{12}$, —P(=O)($OR_{12}$)($OR_{13}$), or —P($OR_{12}$)($OR_{13}$), wherein $R_{12}$ and $R_{13}$ are each, independently, H, $C_{1-10}$ alkyl, $C_{2-10}$ alkenyl, $C_{2-10}$ alkynyl, aryl, heteroaryl, or heterocyclyl;

$R_{14}$ is $C_{2-10}$ alkyl, $C_{2-10}$ alkenyl, $C_{2-10}$ alkynyl, heteroaryl, heterocyclyl, methoxy, —$OR_{15}$, —$NR_{16}R_{17}$, or

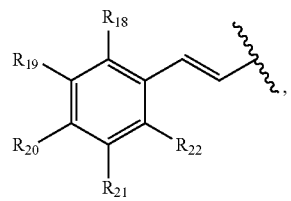

wherein $R_{15}$ is H, $C_{3-10}$ alkyl, $C_{2-10}$ alkenyl, $C_{2-10}$ alkynyl;

$R_{16}$ and $R_{17}$ are each, independently, H, $C_{1-10}$ alkyl, $C_{2-10}$ alkenyl, $C_{2-10}$ alkynyl, aryl, heteroaryl, or heterocyclyl;

$R_{18}$, $R_{19}$, $R_{21}$, and $R_{22}$ are each independently H, halogen, —$NO_2$, —CN, —$NR_{23}R_{24}$, —$SR_{23}$, —$SO_2R_{23}$, —$CO_2R_{23}$, —$OR_{25}$, $CF_3$, —$SOR_{23}$, —$POR_{23}$, —C(=S)$R_{23}$, —C(=NH)$R_{23}$, —C(=$NR_{24}$)$R_{23}$, —P(=O)($OR_{23}$)($OR_{24}$), —P($OR_{23}$)($OR_{24}$), —C(=S)$R_{23}$, $C_{1-10}$ alkyl, $C_{2-10}$ alkenyl, $C_{2-10}$ alkynyl, aryl, heteroaryl, or heterocyclyl;

wherein $R_{23}$, $R_{24}$, and $R_{25}$ are each, independently, H, $C_{1-10}$ alkyl, $C_{2-10}$ alkenyl, $C_{2-10}$ alkynyl, aryl, heteroaryl, or heterocyclyl;

$R_{20}$ is halogen, —$NO_2$, —CN, —$NR_{26}R_{27}$, $CF_3$, $C_{1-10}$ alkyl, $C_{2-10}$ alkenyl, $C_{2-10}$ alkynyl, aryl, heteroaryl, or heterocyclyl;

wherein $R_{26}$ and $R_{27}$ are each, independently, H, $C_{1-10}$ alkyl, $C_{2-10}$ alkenyl, $C_{2-10}$ alkynyl, aryl, heteroaryl, or heterocyclyl;

$R_2$, $R_3$, $R_4$, $R_5$, $R_6$, $R_7$, $R_8$, $R_9$, $R_{10}$, and $R_{11}$ are each independently, H, halogen, —$NO_2$, —CN, —$NR_{28}R_{29}$, —$NHR_{28}R_{29}^+$, —$SR_{28}$, —$SO_2R_{28}$, —$OR_{28}$, —$CO_2R_{28}$, $CF_3$, $C_{1-10}$ alkyl, $C_{2-10}$ alkenyl, $C_{2-10}$ alkynyl, aryl, heteroaryl, or heterocyclyl;

wherein $R_{28}$ and $R_{29}$ are each, H, $CF_3$, $C_{1-10}$ alkyl, $C_{2-10}$ alkenyl, $C_{2-10}$ alkynyl, or —C(=O)-heterocyclyl; and wherein when $R_1$ is H, $R_3$, $R_4$, $R_5$, $R_8$, $R_9$, or $R_{10}$, is halogen, —$NO_2$, —CN, —$NR_{28}R_{29}$, —$NHR_{28}R_{29}^+$, —$SR_{28}$, —$SO_2R_{28}$, —$CO_2R_{28}$, $CF_3$, $C_{1-10}$ alkyl, $C_{2-10}$ alkenyl, $C_{2-10}$ alkynyl, aryl, heteroaryl, or heterocyclyl;

wherein $R_{28}$ and $R_{29}$ are each, H, $CF_3$, $C_{1-10}$ alkyl, $C_{2-10}$ alkenyl, $C_{2-10}$ alkynyl, or —C(=O)-heterocyclyl; and wherein each occurrence of alkyl, alkenyl, or alkynyl is branched or unbranched, unsubstituted or substituted;

or a salt thereof.

In an embodiment, when $R_1$ is H, $R_3$, $R_4$, $R_5$, $R_8$, $R_9$, or $R_{10}$, is —$NO_2$, —$NR_{28}R_{29}$, —$NHR_{28}R_{29}^+$, —$SR_{28}$, —$SR_{28}$, —$SO_2R_{28}$, —$CO_2R_{28}$, $CF_3$, $C_{1-10}$ alkyl, $C_{2-10}$ alkenyl, $C_{2-10}$ alkynyl; or a salt thereof.

In another embodiment, when $R_1$ is H, $R_4$ or $R_9$ is —$NO_2$, —$NR_{28}R_{29}$, —$NHR_{28}R_{29}^+$; or a salt thereof.

In yet another embodiment, when $R_1$ is H, $R_4$ or $R_9$ is —$NR_{28}R_{29}$ or —$NHR_{28}R_{29}^+$; or a salt thereof.

In an embodiment, $R_1$ is H or —$COR_{14}$, wherein $R_{14}$ is methoxy or —NH-phenyl;

$R_2$, $R_5$, $R_6$, $R_7$, $R_{10}$ and $R_{14}$ are each H;

$R_3$, $R_4$, $R_8$, and $R_9$ are each, independently H, —OH, —$OCH_3$, —$N(CH_3)_2$ or —$NH(CH_3)_2$;

or a salt thereof.

In an embodiment, the compound has the structure

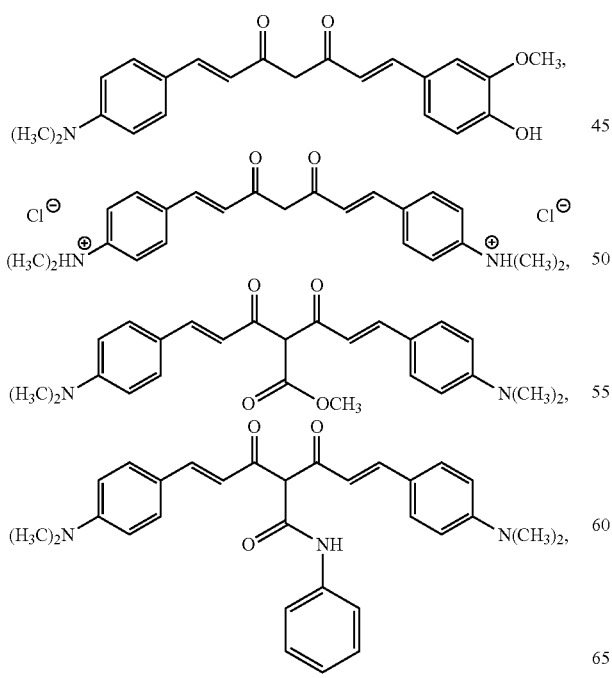

or a salt thereof.

In an embodiment, the compound has the structure

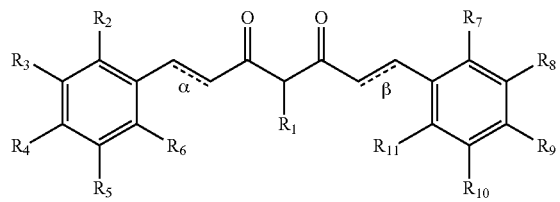

where bond α and β are each, independently, present or absent;

$R_1$ is $CF_3$, halogen, —$NO_2$, —$OCF_3$, —$OR_{12}$, —NH-$COR_{12}$, —$SR_{12}$, —$SO_2R_{13}$, —$COR_{14}$, —$CSR_{14}$, or —$CNR_{14}$, wherein $R_{12}$ and $R_{13}$ are each, independently, H, $C_{1-10}$ alkyl, $C_{2-10}$ alkenyl, $C_{2-10}$ alkynyl, aryl, heteroaryl, or heterocyclyl;

$R_{14}$ is $C_{2-10}$ alkyl, $C_{2-10}$ alkenyl, $C_{2-10}$ alkynyl, heteroaryl, heterocyclyl, methoxy, —$OR_{15}$, —$NR_{16}R_{17}$, or

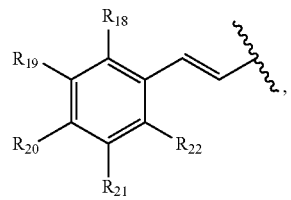

wherein $R_{15}$ is H, $C_{3-10}$ alkyl, $C_{2-10}$ alkenyl, $C_{2-10}$ alkynyl;

$R_{16}$ and $R_{17}$ are each, independently, H, $C_{1-10}$ alkyl, $C_{2-10}$ alkenyl, $C_{2-10}$ alkynyl, aryl, heteroaryl, or heterocyclyl;

$R_{18}$, $R_{19}$, $R_{21}$, and $R_{22}$ are each independently H, halogen, —$NO_2$, —CN, —$NR_{23}R_{24}$, —$SR_{23}$, —$SO_2R_{23}$, —$CO_2R_{23}$, —$OR_{25}$, $CF_3$, $C_{1-10}$ alkyl, $C_{2-10}$ alkenyl, $C_{2-10}$ alkynyl, aryl, heteroaryl, or heterocyclyl;

wherein $R_{23}$, $R_{24}$, and $R_{25}$ are each, independently, H, $C_{1-10}$ alkyl, $C_{2-10}$ alkenyl, $C_{2-10}$ alkynyl, aryl, heteroaryl, or heterocyclyl;

$R_{20}$ is halogen, —$NO_2$, —CN, —$NR_{26}R_{27}$, $CF_3$, $C_{1-10}$ alkyl, $C_{2-10}$ alkenyl, $C_{2-10}$ alkynyl, aryl, heteroaryl, or heterocyclyl;

wherein $R_{26}$ and $R_{27}$ are each, independently, H, $C_{1-10}$ alkyl, $C_{2-10}$ alkenyl, $C_{2-10}$ alkynyl, aryl, heteroaryl, or heterocyclyl;

$R_2$, $R_3$, $R_4$, $R_5$, $R_6$, $R_7$, $R_8$, $R_9$, $R_{10}$, and $R_{11}$ are each independently, H, halogen, —$NO_2$, —CN, —$NR_{28}R_{29}$, —$SR_{28}$, —$SO_2R_{28}$, —$OR_{28}$, —$CO_2R_{28}$, $CF_3$, $C_{1-10}$ alkyl, $C_{2-10}$ alkenyl, $C_{2-10}$ alkynyl, aryl, heteroaryl, or heterocyclyl;

wherein $R_{28}$ and $R_{29}$ are each, H, $CF_3$, $C_{1-10}$ alkyl, $C_{2-10}$ alkenyl, or $C_{2-10}$ alkynyl; and wherein each occurrence of alkyl, alkenyl, or alkynyl is branched or unbranched, unsubstituted or substituted; and wherein at least one of $R_2$, $R_3$, $R_4$, $R_5$, and $R_6$ and at least one of $R_7$, $R_8$, $R_9$, $R_{10}$, and $R_{11}$, are each, independently, —$OR_{28}$;

or a salt thereof.

In an embodiment, the compound has the structure

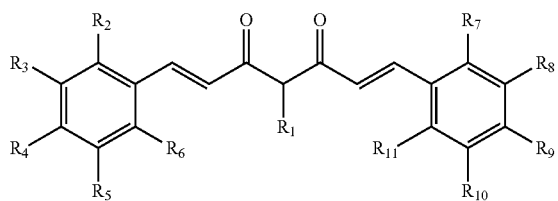

wherein $R_1$ is $CF_3$, halogen, $-NO_2$, $-OCF_3$, $-OR_{12}$, $-NHCOR_{12}$, $-SR_{12}$, $-SO_2R_{13}$, $-COR_{14}$, $-CSR_{14}$, or $-CNR_{14}$, wherein $R_{12}$ and $R_{13}$ are each, independently, H, $C_{1-10}$ alkyl, $C_{2-10}$ alkenyl, $C_{2-10}$ alkynyl, aryl, heteroaryl, or heterocyclyl;

$R_{14}$ is $C_{2-10}$ alkyl, $C_{2-10}$ alkenyl, $C_{2-10}$ alkynyl, heteroaryl, heterocyclyl, methoxy, $-OR_{15}$, $-NR_{16}R_{17}$, or

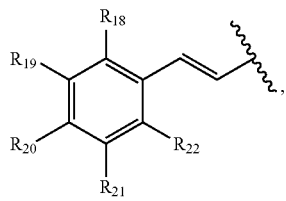

wherein $R_{15}$ is H, $C_{3-10}$ alkyl, $C_{2-10}$ alkenyl, $C_{2-10}$ alkynyl;

$R_{16}$ and $R_{17}$ are each, independently, H, $C_{1-10}$ alkyl, $C_{2-10}$ alkenyl, $C_{2-10}$ alkynyl, aryl, heteroaryl, or heterocyclyl;

$R_{18}$, $R_{19}$, $R_{21}$, and $R_{22}$ are each independently H, halogen, $-NO_2$, $-CN$, $-NR_{23}R_{24}$, $-SR_{23}$, $-SO_2R_{23}$, $-CO_2R_{23}$, $-OR_{25}$, $CF_3$, $C_{1-10}$ alkyl, $C_{2-10}$ alkenyl, $C_{2-10}$ alkynyl, aryl, heteroaryl, or heterocyclyl;

wherein $R_{23}$, $R_{24}$, and $R_{25}$ are each, independently, H, $C_{1-10}$ alkyl, $C_{2-10}$ alkenyl, $C_{2-10}$ alkynyl, aryl, heteroaryl, or heterocyclyl;

$R_{20}$ is halogen, $-NO_2$, $-CN$, $-NR_{26}R_{27}$, $CF_3$, $C_{1-10}$ alkyl, $C_{2-10}$ alkenyl, $C_{2-10}$ alkynyl, aryl, heteroaryl, or heterocyclyl;

wherein $R_{26}$ and $R_{27}$ are each, independently, H, $C_{1-10}$ alkyl, $C_{2-10}$ alkenyl, $C_{2-10}$ alkynyl, aryl, heteroaryl, or heterocyclyl;

$R_2$, $R_3$, $R_4$, $R_5$, $R_6$, $R_7$, $R_8$, $R_9$, $R_{10}$, and $R_{11}$ are each independently, H, halogen, $-NO_2$, $-CN$, $-NR_{28}R_{29}$, $-SR_{28}$, $-SO_2R_{28}$, $-OR_{28}$, $-CO_2R_{29}$, $CF_3$, $C_{1-10}$ alkyl, $C_{2-10}$ alkenyl, $C_{2-10}$ alkynyl, aryl, heteroaryl, or heterocyclyl;

wherein $R_{28}$ and $R_{29}$ are each, H, $CF_3$, $C_{1-10}$ alkyl, $C_{2-10}$ alkenyl, or $C_{2-10}$ alkynyl; and wherein each occurrence of alkyl, alkenyl, or alkynyl is branched or unbranched, unsubstituted or substituted; and wherein at least one of $R_2$, $R_3$, $R_3$, $R_5$, and $R_6$ and at least one of $R_7$, $R_8$, $R_9$, $R_{10}$, and $R_{11}$, are each, independently, $-OR_{28}$;

or a salt thereof.

In another embodiment, the compound has the structure

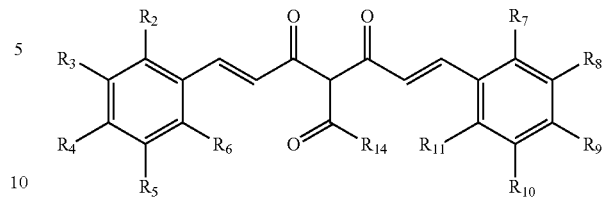

wherein $R_{14}$ is $C_{2-10}$ alkyl, $C_{2-10}$ alkenyl, $C_{2-10}$ alkynyl, heteroaryl, heterocyclyl, methoxy, $-OR_{15}$, $-NR_{15}R_{17}$, or

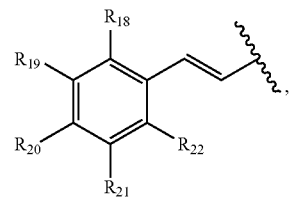

wherein $R_{15}$ is H, $C_{3-10}$ alkyl, $C_{2-10}$ alkenyl, $C_{2-10}$ alkynyl;

$R_{16}$ and $R_{17}$ are each, independently, H, $C_{1-10}$ alkyl, $C_{2-10}$ alkenyl, $C_{2-10}$ alkynyl, aryl, heteroaryl, or heterocyclyl;

$R_{18}$, $R_{19}$, $R_{21}$, and $R_{22}$ are each independently H, halogen, $-NO_2$, $-CN$, $-NR_{23}R_{24}$, $-SR_{23}$, $-SO_2R_{23}$, $-CO_2R_{23}$, $-OR_{25}$, $CF_3$, $C_{1-10}$ alkyl, $C_{2-10}$ alkenyl, $C_{2-10}$ alkynyl, aryl, heteroaryl, or heterocyclyl;

wherein $R_{23}$, $R_{24}$, and $R_{25}$ are each, independently, H, $C_{1-10}$ alkyl, $C_{2-10}$ alkenyl, $C_{2-10}$ alkynyl, aryl, heteroaryl, or heterocyclyl;

$R_{20}$ is halogen, $-NO_2$, $-CN$, $-NR_{26}R_{27}$, $CF_3$, $C_{1-10}$ alkyl, $C_{2-10}$ alkenyl, $C_{2-10}$ alkynyl, aryl, heteroaryl, or heterocyclyl;

wherein $R_{26}$ and $R_{27}$ are each, independently, H, $C_{1-10}$ alkyl, $C_{2-10}$ alkenyl, $C_{2-10}$ alkynyl, aryl, heteroaryl, or heterocyclyl;

$R_2$, $R_3$, $R_4$, $R_5$, $R_6$, $R_7$, $R_8$, $R_9$, $R_{10}$, and $R_{11}$ are each independently, H, halogen, $-NO_2$, $-CN$, $-NR_{28}R_{29}$, $-SR_{28}$, $-SO_2R_{28}$, $-OR_{28}$, $-CO_2R_{28}$, $CF_3$, $C_{1-10}$ alkyl, $C_{2-10}$ alkenyl, $C_{2-10}$ alkynyl, aryl, heteroaryl, or heterocyclyl;

wherein $R_{28}$ and $R_{29}$ are each, H, $CF_3$, $C_{1-10}$ alkyl, $C_{2-10}$ alkenyl, or $C_{2-10}$ alkynyl; and wherein each occurrence of alkyl, alkenyl, or alkynyl is branched or unbranched, unsubstituted or substituted; and wherein at least one of $R_2$, $R_3$, $R_4$, $R_5$, and $R_6$ and at least one of $R_7$, $R_8$, $R_9$, $R_{10}$, and $R_{11}$, are each, independently, $-OR_{28}$;

or a salt thereof.

In yet another embodiment, the compound has the structure

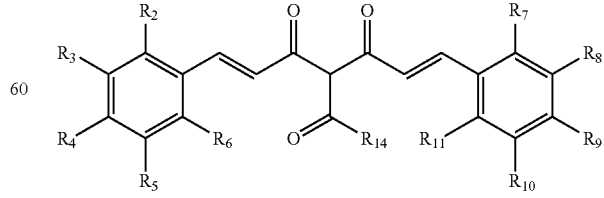

wherein $R_{14}$ is $C_{2-10}$ alkyl, $C_{2-10}$ alkenyl, $C_{2-10}$ alkynyl, heteroaryl, heterocyclyl, methoxy, $-OR_{15}$, $-NR_{16}R_{17}$, or

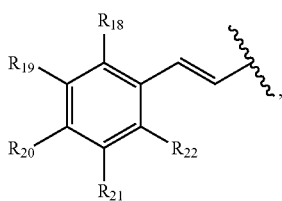

wherein $R_{15}$ is H, $C_{3-10}$ alkyl, $C_{2-10}$ alkenyl, $C_{2-10}$ alkynyl;

$R_{16}$ and $R_{17}$ are each, independently, H, $C_{1-10}$ alkyl, $C_{2-10}$ alkenyl, $C_{2-10}$ alkynyl, aryl, heteroaryl, or heterocyclyl;

$R_{18}$, $R_{19}$, $R_{21}$, and $R_{22}$ are each independently H, halogen, —$NO_2$, —CN, —$NR_{23}R_{24}$, —$SR_{23}$, —$SO_2R_{23}$, —$CO_2R_{23}$, —$OR_{25}$, $CF_3$, $C_{1-10}$ alkyl, $C_{2-10}$ alkenyl, $C_{2-10}$ alkynyl, aryl, heteroaryl, or heterocyclyl;

wherein $R_{23}$, $R_{24}$, and $R_{25}$ are each, independently, H, $C_{1-10}$ alkyl, $C_{2-10}$ alkenyl, $C_{2-10}$ alkynyl, aryl, heteroaryl, or heterocyclyl;

$R_{20}$ is halogen, —$NO_2$, —CN, —$NR_{26}R_{27}$, $CF_3$, $C_{1-10}$ alkyl, $C_{2-10}$ alkenyl, $C_{2-10}$ alkynyl, aryl, heteroaryl, or heterocyclyl;

wherein $R_{26}$ and $R_{27}$ are each, independently, H, $C_{1-10}$ alkyl, $C_{2-10}$ alkenyl, $C_{2-10}$ alkynyl, aryl, heteroaryl, or heterocyclyl;

$R_2$, $R_3$, $R_4$, $R_5$, $R_6$, $R_7$, $R_8$, $R_9$, $R_{10}$, and $R_{11}$ are each independently, H, halogen, —$NO_2$, —CN, —$NR_{28}R_{29}$, —$SR_{28}$, —$SO_2R_{28}$, —$OR_{28}$, —$CO_2R_{28}$, $CF_3$;

wherein $R_{28}$ and $R_{29}$ are each, H, $CF_3$, $C_{1-5}$ alkyl, $C_{2-5}$ alkenyl, or $C_{2-5}$ alkynyl; and wherein each occurrence of alkyl, alkenyl, or alkynyl is branched or unbranched, unsubstituted or substituted; and wherein at least one of $R_2$, $R_3$, $R_4$, $R_5$, and $R_6$ and at least one of $R_7$, $R_8$, $R_9$, $R_{10}$, and $R_{11}$, are each, independently, —$OR_{28}$;

or a salt thereof.

In an embodiment, $R_{14}$ is methoxy, —$OR_{15}$ or —$NR_{16}R_{17}$, wherein $R_{15}$ is H, $C_{3-10}$ alkyl, $C_{2-10}$ alkenyl, or $C_{2-10}$ alkynyl;

$R_{16}$ and $R_{17}$ are each, independently, H, $C_{1-10}$ alkyl, $C_{2-10}$ alkenyl, $C_{2-10}$ alkynyl, aryl, heteroaryl, or heterocyclyl;

or a salt thereof.

In another embodiment of the compound, $R_H$ is methoxy or —$NR_{16}R_{17}$, wherein $R_{16}$ and $R_{17}$ are each, independently, H, $C_{1-10}$ alkyl, $C_{2-10}$ alkenyl, $C_{2-10}$ alkynyl, aryl, heteroaryl, or heterocyclyl;

or a salt thereof.

In an embodiment, $R_{14}$ is —$OR_{15}$, wherein $R_{15}$ is H, $C_{3-10}$ alkyl, $C_{2-10}$ alkenyl, or $C_{2-10}$ alkynyl; or a salt thereof.

In an embodiment, $R_{14}$ is —$NR_{16}R_{17}$, wherein $R_{16}$ and $R_{17}$ are each, independently, H or aryl;

$R_2$, $R_3$, $R_4$, $R_5$, $R_6$, $R_7$, $R_8$, $R_9$, $R_{10}$, and $R_{11}$ are each independently, H, —$NR_{28}R_{29}$, or —$OR_{28}$, wherein $R_{28}$ and $R_{29}$ are each, H or $C_{1-10}$ alkyl; or a salt thereof.

In an embodiment, $R_{14}$ is —NH-phenyl;

$R_2$, $R_5$, $R_6$, $R_7$, $R_{10}$, and $R_{11}$ are each H;

$R_3$, $R_4$, $R_8$, and $R_9$ are each, independently, H, —OH, or —$OCH_3$; or a salt thereof.

In another embodiment, the compound has the structure

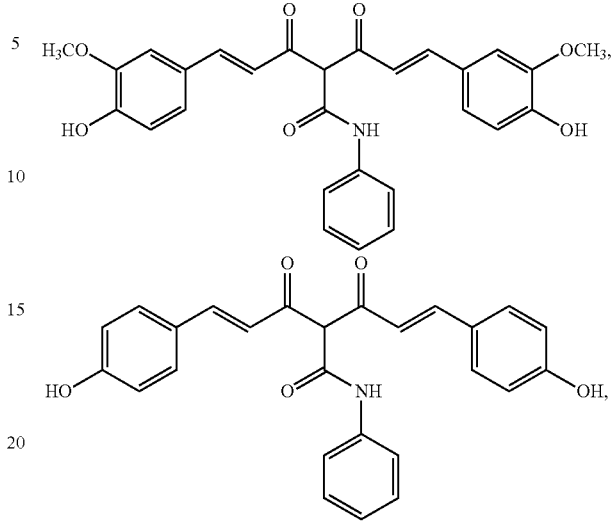

or a salt thereof.

In an embodiment, the compound has the structure

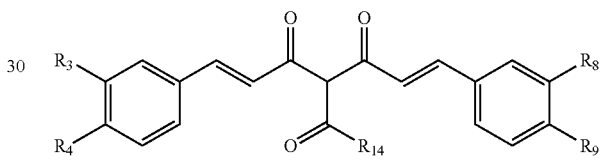

wherein $R_3$, $R_4$, $R_8$, and $R_9$ are H, —$OCH_3$, or —OH; $R_{14}$ is methoxy or —$N(CH_3)_2$; or a salt thereof.

In another embodiment, the compound has the structure

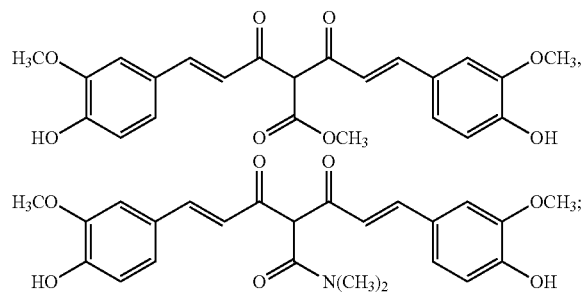

or a salt thereof.

In an embodiment, $R_{14}$ is methoxy;

$R_2$, $R_3$, $R_4$, $R_5$, $R_6$, $R_7$, $R_8$, $R_9$, $R_{10}$, and $R_{11}$ are each, independently, H, —OH, —$OCH_3$, —$NO_2$, or —$CO_2CH_3$; or a salt thereof.

In another embodiment, the compound has the structure

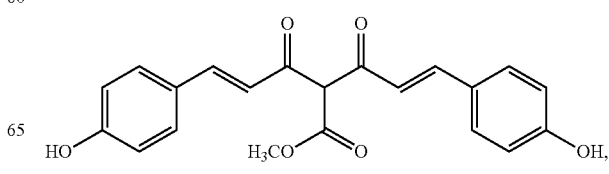

-continued

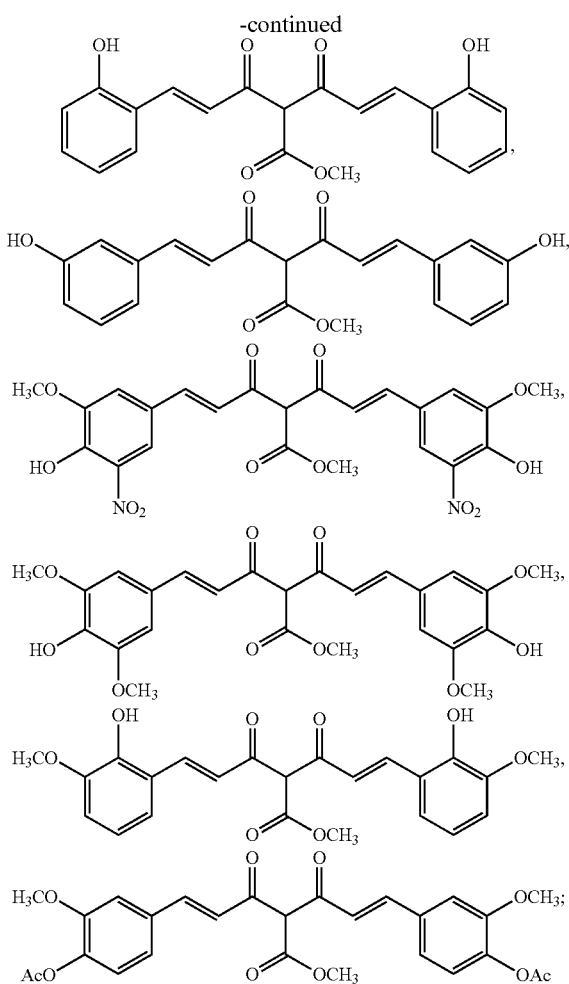

or a salt thereof.

In another embodiment, X is N; or a salt thereof.

In an embodiment, α and β are both present; or a salt thereof.

In another embodiment, the compound has the structure:

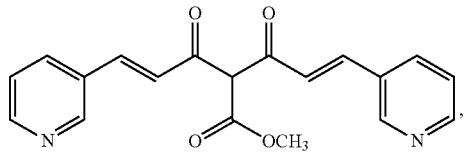 [SMILES: COC(=O)C(C(=O)/C=C/c1cccnc1)C(=O)/C=C/c1cccnc1]

or a salt thereof.

This invention provides a pharmaceutical composition comprising a pharmaceutically acceptable carrier and of the above compounds.

This invention also provides a method of inhibiting the activity and/or levels of a matrix metalloproteinase (MMP) comprising contacting the matrix metalloproteinase or a cell producing an MMP or MMPs with any one of the above compounds so as to inhibit the activity of a matrix metalloproteinase.

In an embodiment, the matrix metalloproteinase is MMP-1, MMP-2, MMP-3, MMP-7, MMP-8, MMP-9, MMP-12, MMP-13, or MMP-14.

This invention further provides a method of inhibiting the production of a cytokine in a population of mammalian cells comprising contacting the population of cells with any one of the above compounds so as to inhibit production of a cytokine.

In an embodiment, the population of cells is a population of human cells.

In another embodiment, the cytokine is THF-α, IL-1β, MCP-1, IL-8, or IL-6.

In yet another embodiment, the production of a cytokine is induced by an endotoxin, lipopolysaccharide (LPS), a hormone, a cholesterol complex, or an inflammatory mediator, including but not limited to nitric oxide, and reactive oxygen species.

This invention yet further provides a method of inhibiting the production of a growth factor in a population of mammalian cells comprising contacting the population of cells with the any one of the above compounds so as to inhibit production of a growth factor.

In an embodiment, the growth factor is VEGF, PDGF, TGF-β, or MIP1α.

This invention provides a method of inhibiting NFκ-B activation in a population of cells comprising contacting the population of cells with the any one of the above compounds so as to inhibit NFκ-B activation.

In an embodiment, the population of cells is a population of human cells.

This invention provides a method of increasing water solubility, metal binding ability, MMP inhibition activity, cytokine inhibition activity, growth factor inhibition activity, or NFκB activation inhibition activity of curcumin comprising synthesizing a compound having the structure

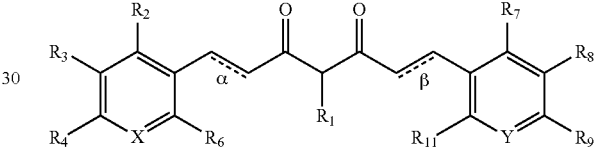

wherein
bond α and β are each, independently, present or absent;
X is $CR_5$ or N; Y is $CR_{10}$ or N;
$R_1$ is H or an electron-withdrawing group;
$R_2$, $R_3$, $R_4$, $R_5$, $R_6$, $R_7$, $R_8$, $R_9$, $R_{10}$, and $R_{11}$ are each independently, H, halogen, —$NO_2$, —CN, —$NR_{28}R_{29}$, —$NHR_{28}R_{29}^+$, —$SR_{28}$, —$SO_2R_{28}$, —$OR_{28}$, —$CO_2R_{28}$, $CF_3$, $C_{1-10}$ alkyl, $C_{2-10}$ alkenyl, $C_{2-10}$ alkynyl, aryl, heteroaryl, or heterocyclyl;
wherein $R_{28}$ and $R_{29}$ are each, H, $CF_3$, $C_{1-10}$ alkyl, $C_{2-10}$ alkenyl, $C_{2-10}$ alkynyl, or —C(=O)-heterocyclyl; and
wherein when $R_1$ is H, $R_3$, $R_4$, $R_5$, $R_8$, $R_9$, or $R_{10}$, is halogen, —$NO_2$, —CN, —$NR_{28}R_{29}$, —$NHR_{28}R_{29}^+$, —$SR_{28}$, —$SO_2R_{28}$, $CO_2R_{28}$, $CF_3$, $C_{1-10}$ alkyl, $C_{2-10}$ alkenyl, $C_{2-10}$ alkynyl, aryl, heteroaryl, or heterocyclyl;
wherein $R_{28}$ and $R_{29}$ are each, H, $CF_3$, $C_{1-10}$ alkyl, $C_{2-10}$ alkenyl, $C_{2-10}$ alkynyl, or —C(=O)-heterocyclyl; and
wherein each occurrence of alkyl, alkenyl, or alkynyl is branched or unbranched, unsubstituted or substituted;
or a salt thereof.

In an embodiment, the compound synthesized has the structure

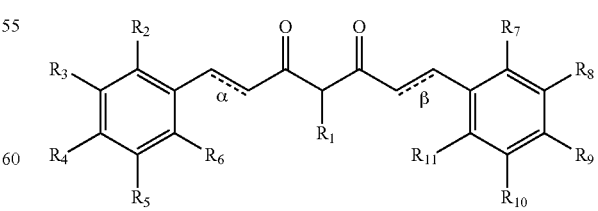

wherein
bond α and β are each, independently, present or absent;
$R_1$ is an electron-withdrawing group;
$R_2$, $R_3$, $R_4$, $R_5$, $R_6$, $R_7$, $R_8$, $R_9$, $R_{10}$, and $R_{11}$ are each independently, H, halogen, —$NO_2$, —CN, —$NR_{28}R_{29}$, —$SR_{28}$, —$SO_2R_{28}$, —$OR_{28}$, —$CO_2R_{28}$, $CF_3$, $C_{1-10}$ alkyl, $C_{2-10}$ alkenyl, $C_{2-10}$ alkynyl, aryl, heteroaryl, or heterocyclyl;
wherein $R_{28}$ and $R_{29}$ are each, H, $CF_3$, $C_{1-10}$ alkyl, $C_{2-10}$ alkenyl, or $C_{2-10}$ alkynyl; and
wherein each occurrence of alkyl, alkenyl, or alkynyl is branched or unbranched, unsubstituted or substituted; and
wherein at least one of $R_2$, $R_3$, $R_4$, $R_5$, and $R_6$ and at least one of $R_7$, $R_8$, $R_9$, $R_{10}$, and $R_{11}$, are each, independently, —$OR_{28}$;
or a salt thereof.

In an embodiment, the compound synthesized has the structure

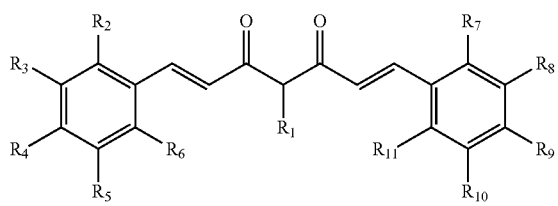

wherein
$R_1$ is an electron-withdrawing group;
$R_2$, $R_3$, $R_4$, $R_5$, $R_6$, $R_7$, $R_8$, $R_9$, $R_{10}$, and $R_{11}$ are each independently, H, halogen, —$NO_2$, —CN, —$NR_{28}R_{29}$, —$SR_{28}$, —$SO_2R_{28}$, —$OR_{28}$, —$CO_2R_{28}$, $CF_3$, $C_{1-10}$ alkyl, $C_{2-10}$ alkenyl, $C_{2-10}$ alkynyl, aryl, heteroaryl, or heterocyclyl;
wherein $R_{28}$ and $R_{29}$ are each, H, $CF_3$, $C_{1-10}$ alkyl, $C_{2-10}$ alkenyl, or $C_{2-10}$ alkynyl; and
wherein each occurrence of alkyl, alkenyl, or alkynyl is branched or unbranched, unsubstituted or substituted; and
wherein at least one of $R_2$, $R_3$, $R_4$, $R_5$, and $R_6$ and at least one of $R_7$, $R_8$, $R_9$, $R_{10}$, and $R_{11}$, are each, independently, —$OR_{28}$;
or a salt thereof.

In another embodiment, the compound synthesized has the structure

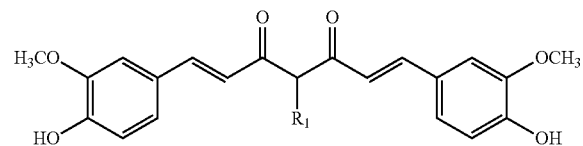

wherein $R_1$ is an electron-withdrawing group.

It is understood that the structures described in the embodiments of the methods hereinabove can be the same as the structures of the compounds described hereinabove.

As used herein, the term "activity" refers to the activation, production, expression, synthesis, intercellular effect, and/or pathological or aberrant effect of the referenced molecule, either inside and/or outside of a cell. Such molecules include, but are not limited to, cytokines, enzymes, growth factors, pro-growth factors, active growth factors, and pro-enzymes. Molecules such as cytokines, enzymes, growth factors, pro-growth factors, active growth factors, and pro-enzymes may be produced, expressed, or synthesized within a cell where they may exert an effect. Such molecules may also be transported outside of the cell to the extracellular matrix where they may induce an effect on the extracellular matrix or on a neighboring cell. It is understood that activation of inactive cytokines, enzymes and pro-enzymes may occur inside and/or outside of a cell and that both inactive and active forms may be present at any point inside and/or outside of a cell. It is also understood that cells may possess basal levels of such molecules for normal function and that abnormally high or low levels of such active molecules may lead to pathological or aberrant effects that may be corrected by pharmacological intervention.

The term "cytokine" as used herein refers to a cellular signaling molecule, which includes, but is not limited to, a lymphokine, a monokine, a chemokine, an interferon, an interleukin, or a hormone. Examples of a monokine include, but are not limited to, TNF-α and TNF-β. Examples of a chemokine include, but are not limited to, MCP-1, MCP-2, and MCP-3. Examples of an interferon include, but are not limited to, IFN-α, IFN-β, and IFN-γ. Examples of an interleukin include, but are not limited to, IL-1α, IL1-β, IL-2, IL-3, IL-4, IL-5, IL-6, IL-7, IL-8, IL-10, and IL-12.

The term "growth factor" as used herein refers to a protein that binds to receptors on the cell surface, with the primary function of regulating cellular proliferation and/or differentiation. Examples of a growth factor include, but are not limited to, G-CSF, GM-CSF, MIP1α, MIP1β, TGF-α, TGF-β, VEGF, and PDGF.

The compounds of the present invention include all hydrates, solvates, and complexes of the compounds used by this invention. If a chiral center or another form of an isomeric center is present in a compound of the present invention, all forms of such isomer or isomers, including enantiomers and diastereomers, are intended to be covered herein. Compounds containing a chiral center may be used as a racemic mixture, an enantiomerically enriched mixture, or the racemic mixture may be separated using well-known techniques and an individual enantiomer may be used alone. The compounds described in the present invention are in racemic form or as individual enantiomers. The enantiomers can be separated using known techniques, such as those described in Pure and Applied Chemistry 69, 1469-1474, (1997) IUPAC. In cases in which compounds have unsaturated carbon-carbon double bonds, both the cis (Z) and trans (E) isomers are within the scope of this invention.

The compounds of the subject invention may have spontaneous tautomeric forms. In cases wherein compounds may exist in tautomeric forms, such as keto-enol tautomers, each tautomeric form is contemplated as being included within this invention whether existing in equilibrium or predominantly in one form.

In the compound structures depicted herein, hydrogen atoms are not shown for carbon atoms having less than four bonds to non-hydrogen atoms. However, it is understood that enough hydrogen atoms exist on said carbon atoms to satisfy the octet rule.

As used herein, "alkyl" includes both branched and straight-chain saturated aliphatic hydrocarbon groups having the specified number of carbon atoms and may be unsubstituted or substituted. Thus, $C_1$-$C_n$ as in "$C_1$-$C_n$ alkyl" is defined to include groups having 1, 2, ..., n−1 or n carbons in a linear or branched arrangement. For example, $C_1$-$C_6$, as in "$C_1$-$C_6$ alkyl" is defined to include groups having 1, 2, 3, 4, 5, or 6 carbons in a linear or branched arrangement, and specifically includes methyl, ethyl, n-propyl, isopropyl, n-butyl, t-butyl, pentyl, hexyl, and octyl.

As used herein, "alkenyl" refers to a non-aromatic hydrocarbon radical, straight or branched, containing at least 1 carbon to carbon double bond, and up to the maximum possible number of non-aromatic carbon-carbon double bonds may be present, and may be unsubstituted or substituted. For example, "$C_2$-$C_6$ alkenyl" means an alkenyl radical having 2, 3, 4, 5, or 6 carbon atoms, and up to 1, 2, 3, 4, or 5 carbon-carbon double bonds respectively. Alkenyl groups include ethenyl, propenyl, butenyl and cyclohexenyl.

The term "alkynyl" refers to a hydrocarbon radical straight or branched, containing at least 1 carbon to carbon triple bond, and up to the maximum possible number of non-aromatic carbon-carbon triple bonds may be present, and may be unsubstituted or substituted. Thus, "$C_2$-$C_6$ alkynyl" means an alkynyl radical having 2 or 3 carbon atoms and 1 carbon-carbon triple bond, or having 4 or 5 carbon atoms and up to 2 carbon-carbon triple bonds, or having 6 carbon atoms and up to 3 carbon-carbon triple bonds. Alkynyl groups include ethynyl, propynyl and butynyl.

"Alkylene", "alkenylene" and "alkynylene" shall mean, respectively, a divalent alkane, alkene and alkyne radical, respectively. It is understood that an alkylene, alkenylene, and alkynylene may be straight or branched. An alkylene, alkenylene, and alkynylene may be unsubstituted or substituted.

As used herein, "aryl" is intended to mean any stable monocyclic, bicyclic or polycyclic carbon ring of up to 10 atoms in each ring, wherein at least one ring is aromatic, and may be unsubstituted or substituted. Examples of such aryl elements include phenyl, p-toluenyl(4-methylphenyl), naphthyl, tetrahydro-naphthyl, indanyl, biphenyl, phenanthryl, anthryl or acenaphthyl. In cases where the aryl substituent is bicyclic and one ring is non-aromatic, it is understood that attachment is via the aromatic ring. Where an aryl group is polycyclic, at least 2 aromatic rings are adjacent, ie. share one side. For example, polycyclic aryl groups do not include moieties containing a tetracycline structure.

Further, the use of the term "polycyclic" is not limited to aryl groups. The term "polycyclic" as used herein may also refer to unsaturated or partially unsaturated multiple fused ring structures. However, the term "polycyclic" as used herein in any context excludes the tetracycline structure.

The term "arylalkyl" refers to alkyl groups as described above wherein one or more bonds to hydrogen contained therein are replaced by a bond to an aryl group as described above. It is understood that an "arylalkyl" group is connected to a core molecule through a bond from the alkyl group and that the aryl group acts as a substituent on the alkyl group. Examples of arylalkyl moieties include, but are not limited to, benzyl(phenylmethyl), p-trifluoromethylbenzyl(4-trifluoromethylphenylmethyl), 1-phenylethyl, 2-phenylethyl, 3-phenylpropyl, 2-phenylpropyl and the like.

The term "heteroaryl", as used herein, represents a stable monocyclic, bicyclic or polycyclic ring of up to 10 atoms in each ring, wherein at least one ring is aromatic and contains from 1 to 4 heteroatoms selected from the group consisting of O, N and S. Bicyclic aromatic heteroaryl groups include phenyl, pyridine, pyrimidine or pyridizine rings that are (a) fused to a 6-membered aromatic (unsaturated) heterocyclic ring having one nitrogen atom; (b) fused to a 5- or 6-membered aromatic (unsaturated) heterocyclic ring having two nitrogen atoms; (c) fused to a 5-membered aromatic (unsaturated) heterocyclic ring having one nitrogen atom together with either one oxygen or one sulfur atom; or (d) fused to a 5-membered aromatic (unsaturated) heterocyclic ring having one heteroatom selected from O, N or S. Heteroaryl groups within the scope of this definition include but are not limited to: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrazolyl, tetrazolopyridyl, thiadiazolyl, thiazolyl, thienyl, triazolyl, azetidinyl, aziridinyl, 1,4-dioxanyl, hexahydroazepinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, tetrahydrothienyl, acridinyl, carbazolyl, cinnolinyl, quinoxalinyl, pyrrazolyl, indolyl, benzotriazolyl, benzothiazolyl, benzoxazolyl, isoxazolyl, isothiazolyl, furanyl, thienyl, benzothienyl, benzofuranyl, quinolinyl, isoquinolinyl, oxazolyl, isoxazolyl, indolyl, pyrazinyl, pyridazinyl, pyridinyl, pyrimidinyl, pyrrolyl, tetra-hydroquinoline. In cases where the heteroaryl substituent is bicyclic and one ring is non-aromatic or contains no heteroatoms, it is understood that attachment is via the aromatic ring or via the heteroatom containing ring, respectively. If the heteroaryl contains nitrogen atoms, it is understood that the corresponding N-oxides thereof are also encompassed by this definition.

The term "heterocycle" or "heterocyclyl" refers to a mono- or poly-cyclic ring system which can be saturated or contains one or more degrees of unsaturation and contains one or more heteroatoms. Preferred heteroatoms include N, O, and/or S, including N-oxides, sulfur oxides, and dioxides. Preferably the ring is three to ten-membered and is either saturated or has one or more degrees of unsaturation. The heterocycle may be unsubstituted or substituted, with multiple degrees of substitution being allowed. Such rings may be optionally fused to one or more of another "heterocyclic" ring(s), heteroaryl ring(s), aryl ring(s), or cycloalkyl ring(s). Examples of heterocycles include, but are not limited to, tetrahydrofuran, pyran, 1,4-dioxane, 1,3-dioxane, piperidine, piperazine, pyrrolidine, morpholine, thiomorpholine, tetrahydrothiopyran, tetrahydrothiophene, 1,3-oxathiolane, and the like.

The alkyl, alkenyl, alkynyl, aryl, heteroaryl and heterocyclyl substituents may be substituted or unsubstituted, unless specifically defined otherwise.

In the compounds of the present invention, alkyl, alkenyl, alkynyl, aryl, heterocyclyl and heteroaryl groups can be further substituted by replacing one or more hydrogen atoms with alternative non-hydrogen groups. These include, but are not limited to, halo, hydroxy, mercapto, amino, carboxy, cyano and carbamoyl.

As used herein, the term "halogen" refers to F, Cl, Br, and I.

The term "substituted" refers to a functional group as described above in which one or more bonds to a hydrogen atom contained therein are replaced by a bond to non-hydrogen or non-carbon atoms, provided that normal valencies are maintained and that the substitution results in a stable compound. Substituted groups also include groups in which one or more bonds to a carbon(s) or hydrogen(s) atom are replaced by one or more bonds, including double or triple bonds, to a heteroatom. Examples of substituents include the functional groups described above, and, in particular, halogens (ie., F, Cl, Br, and I); alkyl groups, such as methyl, ethyl, n-propyl, isopropryl, n-butyl, tert-butyl, and trifluoromethyl; hydroxyl; alkoxy groups, such as methoxy, ethoxy, n-propoxy, and isopropoxy; aryloxy groups, such as phenoxy; arylalkyloxy, such as benzyloxy (phenylmethoxy) and p-trifluoromethylbenzyloxy(4-trifluoromethylphenylmethoxy); heteroaryloxy groups; sulfonyl groups, such as trifluoromethanesulfonyl, methanesulfonyl, and p-toluenesulfonyl;

nitro, nitrosyl; mercapto; sulfanyl groups, such as methylsulfanyl, ethylsulfanyl and propylsulfanyl; cyano; amino groups, such as amino, methylamino, dimethylamino, ethylamino, and diethylamino; and carboxyl. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results.

As used herein, abbreviations are defined as follows:
DNA=deoxyribonucleic acid
RNA=ribonucleic acid
IL=interleukin
MCP=monocyte chemoattractant protein
TNF=tumor necrosis factor
VEGF=vascular endothelial growth factor
MMP=matrix metalloproteinase
LBS=lipopolysaccharide
HPLC=high-performance liquid chromatography
DLAR=Division of Laboratory Animal Resources In choosing the compounds of the present invention, one of ordinary skill in the art will recognize that the various substituents, ie. $R_1$, $R_2$, etc. are to be chosen in conformity with well-known principles of chemical structure connectivity.

The various R groups attached to the aromatic rings of the compounds disclosed herein may be added to the rings by standard procedures, for example those set forth in Advanced Organic Chemistry: Part B: Reaction and Synthesis, Francis Carey and Richard Sundberg, (Springer) 5th ed. Edition. (2007), the content of which is hereby incorporated by reference.

While curcumin has been known to bind metal ions such as those of copper, iron, and zinc, affinity for zinc has been shown to be weak (19).

In the subject invention, the improved biological activity of curcumin and its analogues is attributed in part to their ability to access and bind zinc ions and an enhanced solubility. This invention describes that the enhancement of zinc binding affinity through the installation of electron-withdrawing and electron-donating groups at strategic locations, namely the C-4 carbon and the aryl rings, on the curcumin skeleton and results in the enhancement of biological activity, including inhibition of MMP activity, NFκB activation, and cytokine production.

Without wishing to be bound by theory, it is believed that zinc binding affinity arises from increased stability of the curcumin enolate formed by removal of hydrogen from the C-4 carbon, which then proceeds to form a complex with zinc. The stability of a carbanion, including an enolate, is directly related to the acidity of the ionizable hydrogen, such as an enolic hydrogen. In general, the stability of an enolate increases with increasing acidity of the enolic hydrogen. Herein, the enolic hydrogen refers to the hydrogen atom connected to the C-4 carbon of the curcumin skeleton.

The acidity of the enolic hydrogen of curcumin and its analogues can be enhanced by incorporation of an electron-withdrawing group at the C-4 carbon. Substituents which delocalize negative charge will enhance acidity and stability of the resulting carbanion, such as an enolate. Again, without wishing to be bound by theory, it is believed that the electron-withdrawing group allows the negative charge of the enolate to be delocalized into the electron-withdrawing group, thereby stabilizing the enolate, enhancing its stability, and increasing its zinc binding affinity.

The electronic characteristics of the aryl rings of curcumin are also relevant for enhancing zinc binding affinity and biological activity. While not required, electron-donating groups on the aryl portions of the curcumin skeleton seem to improve its activity. The incorporation of such electron-donating groups on the aryl rings may affect one or more factors, including enhancement of water solubility and improvement of cation-pi interactions. Without wishing to be bound by theory, the installation of electron-donating groups on the aryl rings, in conjunction with the choice of C-4 electron-withdrawing group, is believed to increase electron polarization within the molecule such that intermolecular dipole-dipole forces with surrounding water molecules is enhanced, thereby increasing water solubility. Electron-donating groups may also increase water solubility by enhancing hydrogen-bonding interactions with surrounding water molecules. Furthermore, with respect to cation-pi interactions, it is believed that electron-donating groups increase electron density on the aryl rings, thereby enhancing the aryls' ability to recognize and/or bind to cations or cation-containing proteins.

The choice of electron-withdrawing groups on the C-4 carbon and the choice of electron-donating groups on the aryl rings may be chosen using techniques well known by the ordinarily skilled artisan. In general, the electron donating ability of common substituents suitable for use on the aryl rings can be estimated by their Hammett σ values. The Hammett $\sigma_{para}$ value is a relative measurement comparing the electronic influence of the substituent in the para position of a phenyl ring to the electronic influence of a hydrogen substituted at the para position. Typically for aromatic substituents in general, a negative Hammett $\sigma_{para}$ value is indicative of a group or substituent having an electron-donating influence on a pi electron system (ie., an electron-donating group) and a positive Hammett $\sigma_{para}$ value is indicative of a group or substituent having an electron-withdrawing influence on a pi electron system (ie., an electron-withdrawing group). Similarly, Hammett $\sigma_{meta}$ value is a relative measurement comparing the electronic influence of the substituent in the meta position of a phenyl ring to the electronic influence of a hydrogen substituted at the meta position. A list of Hammett $\sigma_{para}$ and $\sigma_{meta}$ values for common substituents can be found in Lowry and Richardson, "Mechanism and Theory in Organic Chemistry", 3rd ed, p. 144. The effect of some substituents, including some electron-withdrawing groups, on C—H acidity can also be found on page 518 in Lowry and Richardson, "Mechanism and Theory in Organic Chemistry", 3rd ed, the content of which is hereby incorporated by reference.

Computation methods may be used by the ordinarily skilled artisan to quantify and predict the effects of the chosen electron-donating and electron-withdrawing groups on curcumin zinc-binding affinity, water solubility and pKa (acid dissociation constant) of ionizable hydrogens, among other pharmaceutical properties. Commercially-available software that may be used, alone or in combination, for such computational methods includes, but is not limited to, ACD/PhysChem Suite® (Advanced Chemical Development, Inc., Ontario, Canada), Gaussian 03 (Gaussian, Inc., Wallingford, Conn.), Spartan® (Wavefunction, Inc., Irvine, Calif.), MacroModel and QikProp (Schrödinger, Inc., New York, N.Y.).

As used herein, the term "electron-withdrawing group" refers to a substituent or functional group that has the property of increasing electron density around itself relative to groups in its proximity. Electron withdrawing property is a combination of induction and resonance. Electron withdrawal by induction refers to electron cloud displacement towards the more electronegative of two atoms in a σ-bond. Therefore, the electron cloud between two atoms of differing electronegativity is not uniform and a permanent state of bond polarization occurs such that the more electronegative atom has a slight negative charge and the other atom has a slight positive charge. Electron withdrawal by resonance refers to the ability of substituents or functional groups to withdraw electron density on the basis of relevant resonance structures arising from p-orbital overlap. Suitable electron-withdrawing groups include, but are not limited to, —CN, —CF$_3$, halogen, —NO$_2$, —OCF$_3$, —OR$_{12}$, —NHCOR$_{12}$, —SR$_{12}$, —SO$_2$R$_{13}$, —COR$_{14}$, —CSR$_{14}$, —CNR$_{14}$, —C(=NR$_{12}$)R$_{14}$, —C(=NH)R$_{14}$, —SOR$_{12}$, —POR$_{12}$, —P(=O)(OR$_{12}$)(OR$_{13}$), or —P(OR$_{12}$)(OR$_{13}$), wherein R$_{12}$ and R$_{13}$ are each, independently, H, C$_{1-10}$ alkyl, C$_{2-10}$ alkenyl, C$_{2-10}$ alkynyl, aryl, heteroaryl, or heterocyclyl;

R$_{14}$ is C$_{2-10}$ alkyl, C$_{2-10}$ alkenyl, C$_{2-10}$ alkynyl, heteroaryl, heterocyclyl, methoxy, —OR$_{15}$, —NR$_{16}$R$_{17}$, or

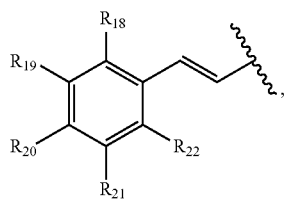

wherein R$_{15}$ is H, C$_{3-10}$ alkyl, C$_{2-10}$ alkenyl, C$_{2-10}$ alkynyl;

R$_{15}$ and R$_{17}$ are each, independently, H, C$_{1-10}$ alkyl, C$_{2-10}$ alkenyl, C$_{2-10}$ alkynyl, aryl, heteroaryl, or heterocyclyl;

R$_{18}$, R$_{19}$, R$_{21}$, and R$_{22}$ are each independently H, halogen, —NO$_2$, —CN, —NR$_{23}$R$_{24}$, —SR$_{23}$, —SO$_2$R$_{23}$, —CO$_2$R$_{23}$, —OR$_{25}$, CF$_3$, —SOR$_{23}$, —POR$_{23}$, —C(=S)R$_{23}$, —C(=NH)R$_{23}$, C(=NR$_{24}$)R$_{23}$, —C(=N)R$_{23}$, P(=O)(OR$_{23}$)(OR$_{24}$)—(OR$_{23}$)(OR$_{24}$), —C(=S)R$_{23}$, C$_{1-10}$ alkyl, C$_{2-10}$ alkenyl, C$_{2-10}$ alkynyl, aryl, heteroaryl, or heterocyclyl;

wherein R$_{23}$, R$_{24}$, and R$_{25}$ are each, independently, H, C$_{1-10}$ alkyl, C$_{2-10}$ alkenyl, C$_{2-10}$ alkynyl, aryl, heteroaryl, or heterocyclyl;

R$_{20}$ is halogen, —NO$_2$, —CN, —NR$_{26}$R$_{27}$, CF$_3$, C$_{1-10}$ alkyl, C$_{2-10}$ alkenyl, C$_{2-10}$ alkynyl, aryl, heteroaryl, or heterocyclyl;

wherein R$_{26}$ and R$_{27}$ are each, independently, H, C$_{1-10}$ alkyl, C$_{2-20}$ alkenyl, C$_{2-10}$ alkynyl, aryl, heteroaryl, or heterocyclyl.

The compounds of the instant invention may be in a salt form. As used herein, a "salt" is the salt of the instant compounds which has been modified by making acid or base salts of the compounds. Acidic substances can form salts with acceptable bases, including, but not limited to, lysine, arginine, and the like. In the case of compounds administered to a subject, e.g. a human, the salt is pharmaceutically acceptable. Examples of pharmaceutically acceptable salts include, but are not limited to, mineral or organic acid salts formed at basic residues such as amino groups; alkali or organic base salts formed at acidic residues such as phenols, carboxylic acids, and carbons having at least 1 acidic hydrogen atom adjacent to a carbonyl. Where acid salts are formed, such salts can be made using an organic or inorganic acid. Such acid salts include, but are not limited to, chlorides, bromides, sulfates, nitrates, phosphates, sulfonates, formates, tartrates, maleates, malates, citrates, benzoates, salicylates, ascorbates, and the like. Because the compounds of the subject invention also possess carbons having at least 1 acidic hydrogen atom adjacent to a carbonyl, enolate salts may be formed by reaction with a suitable base. Suitable bases include, but are not limited, to inorganic bases, such as alkali and alkaline earth metal hydroxides; and organic bases, including, but not limited to, ammonia, alkyl amines, amino alcohols, amino sugars, amino acids, such as glycine, histidine, and lysine, and alkali metal amides, such as lithium diisopropylamide. The term "pharmaceutically acceptable salt" in this respect, refers to the relatively non-toxic, inorganic and organic acid or base addition salts of compounds of the present invention. These salts can be prepared in situ during the final isolation and purification of the compounds of the invention, or by separately reacting a purified compound of the invention in its free base or free acid form with a suitable organic or inorganic acid or base, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, e.g., Berge et al. (1977) "Pharmaceutical Salts", *J. Pharm. Sci.* 66:1-19).

The compounds and compositions of this invention may be administered in various forms, including those detailed herein. The treatment with the compound may be a component of a combination therapy or an adjunct therapy, ie. the subject or patient in need of the drug is treated or given another drug for the disease in conjunction with one or more of the instant compounds. This combination therapy can be sequential therapy where the patient is treated first with one drug and then the other or the two drugs are given simultaneously. These can be administered independently by the same route or by two or more different routes of administration depending on the dosage forms employed.

As used herein, a "pharmaceutically acceptable carrier" is a pharmaceutically acceptable solvent, suspending agent or vehicle, for delivering the instant compounds to the animal or human. The carrier may be liquid or solid and is selected with the planned manner of administration in mind. Liposomes are also a pharmaceutically acceptable carrier.

The dosage of the compounds administered in treatment will vary depending upon factors such as the pharmacodynamic characteristics of a specific chemotherapeutic agent and its mode and route of administration; the age, sex, metabolic rate, absorptive efficiency, health and weight of the recipient; the nature and extent of the symptoms; the kind of concurrent treatment being administered; the frequency of treatment with; and the desired therapeutic effect.

A dosage unit of the compounds may comprise a single compound or mixtures thereof with other compounds also used to treat rheumatoid arthritis (RA), osteoarthritis (OA), metastases, periodontal disease, such as periodontitis, angiogenesis, emphysema, acute respiratory distress syndrome, multiple sclerosis, cardiovascular disease, such as atherosclerosis, myocardial infarction, arterial restenosis after angioplasty and aneurysm development; inflammatory disorders, including neuroinflammation and inflammatory bowel disease; many types of cancer, including breast cancer, skin cancer, including, but not limited to, melanoma, and prostate cancer; diabetes, stroke, peripheral neuropathy, brain trauma, pancreatitis, and skin disorders, including, but not limited to, wounds, including ulcers of the skin, accelerated aging, and inflammatory diseases of the skin; bone diseases including, but not limited to, osteoperosis. The compounds can be administered in oral dosage forms as tablets, capsules, pills, powders, granules, elixirs, tinctures, suspensions, syrups, and emulsions. The compounds may also be administered in intravenous (bolus or infusion), intraperitoneal, subcutaneous, or intramuscular form, or introduced directly, e.g. by topical administration, injection or other methods, to the afflicted area, such as a wound, including ulcers of the skin, all using dosage forms well known to those of ordinary skill in the pharmaceutical arts.

The compounds can be administered in admixture with suitable pharmaceutical diluents, extenders, excipients, or carriers (collectively referred to herein as a pharmaceutically acceptable carrier) suitably selected with respect to the intended form of administration and as consistent with conventional pharmaceutical practices. The unit will be in a form suitable for oral, rectal, topical, intravenous or direct injection or parenteral administration. The compounds can be administered alone but are generally mixed with a pharmaceutically acceptable carrier. This carrier can be a solid or liquid, and the type of carrier is generally chosen based on the type of administration being used. In one embodiment the carrier can be a monoclonal antibody. The active agent can be co-administered in the form of a tablet or capsule, liposome, as an agglomerated powder or in a liquid form. Examples of suitable solid carriers include lactose, sucrose, gelatin and agar. Capsule or tablets can be easily formulated and can be made easy to swallow or chew; other solid forms include granules, and bulk powders. Tablets may contain suitable binders, lubricants, diluents, disintegrating agents, coloring agents, flavoring agents, flow-inducing agents, and melting agents. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents. Oral dosage forms optionally contain flavorants and coloring agents. Parenteral and intravenous forms may also include minerals and other materials to make them compatible with the type of injection or delivery system chosen.

Specific examples of pharmaceutical acceptable carriers and excipients that may be used to formulate oral dosage forms of the present invention are described in U.S. Pat. No. 3,903,297 to Robert, issued Sep. 2, 1975. Techniques and compositions for making dosage forms useful in the present invention are described-in the following references: 7 Modern Pharmaceutics, Chapters 9 and 10 (Banker & Rhodes, Editors, 1979); Pharmaceutical Dosage Forms: Tablets (Lieberman et al., 1981); Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modem Pharmaceutics Drugs and the Pharmaceutical Sciences, Vol 40 (Gilbert S. Banker, Christopher T. Rhodes, Eds.). All of the aforementioned publications are incorporated by reference herein.

Tablets may contain suitable binders, lubricants, disintegrating agents, coloring agents, flavoring agents, flow-inducing agents, and melting agents. For instance, for oral administration in the dosage unit form of a tablet or capsule, the active drug component can be combined with an oral, non-toxic, pharmaceutically acceptable, inert carrier such as lactose, gelatin, agar, starch, sucrose, glucose, methyl cellulose, magnesium stearate, dicalcium phosphate, calcium sulfate, mannitol, sorbitol and the like. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds can also be administered in the form of liposome delivery systems, such as small unilamellar vesicles, large unilamallar vesicles, and multilamellar vesicles. Liposomes can be formed from a variety of phospholipids, such as cholesterol, stearylamine, or phosphatidylcholines. The compounds may be administered as components of tissue-targeted emulsions.

The compounds may also be coupled to soluble polymers as targetable drug carriers or as a prodrug. Such polymers include polyvinylpyrrolidone, pyran copolymer, polyhydroxylpropylmethacrylamide-phenol, polyhydroxyethylasparta-midephenol, or polyethylene oxide-polylysine substituted with palmitoyl residues. Furthermore, the compounds may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

The term "prodrug" as used herein refers to any compound that when administered to a biological system generates the compound of the invention, as a result of spontaneous chemical reaction(s), enzyme catalyzed chemical reaction(s), photolysis, and/or metabolic chemical reaction(s). A prodrug is thus a covalently modified analog or latent form of a compound of the invention.

The active ingredient can be administered orally in solid dosage forms, such as capsules, tablets, powders, and chewing gum; or in liquid dosage forms, such as elixirs, syrups, and suspensions, including, but not limited to, mouthwash and toothpaste. It can also be administered parentally, in sterile liquid dosage forms.

Solid dosage forms, such as capsules and tablets, may be enteric coated to prevent release of the active ingredient compounds before they reach the small intestine. Materials that may be used as enteric coatings include, but are not limited to, sugars, fatty acids, waxes, shellac, cellulose acetate phthalate (CAP), methyl acrylate-methacrylic acid copolymers, cellulose acetate succinate, hydroxy propyl methyl cellulose phthalate, hydroxy propyl methyl cellulose acetate succinate (hypromellose acetate succinate), polyvinyl acetate phthalate (PVAP), and methyl methacrylate-methacrylic acid copolymers.

Gelatin capsules may contain the active ingredient compounds and powdered carriers, such as lactose, starch, cellulose derivatives, magnesium stearate, stearic acid, and the like. Similar diluents can be used to make compressed tablets. Both tablets and capsules can be manufactured as immediate release products or as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

For oral administration in liquid dosage form, the oral drug components are combined with any oral, non-toxic, pharmaceutically acceptable inert carrier such as ethanol, glycerol, water, and the like. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents.

Liquid dosage forms for oral administration can contain coloring and flavoring to increase patient acceptance. In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Sustained release liquid dosage forms suitable for parenteral administration, including, but not limited to, water-in-oil and oil-in-water microemulsions and biodegradable microsphere polymers, may be used according to methods well-known to those having ordinary skill in the art. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol. Suitable pharmaceutical carriers are described in Remington's Pharmaceutical Sciences, Mack Publishing Company, a standard reference text in this field. Solubilizing agents may be used to enhance solubility of the compounds of the subject invention in the liquid dosage form. Suitable solubilizing agents include, but are not limited to, amines, amino alcohols, amino sugars, and amino acids, such as glycine, histidine, and lysine.

The compounds of the instant invention may also be administered in intranasal form via use of suitable intranasal vehicles, or via transdermal routes, using those forms of transdermal skin patches well known to those of ordinary skill in that art. To be administered in the form of a transdermal delivery system, the dosage administration will generally be continuous rather than intermittent throughout the dosage regimen.

Parenteral and intravenous forms may also include minerals and other materials to make them compatible with the type of injection or delivery system chosen.

The compounds and compositions of the invention can be coated onto stents for temporary or permanent implantation into the cardiovascular system of a subject.

The compounds and compositions of the subject invention, like curcumin and other curcumin analogues, are useful for treating rheumatoid arthritis (RA), osteoarthritis (OA), metastases, periodontal disease, such as periodontitis, angiogenesis, emphysema, acute respiratory distress syndrome, multiple sclerosis, cardiovascular disease, such as atherosclerosis, myocardial infarction, arterial restenosis after angioplasty and aneurysm development; inflammatory disorders, including neuroinflammation and inflammatory bowel disease; many types of cancer, including breast cancer, skin cancer, including, but not limited to, melanoma, and prostate cancer; diabetes, stroke, peripheral neuropathy, brain trauma, and pancreatitis; bone diseases including, but not limited to, osteoperosis.

Curcumin has been known to be useful in the treatment of skin disorders, including, but not limited to, wounds, psoriasis, acne, burns, eczema, as well as inflammation accompanying such disorders (20-24). Singer and co-workers have shown that curcumin reduces burn progression in rats (21) and Sidhu and co-workers have shown curcumin to be effective in enhancing wound healing in animals (22), including streptozoticin-induced diabetic rats and genetically diabetic mice (23). In addition, Phan and co-workers have shown that curcumin exhibits powerful inhibition against hydrogen peroxide damage in human keratinocytes and fibroblasts (24). Accordingly, the improved compounds and compositions of the subject invention are useful for the treatment of skin disorders, including, but not limited to, wounds, including ulcers of the skin, and inflammatory diseases of the skin.

Variations on the following general synthetic methods will be readily apparent to those skilled in the art and are deemed to be within the scope of the present invention (47).

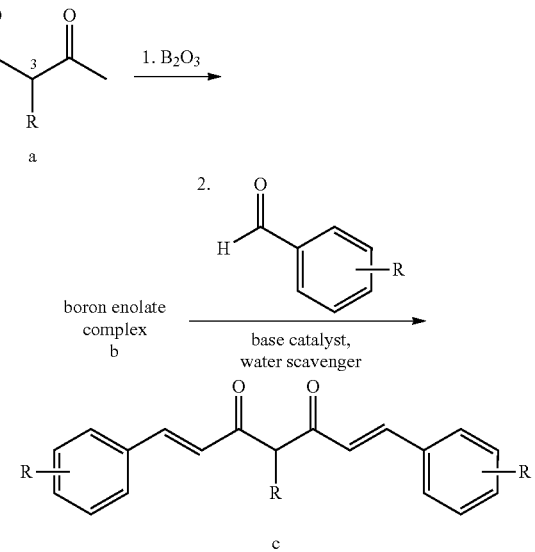

Scheme 1. Synthesis of curcumin analogues.

The synthesis of the curcumin analogues of the present invention can be carried out according to general scheme 1. The R groups designate any number of generic substituents.

The starting material is provided by 2,4-pentanedione, which is substituted at the 3-carbon (see compound a). The desired substituted 2,4-pentanedione may be purchased from commercial sources or it may be synthesized using conventional functional group transformations well-known in the chemical arts, for example, those set forth in Organic Synthesis, Michael B. Smith, (McGraw-Hill) Second ed. (2001) and March's Advanced Organic Chemistry: Reactions, Mechanisms, and Structure, Michael B. Smith and Jerry March, (Wiley) Sixth ed. (2007), and specifically by Bingham and Tyman (45) and in the case of 3-aryl-aminocarbonyl compounds by Dieckman, Hoppe and Stein (46), the contents of which are hereby incorporated by reference. 2,4-pentanedione a is reacted with boron trioxide to form boron enolate complex b.

Boron enolate complex b is a complex formed by coordination of the enolate of compound a with boron. It is understood by those having ordinary skill in the art that the number of compound a enolates that may coordinate to boron as well as the coordination mode, ie. monodentate versus bidentate, are variable so long as reaction, such as Knoevenagel condensation, at the C-3 carbon of the 2,4-pentanedione is suppressed.

Boron enolate complex b is then exposed to a benzaldehyde compound in the presence of a base catalyst and a water scavenger to form curcumin analogue c via aldol condensation. The ordinarily skilled artisan will appreciate that the benzaldehyde may possess various substituents on the phenyl ring so long as reactivity at the aldehyde position is not hindered. Substituted benzaldehyde compounds may be purchased from commercial sources or readily synthesized using aryl substitution chemistry that is well-known in the art. Suitable base catalysts for the aldol step include, but are not limited to, secondary amines, such as n-butylamine and n-butylamine acetate, and tertiary amines. Suitable water scavengers include, but are not limited to, alkyl borates, such as trimethyl borate, alkyl phosphates, and mixtures thereof. Other suitable reaction parameters have also been described by Krackov and Bellis in U.S. Pat. No. 5,679,864, the content of which is hereby incorporated by reference.

All combinations of the various elements described herein are within the scope of the invention.

Herein, where chemical substituents are disclosed in the alternative, it is intended that each such substituent can be used or combined with one or more other substituents disclosed in the alternative.

This invention will be better understood by reference to the Experimental Details which follow, but those skilled in the art will readily appreciate that the specific experiments detailed are only illustrative of the invention as described more fully in the claims which follow thereafter.

EXPERIMENTAL DETAILS

General Procedure for the Synthesis of Chemically-Modified Curcumins:

Boron oxide (0.49 g, 7 mmol, 0.7 eq.) and 3-methoxycarbonyl-pentane-2,4-dione (45) (1.58 g, 10 mmol, 1.0 eq.) for in the cases of compounds 11, 12 and 13, 10 mmol. of 3-(N-phenylaminocarbonyl)pentane-2,4-dione (46)} were placed in a 50 mL flask and the mixture was heated to 90° C. for 5 min to form a pale-yellow glass. The selected aromatic aldehyde (20 mmol, 2.0 eq.) and trimethyl borate (4.16 g, 40 mmol, 4.0 eq.) were dissolved in dry ethyl acetate (10 mL) and gradually added to the flask (3 min). with magnetic stirring. Then butylamine (0.05 mL) and butylammonium acetate in dimethylformamide solution (0.2 mL; 0.136 g/mL) were added. After about 1 hour, a precipitate began to form and stirring was continued at room temperature for 48 hours. The reddish precipitate was removed by filtration, washed with diethyl ether (5 mL). then dissolved in methanol (50 mL) and boiled for 30 min during which time the color became much lighter. Methanol was then removed by rotary-evaporation and the crude product was purified by crystallization from dichloromethane (20 mL) and methanol (20 mL).

Example 1

Preparation of 1,7-Bis(4-hydroxy-3-methoxyphenyl)-4-methoxycarbonylhepta-1E,6E-dien-3,5-dione (1)

A mixture of boron trioxide ($B_2O_3$: 1.5 g) and 3-methoxycarbonylpentan-2,4-dione (2.5 g) were fused at 120° C. until a homogeneous melt was formed (3 min). 3-methoxycarbonylpentan-2,4-dione can be synthesized using known methods (25, 26). For example, reaction of 3-acetylthiotetronic acid, which is synthesized by a known method (25), with methanol yields 3-methoxycarbonylpentan-2,4-dione (26). To the homogenous melt, there was then added a solution of trimethyl borate (6.0 g) and vanillin (4.5 g) in ethyl acetate (15 mL) followed by butylamine acetate (0.068 g) in dimethylformamide solution (0.5 mL) followed by 2 drops (Pasteur pipet) of butylamine. The mixture, when stirred, quickly became homogeneous and after three hours began to form a red precipitate, which was complete after standing for 24 h. The solution was filtered and the solid (7.5 g) that was collected was washed with ether, dried, and added to methanol (60 mL). This mixture was boiled gently for three hours with slow distillation then concentrated to 30 mL when the product, compound 2, (4.4 g) crystallized spontaneously. Melting point (mp): 178-179° C. Concentration of the mother liquors gave a second crop (0.3 g) of identical mp. Total yield, 73.6% based on vanillin. Mass spectrum m/e: Found 426.01; Calcd. 426.25. 1H NMR $CDCl_3$: Significant peaks δ 3.944 (s. 3H, $OCH_3$), 3.952 (s, 6H $OCH_3$), 5.89 (s, 2H, O$\underline{H}$) 18.3 (S, 1H, $\underline{H}$ at C4). Aromatic and ethylenic protons 6.9-7.3 (12H) as expected.

Chemically-modified curcumins possessing an electron-withdrawing group at the C-4 carbon are demonstrated to have improved inhibition of MMP activity, inhibition of NFκB activation, and inhibition of pro-inflammatory cytokine production.

The following compounds were made according to the general procedure described hereinabove.

1,7-Bis(4-hydroxy-3-methoxyphenyl)-4-methoxycarbonylhepta-1E,6E-dien-3,5-dione (1): 72.0% yield. mp 175-176° C. Mass spectrum m/e 425.1 (M−1)$^+$; Calcd. 426.0. $^1$H NMR ($CDCl_3$): Significant peaks 3.880 (s. 6H, aromatic $OCH_3$) 3.760 (s. 3H, ester $OCH_3$), 17.960 (s. 1H, H at C4). Aromatic and ethylenic protons 7.3-8.8 (10H).

1,7-Bis(4-hydroxyphenyl)-4-methoxycarbonylhepta-1E,6E-dien-3,5-dione (3): 49.2% yield. mp 214-216° C. Mass spectrum m/e: 365.0 (M−1)$^+$; Calcd. 365.1. $^1$H NMR ($CDCl_3$): Significant peaks 3.777 (s. 3H, $OCH_3$), 18.164 (s. 1H, H at C4), 9.320 (s. 2H, OH). Aromatic and ethylenic protons 6.8-7.7 (12H).

1,7-Bis(4-hydroxy-3-methoxyphenyl)-4-N-phenylaminocarbonylhepta-1E,6E-dien-3,5-dione (6): 11.0% yield. mp 193-194° C. Mass spectrum m/e: 486.2 (M−1)$^+$; Calcd. 486.1. $^1$H NMR (DMSO-$d_6$): Significant peaks 17.570 (s. 1H, H at C4), 10.580 (s. H, NH), 9.777 (s. 2H, OH), 3.701 (s. 6H, $OCH_3$). Aromatic and ethylenic protons 6.7-7.8 (10H).

1,7-Bis(4-hydroxyphenyl)-4-N-phenylaminocarbonyl-hepta-1E,6E-dien-3,5-dione (7): 10.2% yield. mp 220-221° C. Mass spectrum m/e: 426.2 (M−1)$^+$; Calcd. 426.1. $^1$H NMR (DMSO-$d_6$): Significant peaks 17.561 (s. 1H, H at C4), 10.609 (s. H, NH), 10.159 (s. 2H, OH). Aromatic and ethylenic protons 6.7-7.8 (12H).

1,7-Bis(4-dimethylaminophenyl)-4-N-phenylaminocarbonylhepta-1E,6E-dien-3,5-dione (8): 26.8% yield. mp 208-209° C. Mass spectrum m/e: 480.3 (M−1)$^+$; Calcd. 480.4. $^1$H NMR (DMSO-$d_6$): Significant peaks 17.773 (s. 1H, H at C4), 10.556 (s. H, NH), 2.959 (s. 12H, N(CH$_3$)$_2$). Aromatic and ethylenic protons 6.7-7.8 (12H).

1,7-Bis(3-pyridyl)-4-methoxycarbonylhepta-1E,6E-dien-3,5-dione (9): 38.7% yield mp. 195-196'C. Mass spectrum m/e: 335.69 (M−1)$^+$; Calcd. 335.01. $^1$H NMR (CDCl$_3$): Significant peaks 3.960 (s. 3H, OCH$_3$), 18.050 (s. 1H, H at C4). Aromatic and ethylenic protons 7.0-8.6 (12H).

1,7-Bis(2-hydroxyphenyl)-4-methoxycarbonylhepta-1E,6E-dien-3,5-dione (10): 46.3% yield. mp 165-166° C. Mass spectrum m/e: 365.1 (M−1)$^+$; Calcd. 365.1. $^1$H NMR (CDCl$_3$): Significant peaks 3.610 (s. 3H, OCH$_3$), 17.980 (s. 1H, H at C4), 9.420 (s. 2H, OH). Aromatic and ethylenic protons 6.4-7.9 (12H).

1,7-Bis(3-hydroxyphenyl)-4-methoxycarbonylhepta-1E,6E-dien-3,5-dione (11): 20.2% yield. mp 188-189° C. Mass spectrum m/e: 365.1 (M−1)$^+$; Calcd. 365.1. $^1$H NMR (CDCl$_3$): Significant peaks 3.851 (s. 3H, OCH$_3$), 18.010 (s. 1H, H at C4), 8.890 (s. 2H, OH). Aromatic and ethylenic protons 6.7-7.7 (12H).

1,7-Bis(3-nitro-4-hydroxy-5-methoxyphenyl)-4-methoxycarbonylhepta-1E,6E-dien-3,5-dione (12): 26.0% yield. mp N/A. Mass spectrum m/e: 515.2 (M−1)$^+$; Calcd. 515.1. $^1$H NMR (CDCl$_3$): Significant peaks 3.873 (s. 3H, OCH$_3$), 18.056 (s. 1H, H at C4), 11.010 (s. 2H, OH). Aromatic and ethylenic protons 7.3-8.8 (8H).

1,7-Bis(4-hydroxy-3,5-dimethoxyphenyl)-4-methoxycarbonylhepta-1E,6E-dien-3,5-dione (13): 77.0% yield. mp 179-180° C. Mass spectrum m/e: 485.2 (M−1)$^+$; Calcd. 485.0. $^1$H NMR CDCl$_3$: Significant peaks 3.925 (s. 3H, ester OCH$_3$), 3.948 (s. 12H, aromatic OCH$_3$), 18.336 (s. 1H, H at C4). Aromatic and ethylenic protons 6.8-7.8 (8H).

1,7-Bis(4-N,N-dimethylaminophenyl)-4-methoxycarbonylhepta-1E,6E-dien-3,5-dione (14): 45.1% yield. mp N/A. Mass spectrum m/e: 421.4 (M+1)$^+$; Calcd. 421.1. $^1$H NMR (CDCl$_3$): Significant peaks 3.938 (s. 3H, OCH$_3$), 18.486 (3.1H, H at C4), 3.028 (s. 12H, N(CH$_3$)$_2$). Aromatic and ethylenic protons 6.6-7.9 (12H).

1,7-Bis(2-hydroxy-3-methoxyphenyl)-4-methoxycarbonylhepta-1E,6E-dien-3,5-dione (15): 25.8% mp 201-202° C. Mass spectrum m/e: 427.4 (M+1)$^+$; Calcd. 426.0. $^1$H NMR (CDCl$_3$): Significant peaks 3.824 (s. 6H, aromatic OCH$_3$) 3.878 (s. 3H, ester OCH$_3$), 18.125 (s. 1H, H at C4), 9.609 (s. 2H, OH). Aromatic and ethylenic protons 6.8-8.1 (10H).

1,7-Bis(4-acetoxy-3-methoxyphenyl)-4-methoxycarbonylhepta-1E,6E-dien-3,5-dione (16): 46.0% mp 169-170° C. Mass spectrum m/e: 510.1 (M−1)$^+$; Calcd. 510.1. $^1$H NMR (CDCl$_3$): Significant peaks 3.610 (s. 3H, ester OCH$_3$), 3.869 (s. 6H, aromatic OCH$_3$), 18.175 (s. 1H, H at C4). Aromatic and ethylenic protons 7.0-7.9 (12H).

Mass spectral data are reported in negative- or positive-ion mode depending on the specific compound.

Example 2

Inhibition of MMPs

It has been observed that 50 and 100 μM concentrations of curcumin decreased TNFα production by endotoxin-stimulated human monocytes (HMs) in culture by 80-90% (lower concentrations of curcumin, 10 and 20 μM, had no effect). However, this inhibitory effect was associated with some precipitation of the curcumin in cell culture and with significant cytotoxicity. It was hypothesized that increasing the solubility of curcumin will: (i) enhance its efficacy as an inhibitor of cytokine expression, (ii) reduce its cytotoxicity, and (iii) preserve (perhaps even enhance; see below) its potency, as an MMP inhibitor (MMPI) compound, which was found to be similar to that of the Zn$^{++}$ chelating compound, 1,10-O-phenanthroline (FIG. 1). However, it should be noted that excessive inhibition of MMP activity may not be desirable therapeutically because a minimal, or basal, level of MMPs may be necessary for optimal defense of the host (27).

Two chemically-modified curcumins, compound 1 and 2, were generated with improved solubility and tested in vitro for their proteinase inhibitor potency (IC$_{50}$) and in a cell culture system for cytotoxicity and anti-inflammatory properties.

Table 1 shows the IC$_{50}$ of curcumin, compound 1, and compound 2, compared to a standard Zn$^{++}$ binding & MMPI (matrix metalloproteinase inhibitor), 1,10-O-phenanthroline (o-phen), against purified human PMN MMP-8 (from EMD biologics, Inc., Gibbstown, N.J.) using a synthetic octapeptide containing the collagenase-susceptible glycine-isoleucine peptide bond and measuring the tripeptide breakdown products by HPLC (Waters Alliance 2695 System with a reverse phase C-18 column). Compound 1 was an excellent MMPI with an IC$_{50}$ equivalent to that of 1,10-O-phenanthroline, while compound 2, which lacked substituents on the aryl moieties, did not show a dose response.

TABLE 1

| | MMP inhibition in vitro | |
|---|---|---|
| Compound | IC$_{50}$ against purified hMMP-8 | Ratio of each IC$_{50}$ to IC$_{50}$ of 1,10-O-phenanthroline |
| 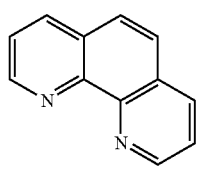<br>1,10-O-phenanthroline | 10-35 μM* | 1 = 35 μM<br>1 = 10 μM |

TABLE 1-continued

MMP inhibition in vitro

| Compound | IC$_{50}$ against purified hMMP-8 | Ratio of each IC$_{50}$ to IC$_{50}$ of 1,10-O-phenanthroline |
|---|---|---|
| 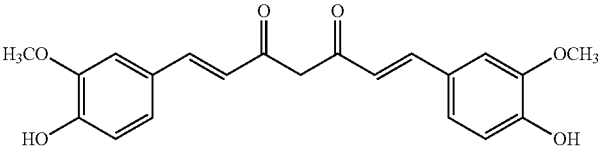 curcumin | 14 μM | 1.4 |
| 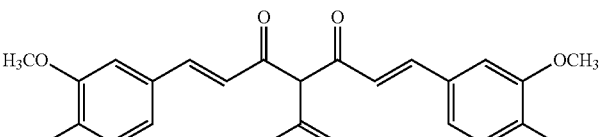 compound 1 | 35 μM | 1 |
| 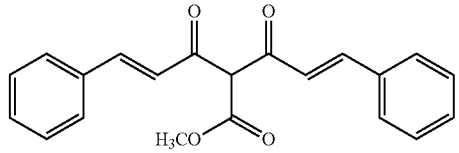 compound 2 | No dose response | — |
| 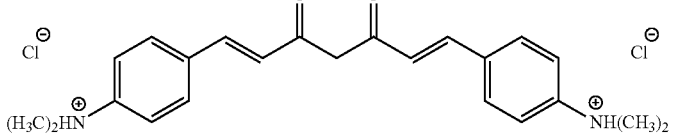 Compound 5 | 28 μM | 0.8 |

*in one experiment, the IC$_{50}$ for phenanthroline was 10 μM, in a second experiment the IC$_{50}$ for phenanthroline was 35 μM.

Example 3

The cytotoxicity of curcumin and compound 1 was compared to that of 1,10-O-phenanthroline in human monocytes. The results are summarized in table 2.

TABLE 2

Cytotoxicity in human monocytes

| Compound | Recovery from human serum | Cytotoxicity Monocytes @ 5 h incubation | Cytotoxicity Monocytes @ 18 h incubation | % Inhibition of MMP-9 in monocyte media |
|---|---|---|---|---|
| 1,10-O-phenanthroline | — | — | — | — |
| curcumin | 83-94% | 10 uM- 0% 20 uM- 20% 50 uM- 50% | 10 uM- 0% 20 uM- 20% 50 uM- 77% | nd |
| compound 1 | 76-80% | 2 uM- 0% 10 uM- 0% 25 uM- 33% | 2 uM- 0% 25 uM- 45.5% 50 uM- 53% | 2 uM +++++ 25 uM +++++ 50 uM +++++ |

Detection of compounds & extractability/recovery from human serum (for future use to determine in vivo pharmacokinetics) was achieved using HPLC. The HPLC detection method is briefly described herein. 50 μl of buffer or human serum containing 166.67 μM, 16.67 μM and 1.67 μM of the compounds were incubated with 100 μl pre-cooled (−10° C.) extraction solvent containing CAN-MeOH-0.5M oxalic acid at a ratio of 60:30:10. The mixture was vortexed and centrifuged at 10,000 rpm for 10 min. The supernatant was then aliquoted and injected into an HPLC for analysis. Stock solutions of the compounds were made 100× in DMSO, then further diluted with buffer or serum. Results show 83-94% recovery for curcumin, and 76-80% recovery for compound 1 (see table 2).

Example 4

Inhibition of Pro-Inflammatory Cytokine Production

Inhibition of pro-inflammatory cytokine production by compound 1 was examined. Briefly, human peripheral blood monocytes (HMs) were isolated from a leukocyte concentrate by density gradient centrifugation (Lymphoprep) and the isolated HMs cultured (2 h, 37° C.) to remove non-adherent cells. The adherent HMs were cultured for 18 h (1×10$^6$ cells/well, 24-well plates)±endotoxin (LPS)±different compounds dissolved in DMSO (the final concentration of DMSO in the RPMI serum-free culture media with Pen./Strep. antibiotics was no greater than 0.5%). After incubation, the proinflammatory cytokines, TNFα, IL-1β, MCP-1 and IL-6 were measured in the conditioned media by ELISA and cytotoxicity was assessed by measuring the absorbance (490 nm) of formazan produced by reduction of MTS. The HMs alone ±0.1-0.5% DMSO produced minimal levels of these pro-inflammatory cytokines. However, addition of 100 ng/ml or 10 µg/ml of LPS both dramatically stimulated cytokine production. Of the tested compounds, compound 1 stood out as having improved inhibition of proinflammatory cytokines when compared to curcumin. At 2 µM concentration, compound 1 showed no evidence of cytotoxicity (as shown on table 2), but inhibited cytokine production as follows: TNFα, IL-1β, MCP-1 and IL-6 were inhibited by 63%, 41%, 74% and 30% respectively (see table 3).

TABLE 3

Inhibition of cytokine production

| Compound | % Inhibition of TNF-α produced by stimulated Monocytes with LPS @ 18 h | % Inhibition of IL-1β produced by stimulated Monocytes with LPS @ 18 h | % Inhibition of MCP-1 produced by stimulated Monocytes with LPS @ 18 h | % Inhibition of IL-6 produced by stimulated Monocytes with LPS @ 18 h |
|---|---|---|---|---|
| 1,10-O-phenanthroline | — | — | — | — |
| curcumin | 10 uM- 0%<br>20 uM- 0%<br>50 uM- 80% | nd | nd | nd |
| compound 1 | 2 uM- 63%<br>25 uM- 100%<br>50 uM- 100% | 2 uM- 41%<br>25 uM- 100%<br>50 uM- 100% | 2 uM- 74%<br>25 uM- 78%<br>50 uM- 79% | 2 uM- 30%<br>25 uM- 100%<br>50 uM- 100% |

Figure 2:
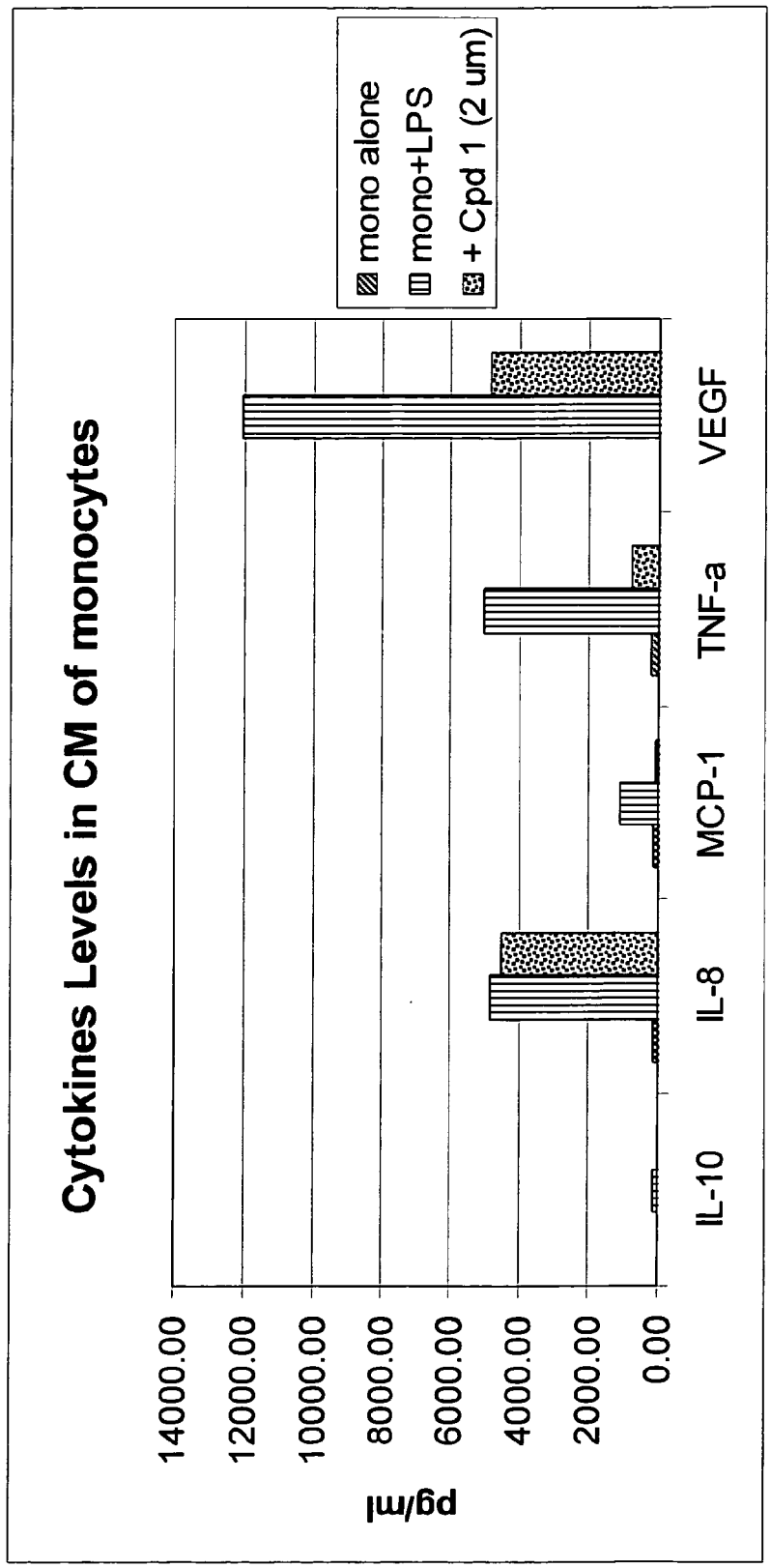
FIG. 2. Cytokine levels in conditioned media (CM) of monocytes: Effect of compound 1.

The cell culture experiment was repeated to confirm the improved proinflammatory cytokine inhibition activity of compound 1. FIG. 2 shows that compound 1 at 2 µM concentration was indeed potent in reducing proinflammatory cytokines such as MCP-1 and TNFα and growth factors such as VEGF in LPS-challenged human monocytes in culture. The cytokine levels were measured by Luminex multiplex, a method that allows the simultaneous measurement of different biological markers.

Example 5

Inhibition of NFκB Activation in Human Monocytes

The inhibition of NFκB activation by compound 1 was studied in human monocytes in cell culture. Compound 1 was examined at 2 µM and 10 µM concentration in the presence of 2 different activation stimuli, LPS endotoxin and CRP/oxid-LDL complex. It was observed that compound 1 inhibited both endotoxin-stimulated NFκB activation and CRP/oxid-LDL complex-stimulated NFκB activation (see table 4). Preliminary studies indicated that compound 1 had little/no effect on p38 MAP kinase activation.

TABLE 4

The effect of compound 1 on NFκB activation in human monocytes in cell culture.

| Activation stimulus | Concentration | % Inhibition |
|---|---|---|
| Endotoxin (LPS) | 2 µM | 24 |
|  | 10 µM | 85 |
| CRP/oxid-LDL | 2 µM | 91 |
| Complex | 10 µM | 100 |

Example 6

Development of a Rat Model of Type 1 Diabetes

A rat model of type I diabetes was developed to test the efficacy of the compounds of the subject invention in vivo. This animal model is characterized, in part, by excessive MMP activity, collagen breakdown, and proinflammatory cytokine expression. In a previous drug development program, resulting in two FDA-approved systemically-administered (by the oral route) drugs currently on the market (in the U.S. and Europe for one, and in the U.S., Canada, and Europe for the other), this rat model proved very effective for testing efficacy and pharmacokinetics (e.g., serum half-life) in vivo and produced results consistent with those from our in vitro and cell culture studies (4, 28, 29).

A well-established model of diabetes induction in Sprague-Dawley rats with and without the additional induction of periodontal disease is to be utilized to investigate the mechanism underlying the association between diabetes and bone loss in periodontal disease (30-41).

DLAR was used for both housing and experimental manipulations to allow close monitoring of treated animals and provide immediate access to analgesia or euthanasia as required. Rats were allowed to aclimate to the facility for at least three days prior to experimental use. All laboratory and animal care personnel were trained in the proper manipulation and care of rats.

Investigational focus includes three general areas: (I) the effect of matrix metalloproteinases (MMPs) in the tissue destruction and immune responses related to inflammation, (II) the effect of prophylactic and/or therapeutic treatment by administration of the compounds on matrix mettalloproteinases (MMPs) in the tissue destruction and immune responses related to (a) periodontal inflammation and bone loss, (b) systemic changes in MMP activity or levels in circulation, (c) skin atrophy reflecting MMP-mediated connective tissue degradation, and (III) the pharmacokinetics of relevant curcumin analogues having an electron-withdrawing group at the C-4 carbon in this rat model of inflammation and tissue destruction.

The purpose of the following was to establish an in vivo model of excessive collagen degradation to be used to test efficacy of the compounds of the subject invention. Male Sprague-Dawley rats (typically 300-400 gms of body weight), specific viral antibody free, were ordered from Charles River. Following general anesthesia via isoflurane anesthetic inhalation, diabetes was induced by an I.V. administration of streptozotocin (STZ) (50* mg/kg body weight) (Sigma Chemical Co., St Louis, Mo., USA) diluted in 0.9% citrated saline (pH 4.5), after 12 hours of fasting. After the streptozotocin injection, the animals were given free access to water and food. Diabetic status were confirmed weekly using a glucose test strip (Tes-Tape, Eli Lilly), which revealed >2% glucose in the urine of the STZ-injected animals within the first 24-48 hours after injection of streptozotocin. In this test, the test-paper color changes to dark brown which indicates glycosuria. During the experimental period, as expected, all the diabetic rats demonstrated polydipsia (excessive drinking), polyphagia (excessive eating), polyuria (excessive urination), loss of body weight, and hyperglycemia.

A 25% mortality rate is observed after a single injection of a dose of up to 70 mg/kg body weight of streptozotocin. This mortality rate has been taken into account when determining the number of rats required per experimental groups. Normal control animals are inoculated with an equivalent volume of citrate buffer using the same route as the diabetes induced animals.

On day 21, animals were euthanized via $CO_2$ inhalation. Blood samples were collected by cardiac puncture into vacutainer tubes containing liquaemin sodium citrate (Liquemine, La Roche Ltd, Basel Switerland). After centrifugation, plasma was separated and aliquoted and stored at $-80°$ C. for future analysis. A plasma glucose level of greater than 300 mg/dl confirmed the presence of diabetes.

Gingival samples were collected and pooled from each group for extraction, followed by partial purification and analysis of collagenase and gelatinase in the extracts. Spleen, heart, and salivary glands were removed for either histological evaluation, phenotypes of lymphocytic cells, analysis of cytokine/chemokine expression. Dorsal skin biopsy about 2×2 inches were collected and immediately frozen at in $-80°$ C. for collagen content and solubility analysis. All the tissues were frozen in $-80°$ C., and the biochemical analysis are pursued in due course. Both upper and lower jaws were removed defleshed and stained for morphometric analysis of bone loss under a dissecting microscope (20×). In future experiments, loss of bone volume may be assessed by micro CT scan.

Figure 3:
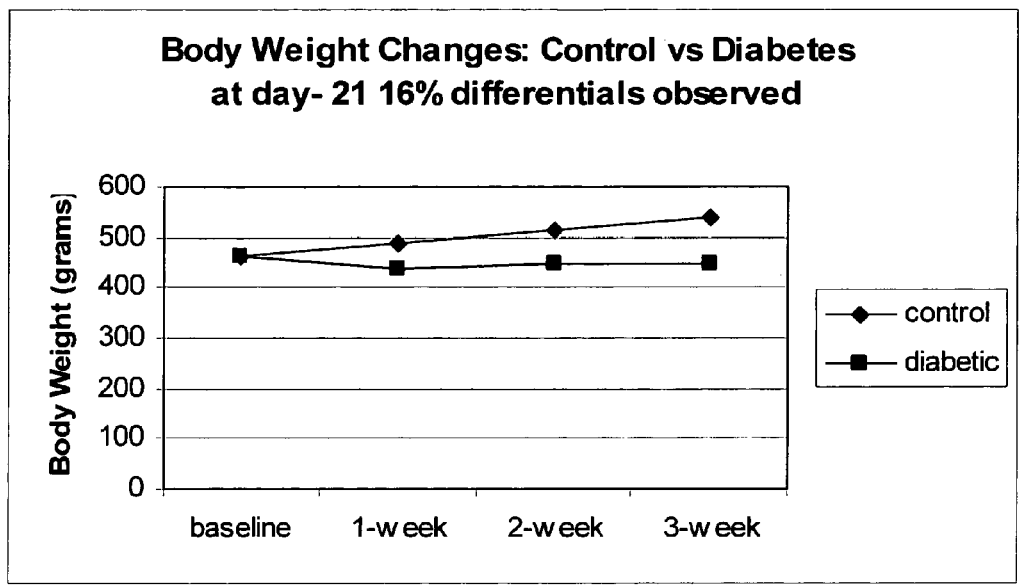
FIG. 3. Development of type 1 diabetes rat model. Body weight changes: control vs. diabetes at day 21. 16% differential observed at 3 weeks.
Figure 4:
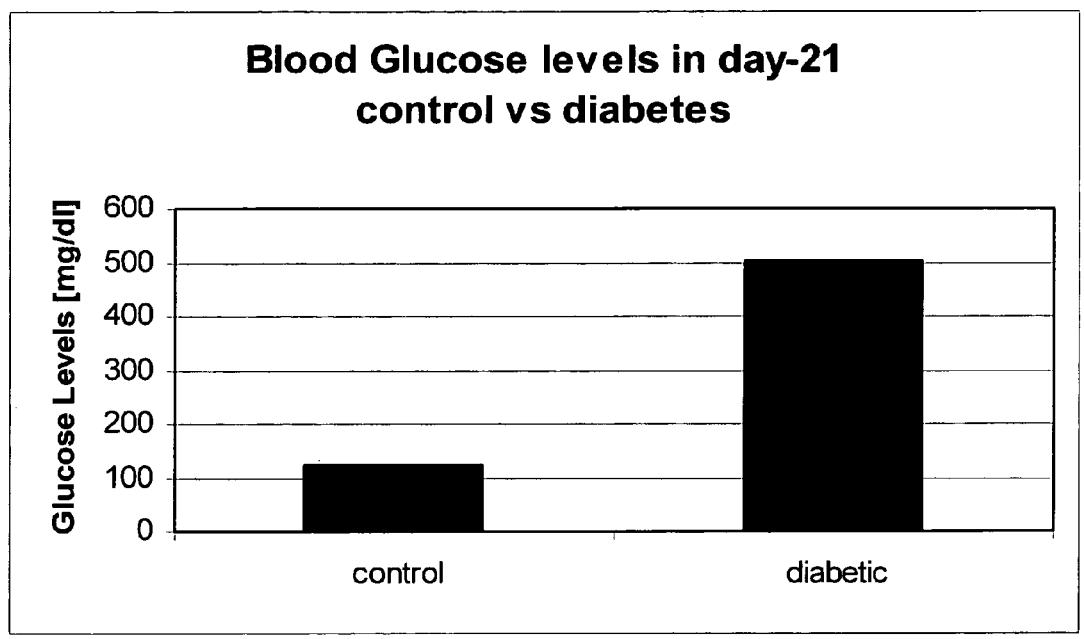
FIG. 4. Blood glucose levels at day 21: control vs. diabetes.

5 controls and 8 diabetic rats (after a single i.v. injection of streptozotocin at 50 mg/kg body weight) were sacrificed on day 21. Body weight and blood glucose levels were analyzed and results are shown in FIGS. 3 and 4.

The effect of matrix metalloproteinases (MMPs) in the tissue destruction and immune responses related to periodontal inflammation, the effect of prophylactic and/or therapeutic treatment on matrix metalloproteinases (MMPs) in the tissue destruction and immune responses related to periodontal inflammation and bone loss, as well as other tissue responses, and the pharmacokinetics of are examined by administration of relevant curcumin analogues having an electron-withdrawing group at the C-4 carbon in this rat model of inflammation and correlating the observed changes.

Example 7

In Vitro Inhibition of MMP-8

Using the same experimental conditions described in Example 2, results indicated that compound 3 (Table 5), another curcumin derivative, is more potent as a collagenase or MMP inhibitor than compound 1. As described hereinabove, compound 1 (a methoxycarbonyl curcumin) was equal in potency to 1,10-phenthroline (a zinc chelator typically used to block collagenase activity assays in vitro; phenanthroline is a toxic compound not suitable for use in vivo) as an inhibitor of human collagenase, and more potent than natural curcumin in vitro. Moreover, compound 3 is more soluble in aqueous solutions than compound 1 which, in turn, is more soluble than the insoluble natural product curcumin.

TABLE 5

Structure of Compounds 3 and 4.

Compound Structure

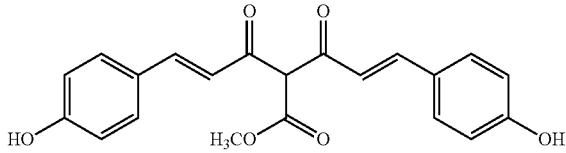 [SMILES: COC(=O)C(C(=O)/C=C/c1ccc(O)cc1)C(=O)/C=C/c1ccc(O)cc1]

Compound 3

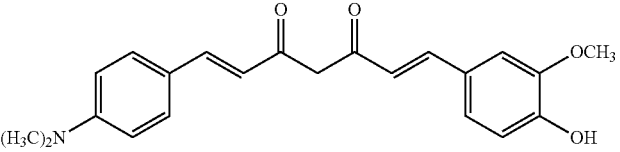

Compound 4

Figure 5:
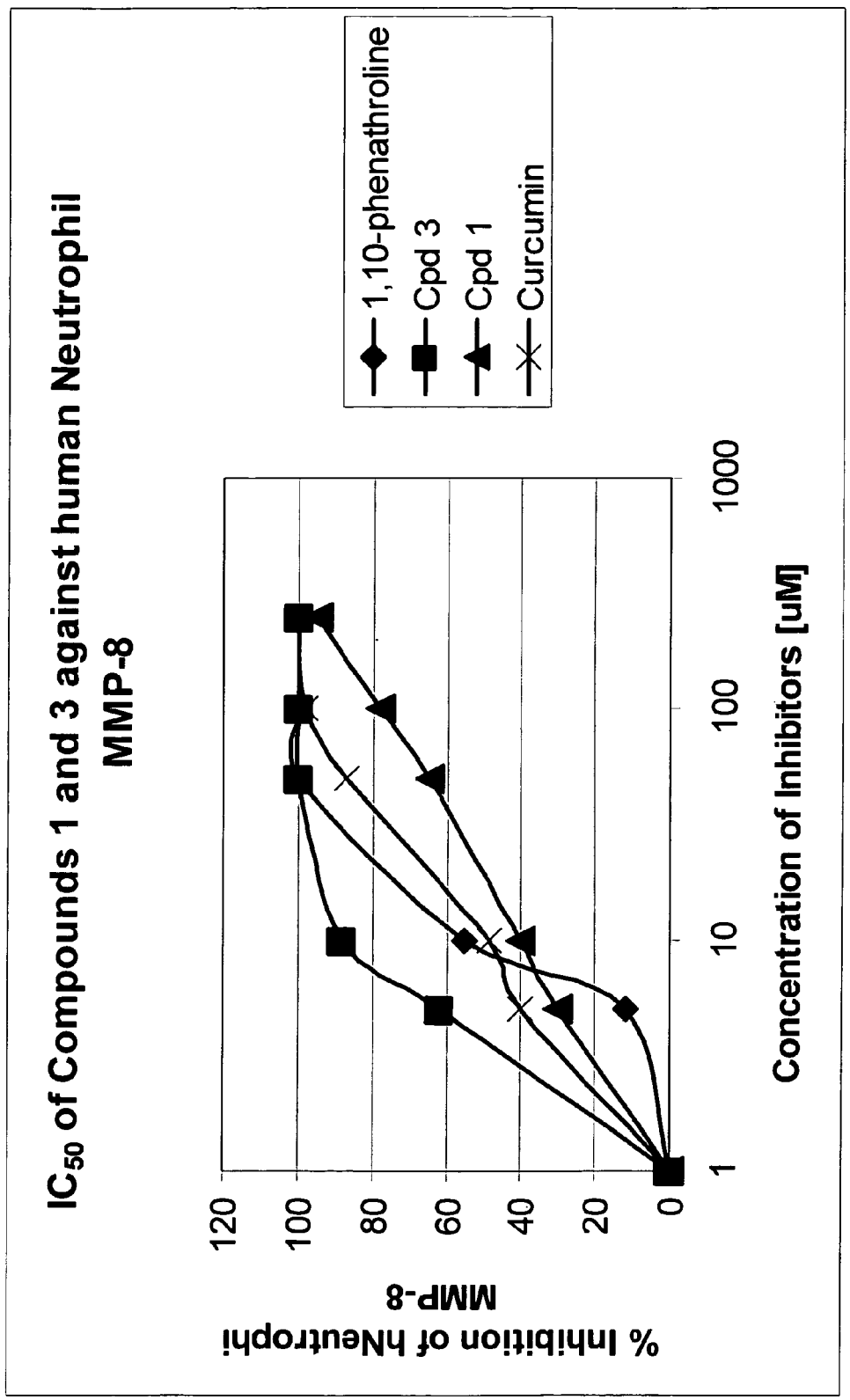
FIG. 5. A comparison of the MMP-8 inhibitory potency ($IC_{50}$) of several curcumin compounds & 1,10-phenanthroline.

Using the same technique as in Example 2, the synthetic octapeptide substrate, containing the collagenase-susceptible glycine-isoleucine peptide bond, was incubated (37° C.) with commercially-available chromatrographically-purified human neutrophil collagenase (MMP-8) in the presence of 1 mM $Ca^{++}$ and the tripeptide degradation fragment and undegraded substrate were separated and measured by HPLC. Compound 3 was added at different final concentrations ranging from 5-500 μM and the % inhibition of the collagenase activity was calculated. In this experiment, compound 3 was found to inhibit 50% of the collagenase activity ($IC_{50} \leq 5$ μM) at about half the concentration required for compound 1 ($IC_{50}=10$ μM) (FIG. 5).

Example 8

In Vitro Inhibition of MMP-9

Figure 6:
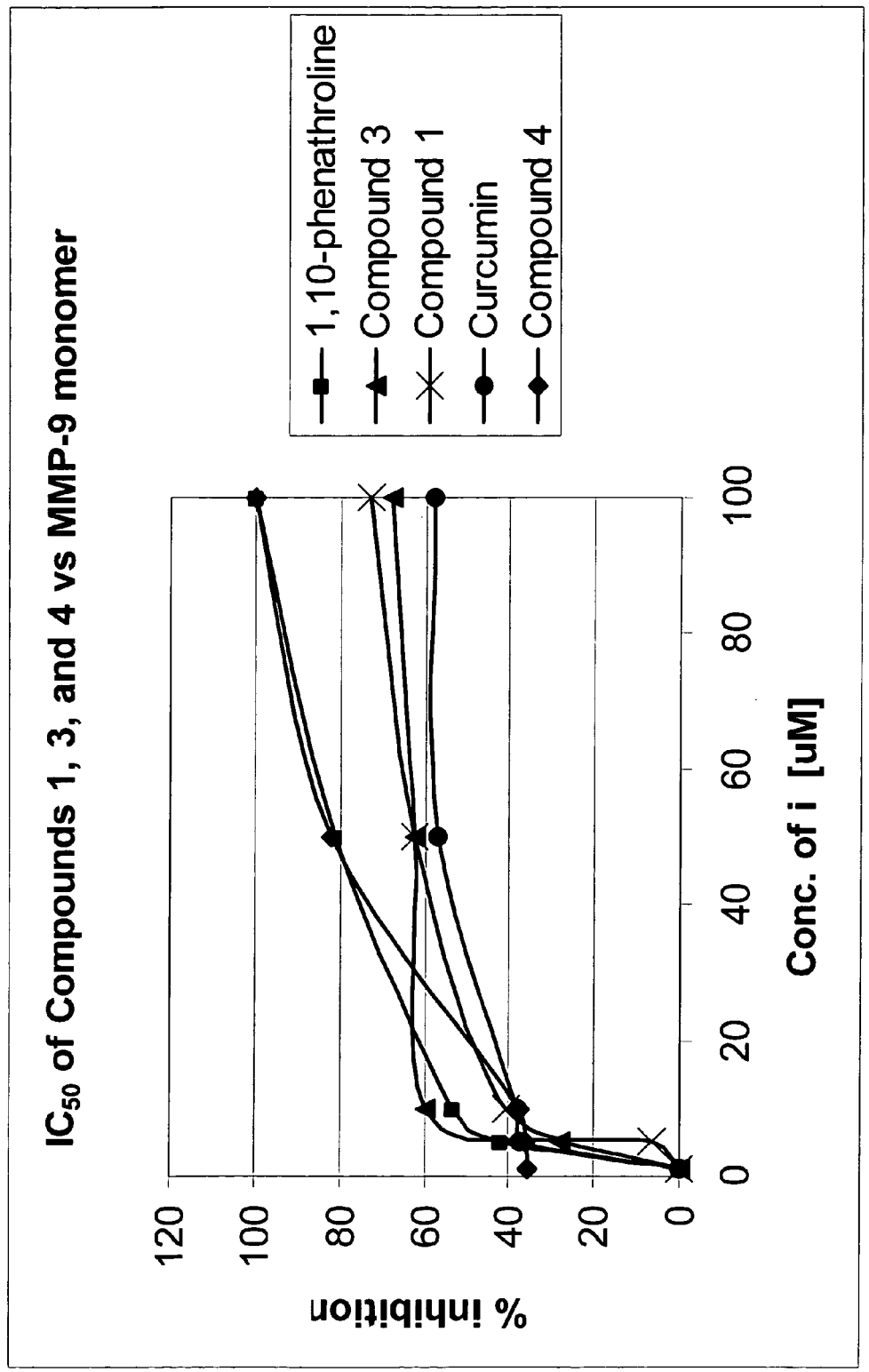
FIG. 6. A comparison of the MMP-9 Inhibitory Potency ($IC_{50}$) of several chemically-modified curcumins and 1,10-phenanthroline FIG. 7. Effect of compound 1 on blood glucose and MMPs. Diabetes increases MMP-2 & MMP-9 in rat plasma. * "Low-dose" reflects low serum concentration (~0.1 μg/ml) and short duration (1 week treatment); NDC=non-diabetic Control (n=4 rats/group); UD=Untreated Diabetic (n=6 rats/group); D+compound 1=Diabetic treated with compound 1 (n=6 rats/group).

The ability of 1,10-phenanthroline, curcumin, compound 1, compound 3, and compound 4 (see Table 5) to inhibit a different MMP, 92 kDa gelatinase or MMP-9, under the same experimental conditions described hereinabove for human leukocyte collagenase (MMP-8) was investigated. Once again compound 3 showed the lowest $IC_{50}$ (6 μM) as an MMP inhibitor, this time against MMP-9 (human leukocyte gelatinase), and again had a lower $IC_{50}$ than 1,10-phenanthroline (9 μM). All three chemically-modified curcumins, compound 1, compound 4 and compound 3, again showed lower $IC_{50}$ values (6-17 μM) than the natural curcumin ($IC_{50}=29$ μM) and the latter compound, even at a very high concentration (100 μM) was only able to inhibit degradation of the gelatinase substrate by 58%. In contrast all three chemically-modified curcumins at 100 μm final concentration inhibited gelatinase activity by 68-100% (FIG. 6 and Table 6).

TABLE 6

Potency of Chemically-Modified Curcumins as MMP-9 Inhibitors

| Test compounds | IC$_{50}$ (μM) | Maximum Inhibition At 100 μM compound |
|---|---|---|
| 1,10-phenanthroline | 9 | 100% |
| Curcumin | 29 | 58% |
| Compound 1 | 16 | 72% |
| Compound 4 | 17 | 100% |
| Compound 3 | 6 | 68% |

Example 9

Evaluation of Compound 1 In Vivo

Figure 7:
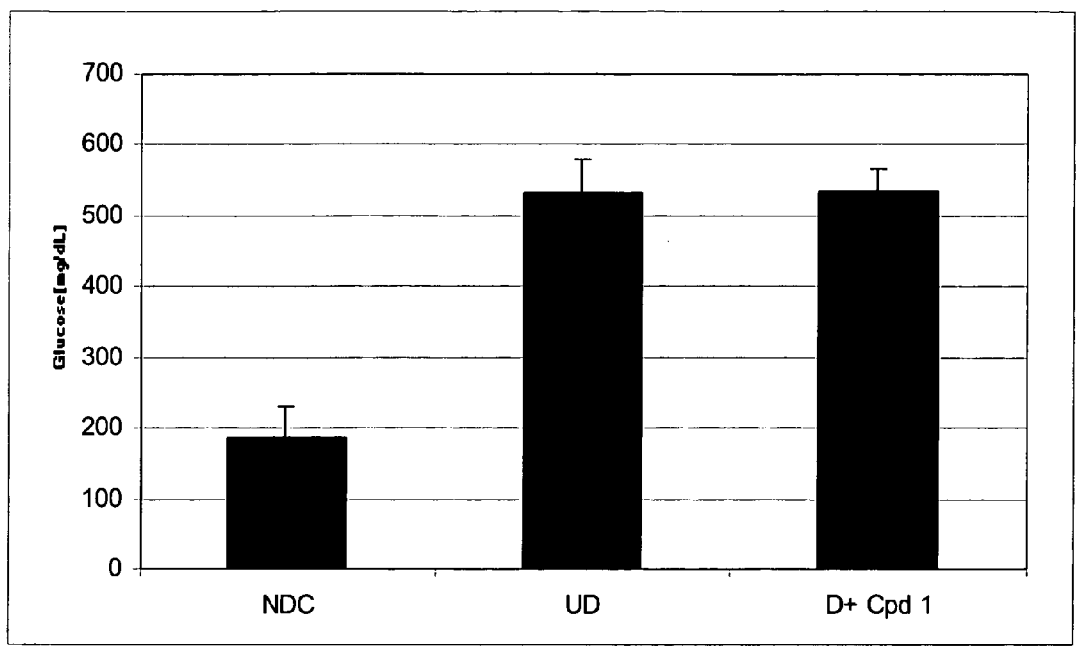
Figure 7:
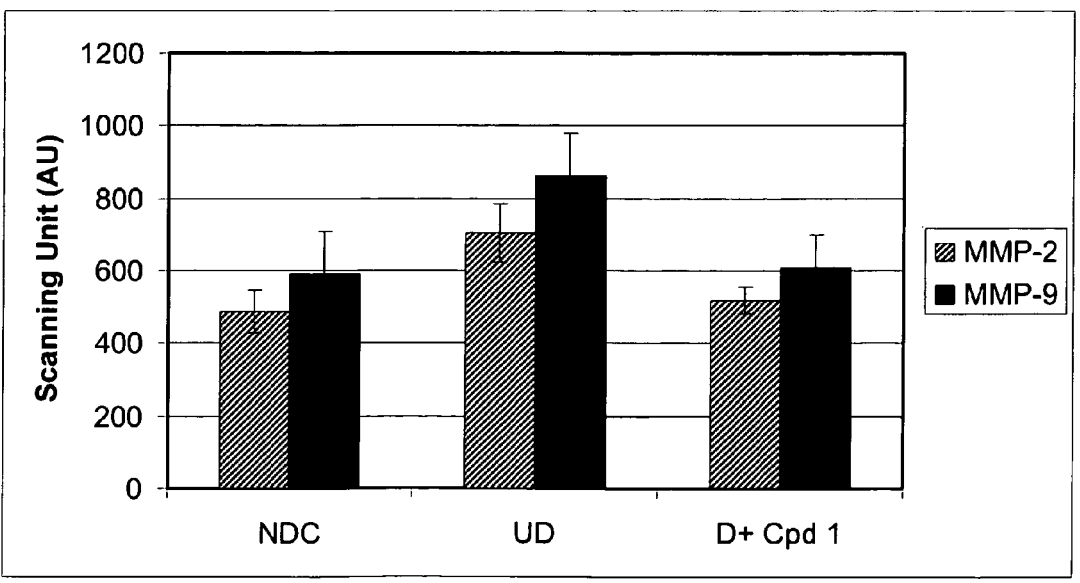
Figure 8:
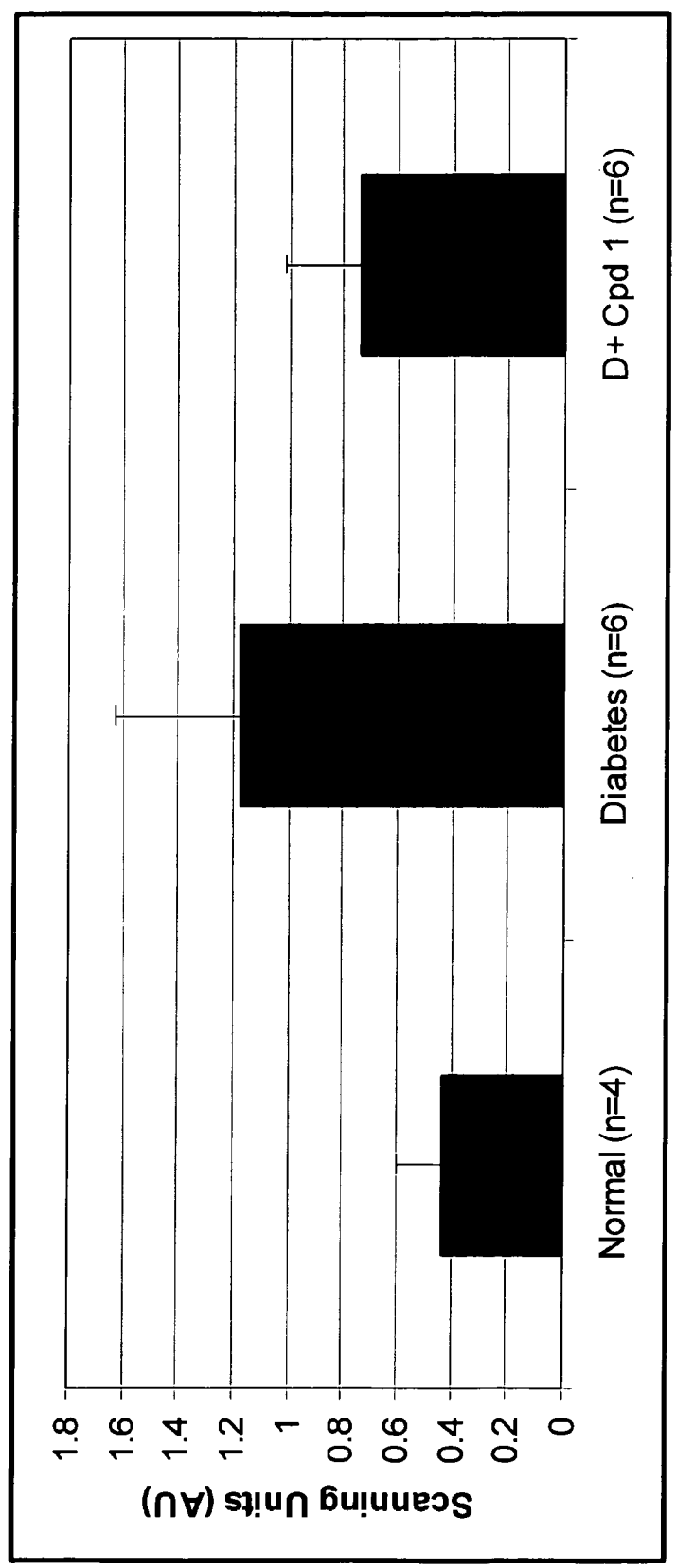
FIG. 8. MMP-8 levels, assessed by Western blots, in partially purified rat skin extract.

Compound 1 (methoxycarbonyl curcumin) was further investigated in vivo in the insulin-deficient diabetic rat model, described in Example 6. In one study, 16 male Sprague-Dawley rats (about 375 g body wt.) were distributed into three experimental groups: non-diabetic controls (NDC group; n=4 rats); rats rendered diabetic by streptozotocin injection (70 mg/kg) then, 2 week later, administered vehicle (carboxymethyl cellulose) alone once/day by oral gavage for 7 days (UD group; n=6); and diabetics administered orally once/day for 7 days Compound 1 (100 mg/kg) suspended in the vehicle (D+Compound 1; n=6). As expected, the diabetic rats were severely hyperglycemic compared to the NDC group (>500 mg/dl serum glucose vs. <200 mg/dl) and the oral administration of compound 1 to the diabetics had no effect on the severity of hyperglycemia (FIG. 7A). However, when the plasma gelatinase levels were examined by gelatin zymography, and the lytic zones measured by densitometric analysis, both MMP-2 (72 kDa gelatinase or gelatinaseA) and MMP-9 (92 kDa gelatinase or gelatinase B) were elevated in the UD rats compared to the NDCs, and oral administration of compound 1 reduced the excessive levels of MMPs to essentially normal levels (FIG. 7B) in spite of continuing severe hyperglycemia (FIG. 7A). A similar pattern was observed for collagenase-2 (MMP-8) in extracts of skin samples from the three groups, NDC, UD and D+Compound 1 (FIG. 8). The latter assays were carried out using Western blot analysis with monoclonal antibodies to MMP-8.

Also of interest in this short-term treatment experiment (2 weeks diabetes with no treatment, followed by 1-week of oral treatment with compound 1), the diabetic adverse events (AE) (Table 7) seemed to parallel the changes, described above, in plasma and skin. The UD rats showed the greatest incidence & severity of AEs and treatment with compound 1 appeared to reduce them (Table 7).

TABLE 7

Diabetic Adverse Events: Effect of Compound 1

| Experimental Group (no. of rats per group) | Incidence of Adverse Events (AEs) | Description of AEs |
|---|---|---|
| NDC (n = 4) | 0/4 | None |
| UD (n = 6) | 3/6 | Bleeding from nose and under nails; inflamed sclera; excessive tears |
| D plus compound 1 (n = 6) | 1/6 | Minor inflamed sclera |

Example 10

Evaluation of Compound 1 In Vivo

In a second in vivo study testing orally administered compound 1, four groups of rats (6 rats/group) were established including non-diabetic controls (NDC group), diabetics orally administered vehicle (carboxymethyl cellulose) alone once/day for 3-weeks, and diabetics orally administered a lower (100 mg/g) or higher (500 mg/kg) oral dose of compound 1 daily over the 3-week time period. At the end of the treatment protocol, the rats were sacrificed, blood samples were collected, and whole skin (except over limbs) and gingiva were dissected (the skin, because of ample quantities of tissue were analyzed for each rat separately; the gingiva, because of the tiny amounts that could be harvested per rat, were pooled for each experimental group, as prescribed previously for tetracycline studies (30). In addition, the jaw bones were collected, defleshed, and bone loss around the teeth analyzed morphometrically as described previously (42, 43).

Figure 9:
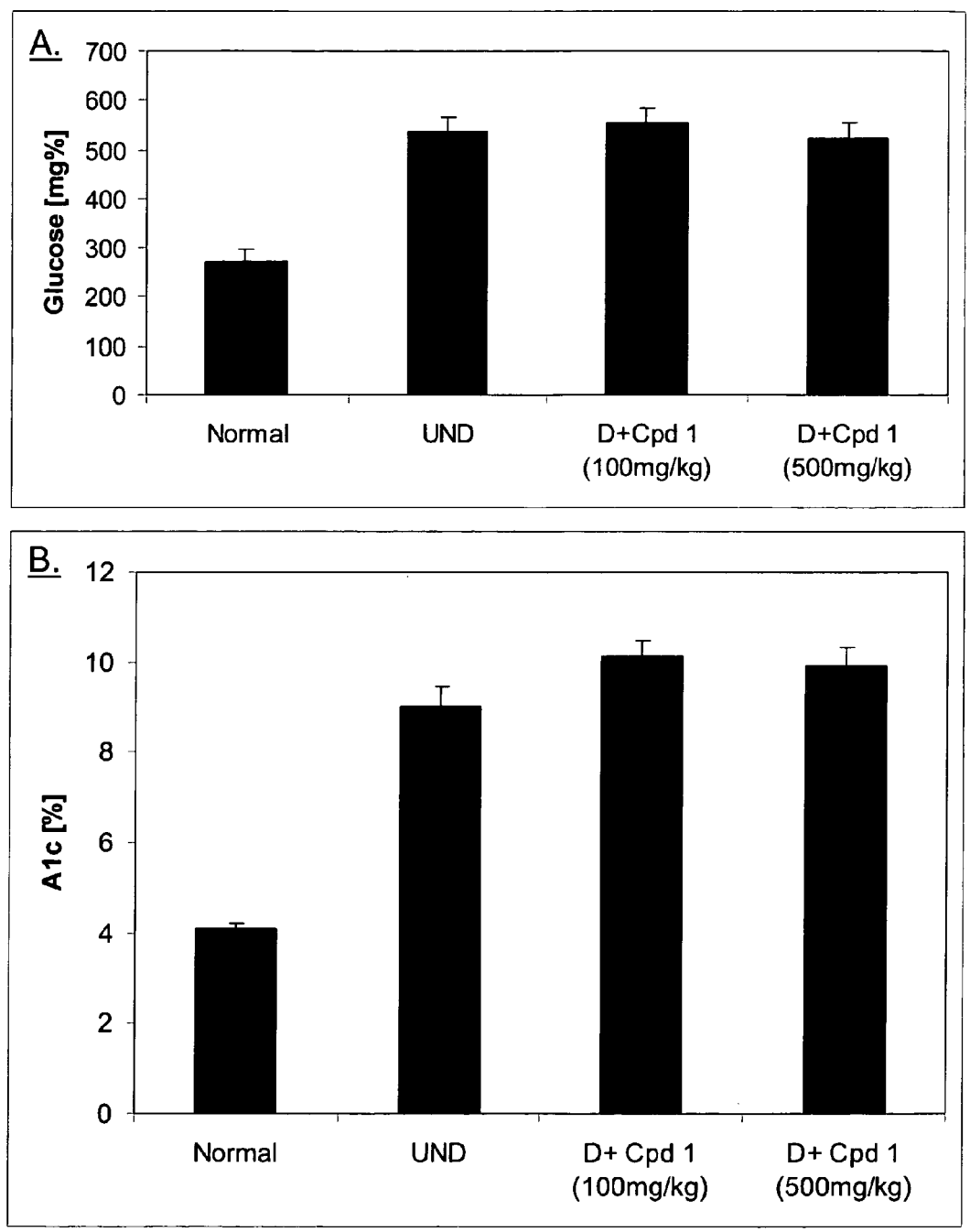
FIG. 9. The Effect of Diabetes and Orally-Administered Compound 1 on (A) Blood Glucose and (B) Hemoglobin A1c levels.

Similar to the Example 9 in vivo experiment described above, inducing diabetes with streptozotocin dramatically increased blood glucose (as well as hemoglobin Alc levels) and oral administration of compound 1, at both the lower (100 mg/kg) and higher (500 mg/kg) doses, had no significant effect on these diagnostic markers of the severity of diabetes/hyperglycemia (FIG. 9).

Figure 10:
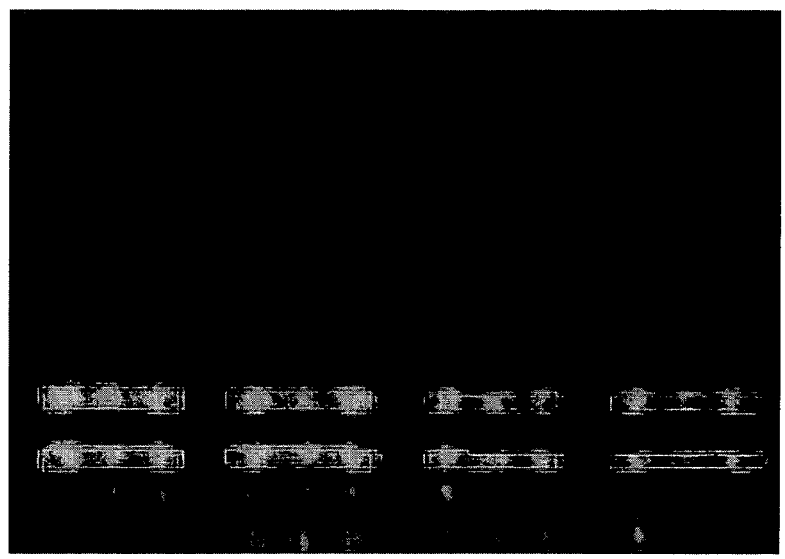
FIG. 10. The Effect of Diabetes and Oral Administration of Compound 1 on Gelatinase Levels in Gingiva, Assessed by Gelatin Zymography. Each value represents a pool of gingival tissue from 3 rats/experimental group.
Figure 10:
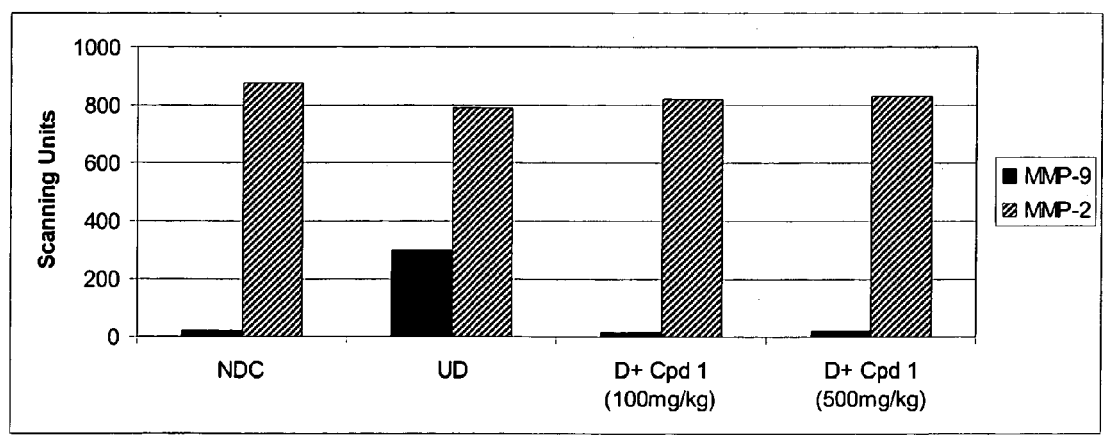
Figure 12:
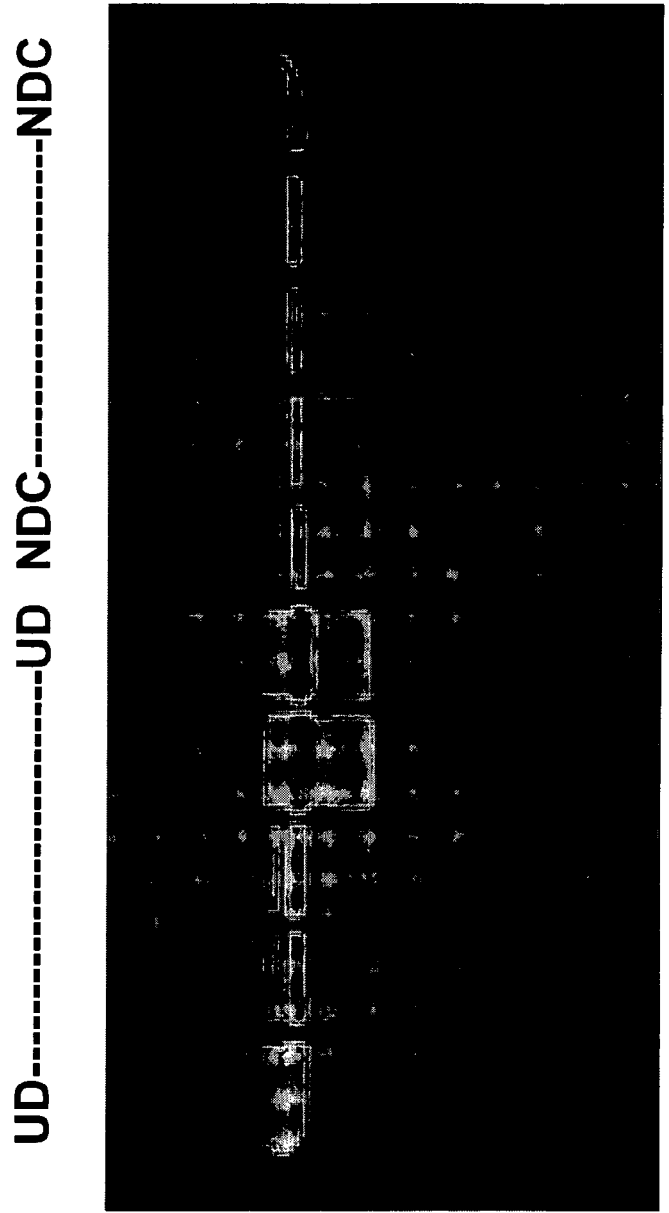
FIG. 12. Diabetes Increases the Levels of MMP-2 (pro- and active-forms) in the skin of rats, when compared to MMP-2 levels in the skin of non-diabetic control rats, assessed by gelatin zymography.

When the pools of gingiva from the different groups of rats were extracted, partially purified by ammonium sulfate precipitation, and the gelatinase (MMP-2 and MMP-9) levels examined by gelatin zymography (FIG. 10), NDC gingiva exhibited only 72 kDa pro-forms and lower molecular weight activated forms of MMP-2 (gelatinase A) which are generally produced in gingiva (and skin; FIG. 12) by fibroblasts and epithelial cells. However, inducing diabetes and hyperglycemia resulted in the appearance of 92 kDa gelatinase in the gingival tissues (ie., MMP-9 or gelatinase B) which is most often associated with inflammatory cells. This appearance of MMP-9 only in the gingiva (FIG. 10), but not the skin (FIG. 12), of the diabetic rats is likely the result of the oral bacteria inducing inflammation in the gingiva of these immune-suppressed UD rats, whereas the skin is not exposed to this onslaught of bacteria particularly the anaerobic gram-negative bacteria in the mouth that cause periodontal and gingival inflammation. Of importance, when the diabetic rats were treated by the oral administration of compound 1, both the lower (100 mg/kg) and the higher (500 mg/kg) doses reduced MMP-9 to the undetectable levels seen in the gingiva of the control (NDC) rats. However, neither diabetes nor compound 1 appeared to have a detectable effect on pro- and activated-forms of MMP-2 in the gingiva (FIG. 10).

Figure 11:
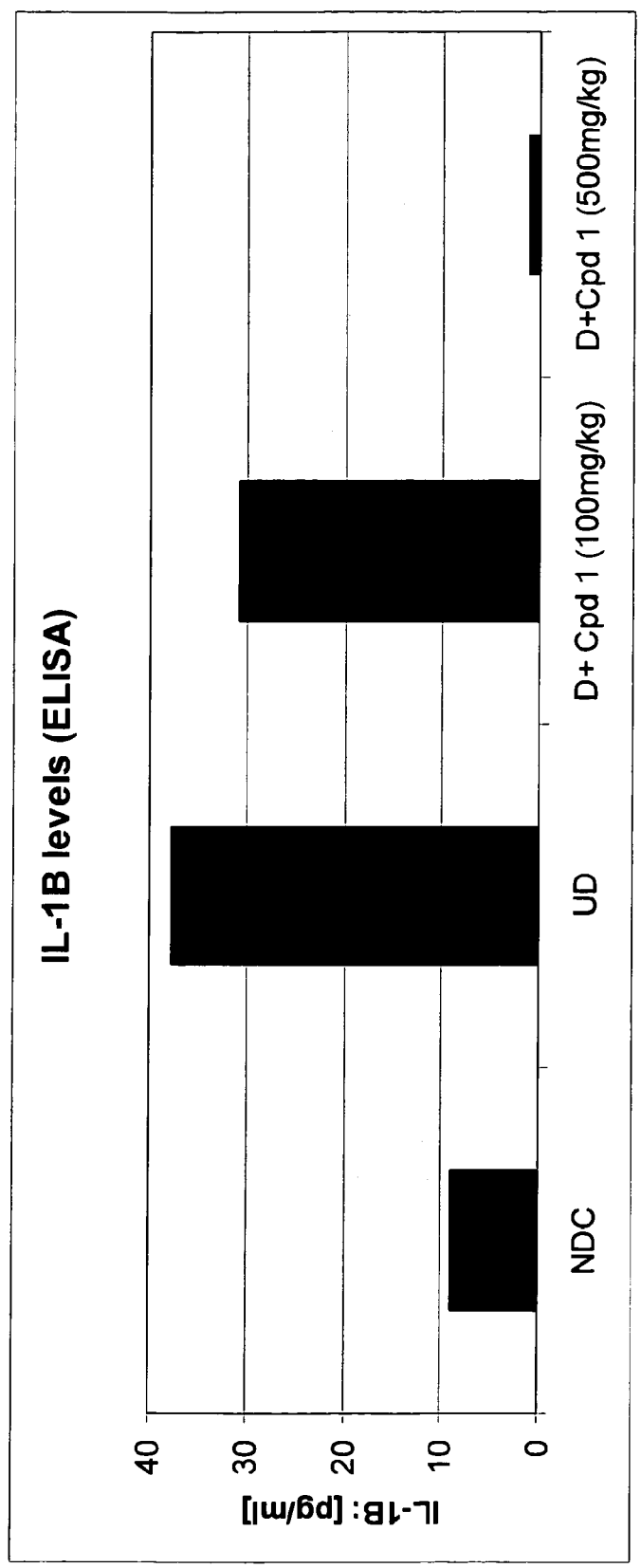
FIG. 11. The Effect of Diabetes and Oral Administration of Compound 1 on IL-1β levels by ELISA.

When a key inflammatory mediator in the gingiva, the cytokine IL-1β, was measured by ELISA in the partially-purified extracts of this oral tissue (the gingiva) a similar pattern was seen (FIG. 11). Diabetes increased the levels of IL-1β in the gingiva by 430% compared to the level seen in the NDC gingiva, and the higher oral dose of compound 1 reduced this cytokine by 95% compared to the high level of IL-1β seen in the UD rat gingiva. The lower dose of compound 1 appeared to reduce IL-1β by about 18%. Concerning the effect of this compound on cell signaling pathways, which can modulate the expression of pro-inflammatory cytokines such as IL-1β, compounds of the present invention, including compound 1, can inhibit NFκB phosphorylation/activation in human monocytes.

Example 11

Effect of Compound 1 on Alveolar Bone Loss

Figure 13:
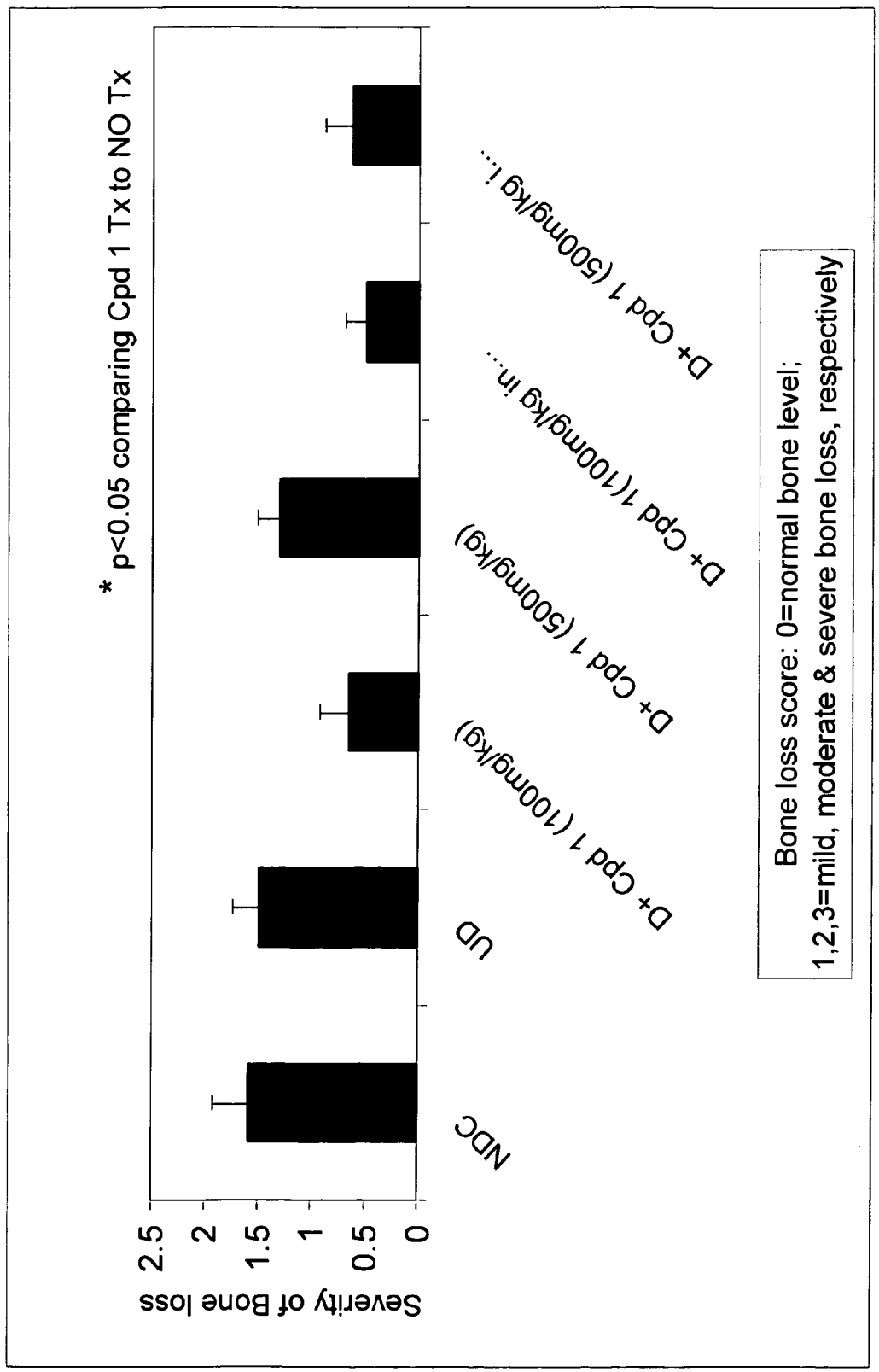
FIG. 13. The effect of oral administration of compound 1 on alveolar (periodontal) bone loss in hyperglycemic type I diabetic rats. Each value represents the mean bone loss score±the standard Error of the Mean (S.E.M.)

Alveolar bone loss (the signature pathologic event in inflammatory periodontal disease) was assessed in the defleshed jaws of the compound 1-treated (TX) and untreated rats. The results are summarized in FIG. 13.

Briefly, little or no difference in bone loss was seen comparing the untreated non-diabetic and untreated diabetic rat jaws (enhanced bone loss has been observed in diabetic rats previously when the duration of the hyperglycemia was greater than the 3-week experiment described herein). In this regard, both untreated groups of rats showed alveolar bone loss scores of approximately 1.5 (see FIG. 13). In contrast, when the diabetics were orally administered compound 1, the lower dose (100 mg/kg) produced about a 60%, statistically significant ($p<0.05$) reduction in bone loss compared to the untreated groups whereas the very high oral dose (500 mg/kg) was less effective.

These data indicate that the oral administration of compound 1 may be effective in reducing inflammatory- and tissue destructive-mediators of periodontal disease in this rat model of diabetes. The skin extracts did not exhibit MMP-9, only MMP-2 (gelatin zymography), and the elevated level of MMP-2 (assessed by ELISA) in the skin of the UD rats was reduced by 28% after treatment with both low and high doses of the test drug.

The lower dose of compound 1 is safer and more effective than the higher dose, and the carboxymethylcellulose vehicle, rather than the N-methylglucamine (the latter is more effective in solubilizing compound 1) is better for the diabetic rats because the glucamine may adversely effect the glucose metabolism of these animals.

Example 12

Evaluation of Compound 1 on hydrogen peroxide induced lactate dehydrogenase release and doxorubicin mediated caspase-3 activity in neonatal rat cardiac myocytes Test System: Neonatal Rat Ventricular Myocytes Test compounds and concentrations (MMP inhibitors, MMPi):

1. GM-6001: 10 μM
2. ONO-4817: 10 μM
3. Compound 1: 10 μM

The compounds were freshly prepared in DMSO (Sigma) and the final DMSO concentration did not exceed 0.1%. In pilot studies 0.1% DMSO did not have any effect on any of the parameters investigated.

Assays:

1. Lactate Dehydrogenase (LDH) Release

Neonatal rat ventricular myocytes, serum starved for 24 h, were treated with the inhibitors 1 h prior to the addition of 100 μM of hydrogen peroxide (Sigma). LDH release in the conditioned media was quantified using CytoTox-ONE Homogeneous Membrane Integrity Assay reagent (Promega) at the indicated time points.

2. Caspase-3 Activity

Neonatal rat ventricular myocytes, serum starved for 24 h, were treated with the inhibitors 1 h prior to the addition of 500 nM of doxorubicin (Sigma). At the indicated time points cells were washed with ice-cold phosphate buffered saline and lysed using RIPA buffer (Pierce) containing protease and phosphatase inhibitors (Sigma). Caspase-3 activity in the cell lysates was measured by incubation with 7-amino-4-trifluoromethyl coumarin (Enzo).

Figure 14:
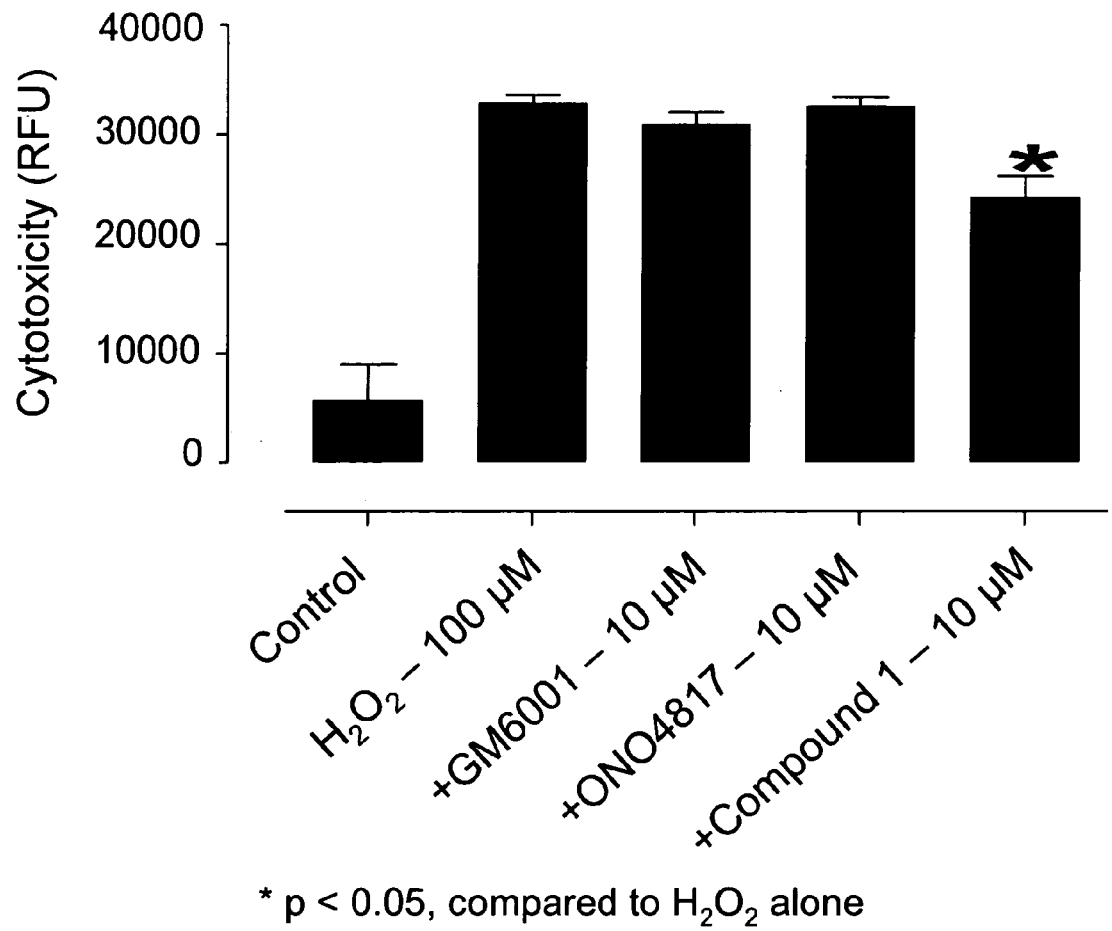
FIG. 14. Effect of MMP inhibitors on $H_2O_2$ (100 μM, 6 h) induced LDH release in neonatal rat ventricular myocytes (n=4).
Figure 15:
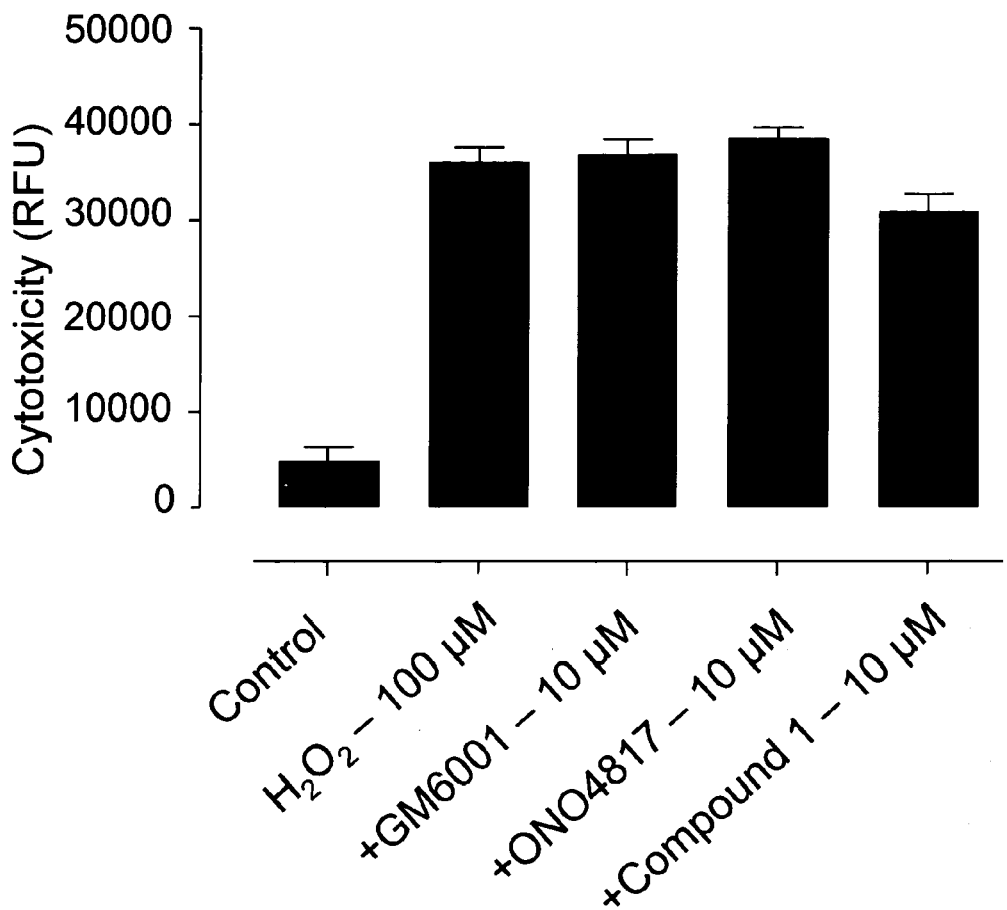
FIG. 15. Effect of MMP inhibitors on $H_2O_2$ (100 μM, 24 h) induced LDH release in neonatal rat ventricular myocytes (n=4).

Hydrogen peroxide (100 μM) induced LDH release was significantly attenuated by compound 1 at 6 h (32904±3237 hydrogen peroxide vs. 24286±930 compound 1, $p<0.05$, One-way-ANOVA followed by Dunnett's posthoc) (FIG. 14). A less dramatic effect of compound 1 on LDH release was observed at 24 h (FIG. 15). Other MMP inhibitors (GM-6001 or ONO-4817) did not affect LDH release at the tested concentrations in the current experimental conditions.

Figure 16:
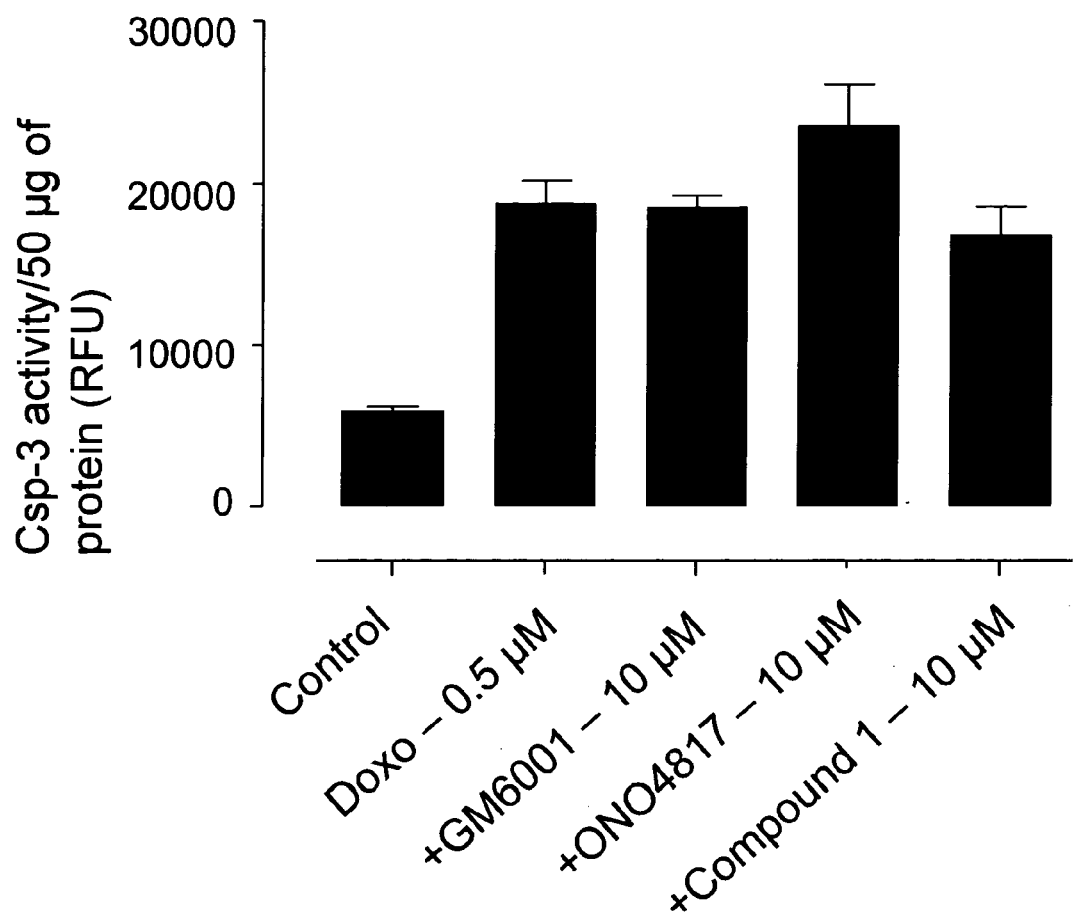
FIG. 16. Effect of MMP inhibitors on doxorubicin (0.5 μM, 6 h) induced caspase-3 activity in neonatal rat ventricular myocytes (n=4).
Figure 17:
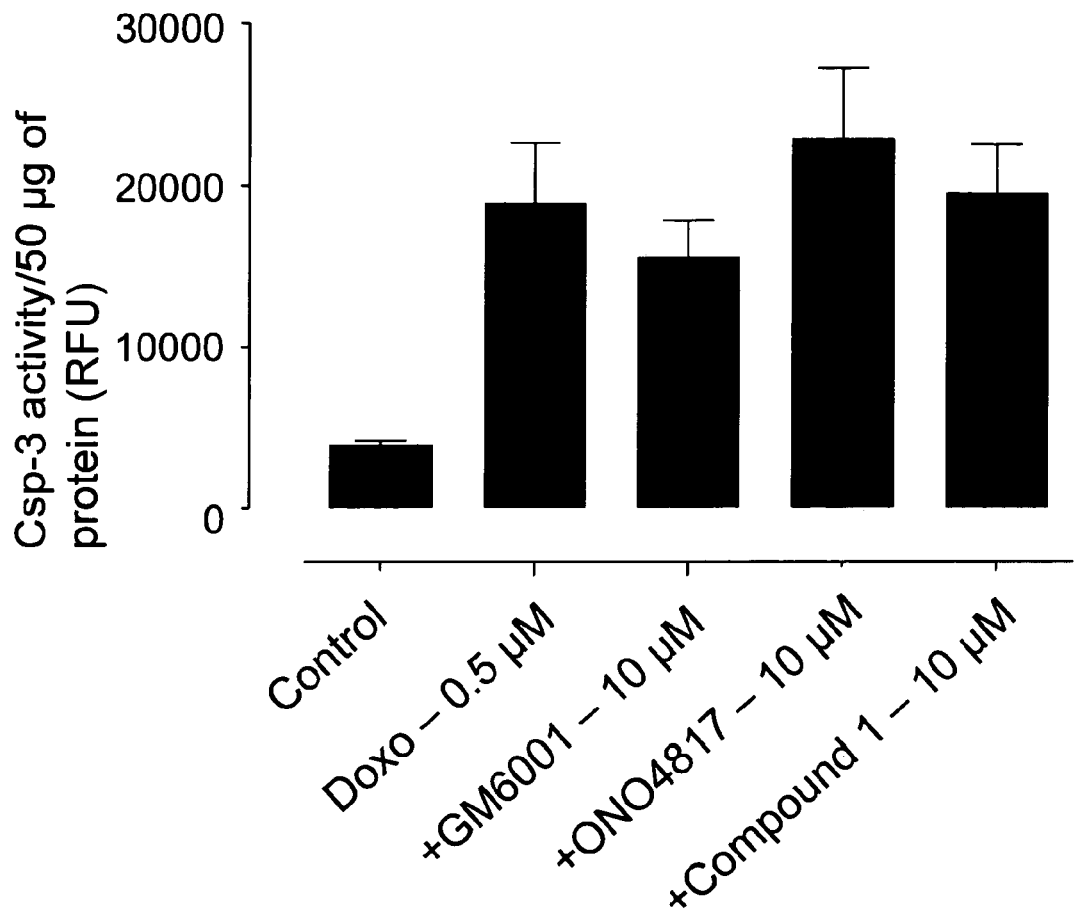
FIG. 17. Effect of MMP inhibitors on doxorubicin (0.5 μM, 24 h) induced caspase-3 activity in neonatal rat ventricular myocytes (n=4).

None of the MMP inhibitors, including compound 1, negatively modulate caspase-3 activity mediated by doxorubicin (500 nM) at any of the time points at the tested concentrations in the current experimental conditions (FIGS. 16 and 17).

Example 13

Effect of Compound 1 on Inflammatory Disease and Tissue Degradation

Full thickness cores of bovine articular cartilage [4 mm dia.] were harvested and equilibrated in tissue culture for 48 hours prior to any manipulations. All cartilage plugs were then incubated with S-35 labeled sulfate in the media for 24 hours to label all aggrecan molecules in a steady state manner. The cartilage plugs were then allocated to one of the following groups: control, with normal media, control with media containing interleukin 1 beta [IL-1β, 10 ng/ml]. IL-1 is a cytokine that is common to inflammatory cells and present in inflammatory environments. Exposure of cartilage to IL-1 results in a degradative process leading to loss of aggrecan molecules, which are an important matrix component responsible for maintaining the mechanical properties of the tissue. The loss of aggrecan is reflected in the amount of S-35 label present in the media after challenge with IL-1. IL-1 exposure is an indirect method for mimicking osteoarthritis. The other groups consisted of cartilage plugs which contained one of several novel derivatives of curcumin [10 um]—compound 1 and compound 5 (Table 5). These were also incubated with IL-1β.

Figure 18:
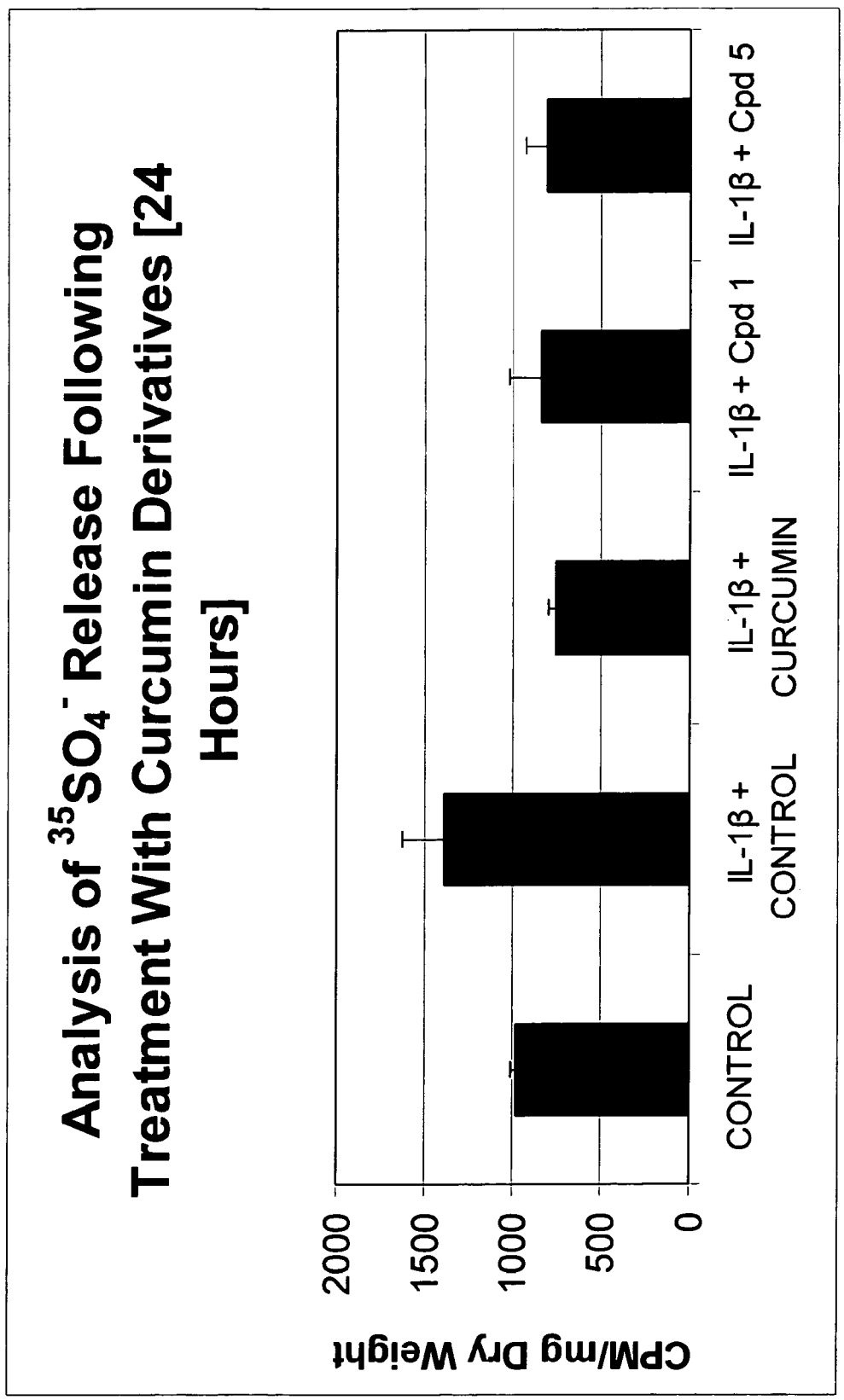
FIG. 18. Analysis of $^{35}SO_4^-$ release following treatment with curcumin derivatives (24 h).
Figure 19:
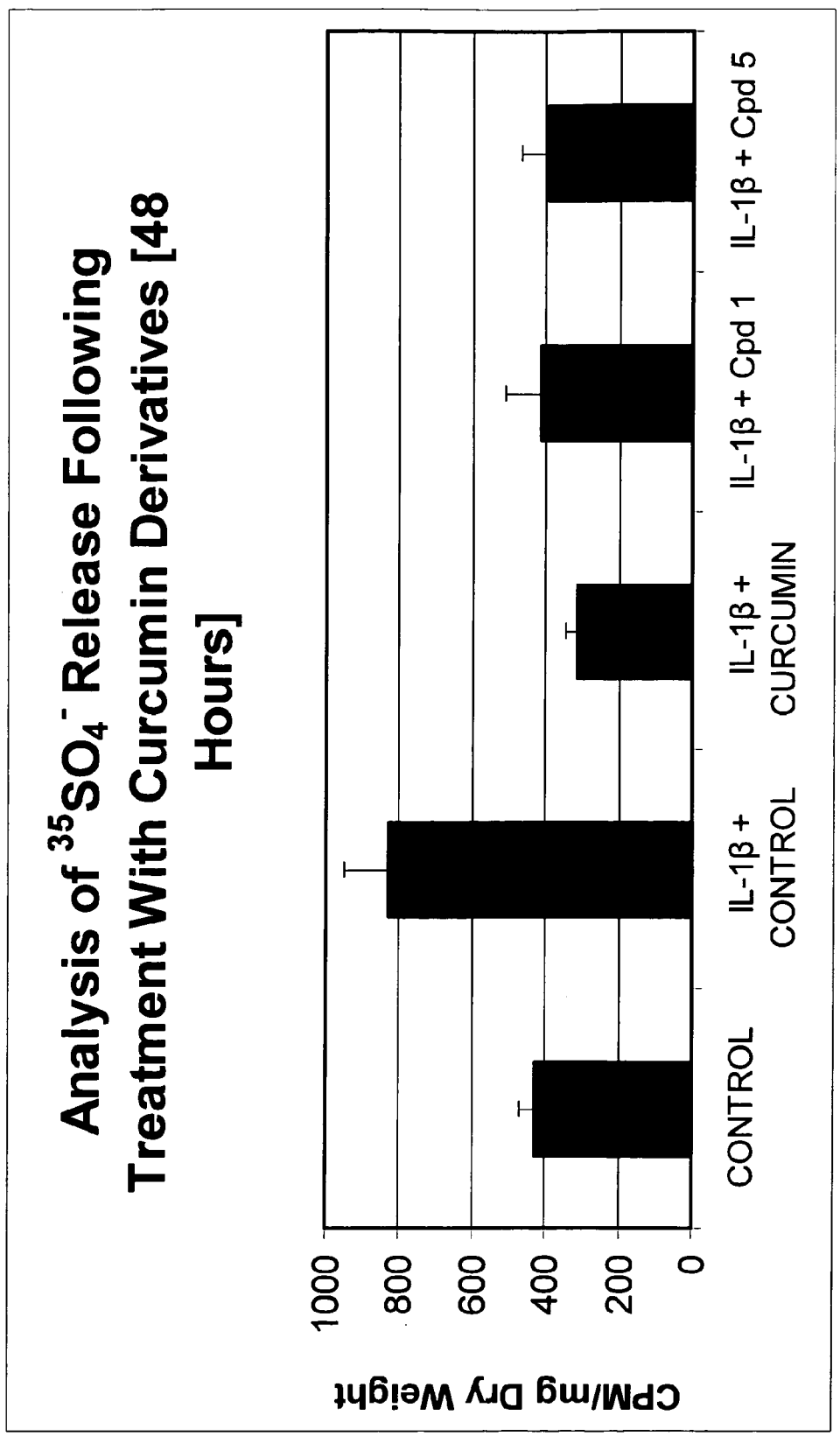
FIG. 19. Analysis of $^{35}SO_4^-$ release following treatment with curcumin derivatives (48 h).
Figure 20:
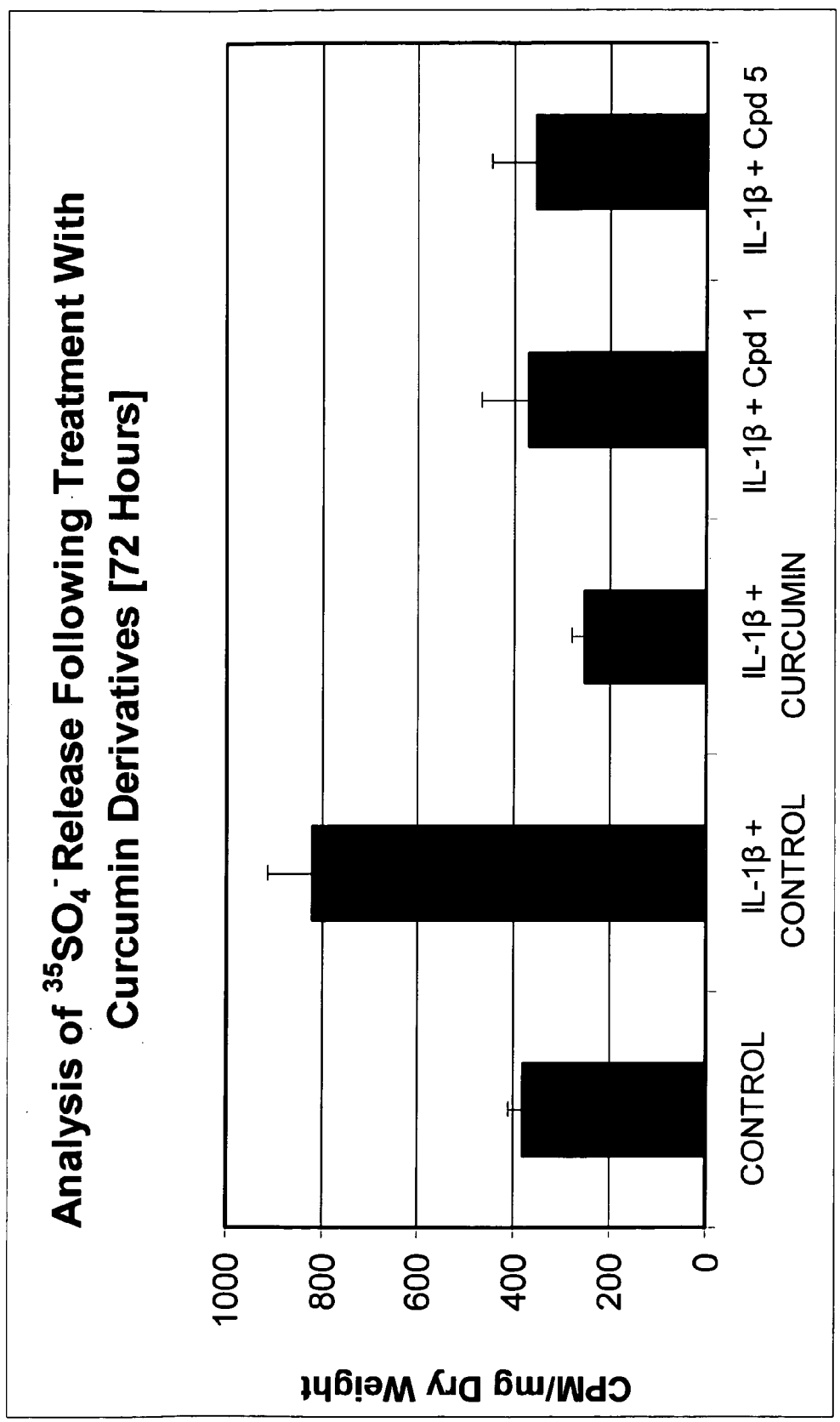
FIG. 20. Analysis of $^{35}SO_4^-$ release following treatment with curcumin derivatives (72 h).
Figure 21:
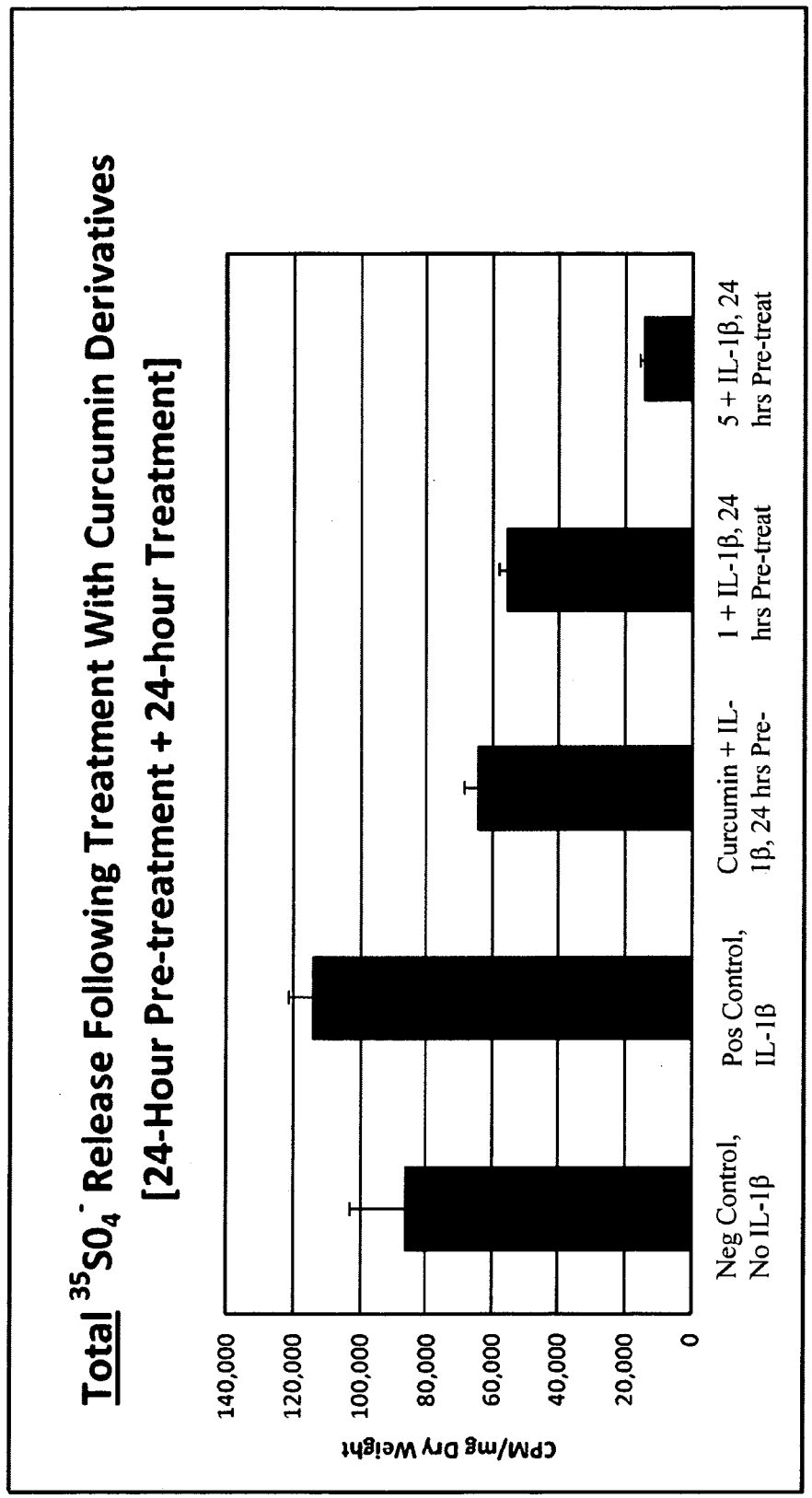
FIG. 21. Total $^{35}SO_4^-$ release following treatment with curcumin derivatives (24 hr pretreatment+24 h treatment).
Figure 22:
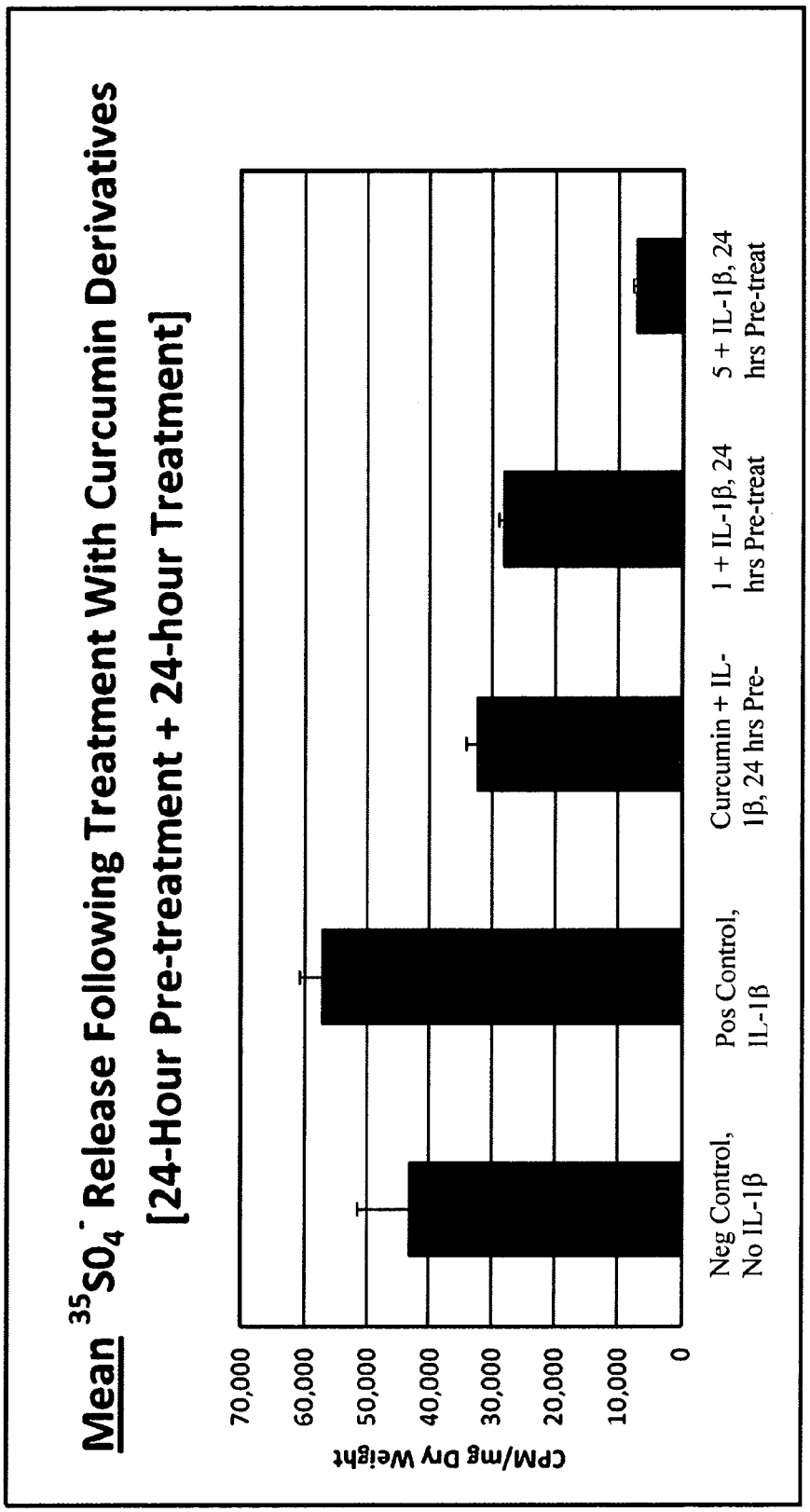
FIG. 22. Mean $^{35}SO_4^-$ release following treatment with curcumin derivatives (24 hr pretreatment+24 h treatment).

The results at 24 hours showed a significant decrease in loss of aggrecan, reflected by S-35 present in the media by all cartilage plugs treated with the experimental compounds. Control IL-1 treated cartilage demonstrated significant loss of aggrecan compared to the experimental compounds and media alone control (FIG. 18). The same trends continued for 48 and 72 hours (FIGS. 19 and 20). The same trends were also observed for 24-hour pretreatment+24-hour treatment (FIGS. 21 and 22).

Example 14

MMP Inhibitory Activity of Amide-Containing Curcumin Derivatives

Chemically-modified curcumins having a carbonyl-amide-phenol group at carbon 4 have been synthesized and exhibit greater solubility than curcumin. These amide-containing chemically-modified curcumins are were tested for their ability to inhibit chromatographically-purified MMPs—MMP-2 and MMP-13—using the same assay described previously in Example 2, ie., the degradation of the MMP-susceptible, synthetic octapeptide and the measurement of the tripeptide degradation fragment and residual substrate by HPLC (37° C., 1 mM $Ca^{++}$). As shown in Table 9, curcumin was less potent as an inhibitor of MMP-2 than the Zn-chelating agent, 1,10-phenanthroline (higher $IC_{50}$, and less inhibitory activities at 100 μM concentration). Compound 1 (based on in vitro, cell culture, and in vivo efficacy) was again most potent as an MMP inhibitor (this time against MMP-2, showing the lowest $IC_{50}$ ratio: test compound vs. standard (ratio=0.7) and inhibiting MMP-2 activity by 78% at 100 μM concentration.

TABLE 8

Structure of amide-containing curcumin compounds

Compound 6

Compound 7

Compound 8

In contrast, compounds 4 and 3, which are not amide compounds but which showed excellent potency as inhibitors of MMP-9 in Example 8, showed very different levels of efficacy against MMP-2 (Table 9).

TABLE 9

MMP Inhibitory Potency of Amide-Containing Curcumin Derivatives

| Compound Tested | MMP-2 Ratio* | MMP-2 Maximum Inhibition @ 100 μM | MMP-13 Ratio* | MMP-13 Maximum Inhibition @ 100 μM |
|---|---|---|---|---|
| 1,10-phenanthroline (standard) | 1.0 | 60% | 1.0 | 100% |
| Curcumin | 1.2 | 54% | 27.5 | 53% |
| Compound 1 | 0.7 | 78% | 3.8 | 69% |
| Compound 4 | >3.6 | 36% | 62.5 | 50% |
| Compound 3 | 1.0 | 60% | 2.0 | 76% |
| Compound 6++ | 1.2 | 53% | <0.3 | 100% |
| Compound 7++ | 1.8 | 45% | <0.3 | 77% |
| Compound 8++ | — | — | 11.3 | 53% |

++amide-containing curcumin derivatives
*Ratio = $IC_{50}$ test compound/$IC_{50}$ standard Compound 4 was less effective than the standard, 1,10-phenanthroline, while compound 3 was equal in efficacy to 1,10-phenanthroline. Of the three amide-containing compounds tested, compounds 6, 7, and 8, the efficacy of MMP-2 inhibition was as follows: compound 6>compound 7>compound 8. Although compound 6 showed similar efficacy as curcumin when comparing MMP-2 inhibitory potency, the amide-containing compounds are much more soluble than the famously insoluble curcumin.

The amide-containing curcumin derivatives are much more potent inhibitors of MMP-13 (Collagenase-3) than curcumin and even more potent than compound 1 (Table 9 and 10).

It should be noted that the tetracyclines, which resulted in two FDA-approved drugs for chronic inflammatory diseases, were very effective as inhibitors of MMP-9 and MMP-13 and much less effective against MMP-2 (see Brown et al, 2004; Sorsa et al). Compounds 1, 6, and 7 fit such a profile (Table 10) and, therefore, are expected to be effective for use in treating chronic inflammatory diseases.

TABLE 10

Concentration of Curcumin Derivatives Required to Inhibit 50% of Enzyme Activity ($IC_{50}$ values)

| Compound Tested | $IC_{50}$ values (μM; Inhibition of Different MMPs) MMP-2 (μM) | MMP-13 (μM) |
|---|---|---|
| 1,10-phenanthroline | 70 | 4 |
| Curcumin | 85 | 110 |

TABLE 10-continued

Concentration of Curcumin Derivatives Required
to Inhibit 50% of Enzyme Activity (IC$_{50}$ values)

| Compound Tested | IC$_{50}$ values (μM; Inhibition of Different MMPs) | |
|---|---|---|
| | MMP-2 (μM) | MMP-13 (μM) |
| Compound 1 | 48 | 15 |
| Compound 4 | >250* | 250 |
| Compound 3 | 70 | 8 |
| Compound 6++ | 85 | <1 |
| Compound 7++ | 125 | <1 |
| Compound 8++ | Unmeasurable* | 45 |

++more soluble amide-containing compounds
*evidence of precipitation

Example 15

Evaluation of Compound 1 in a Cell Culture Model of Cancer

Figure 23:
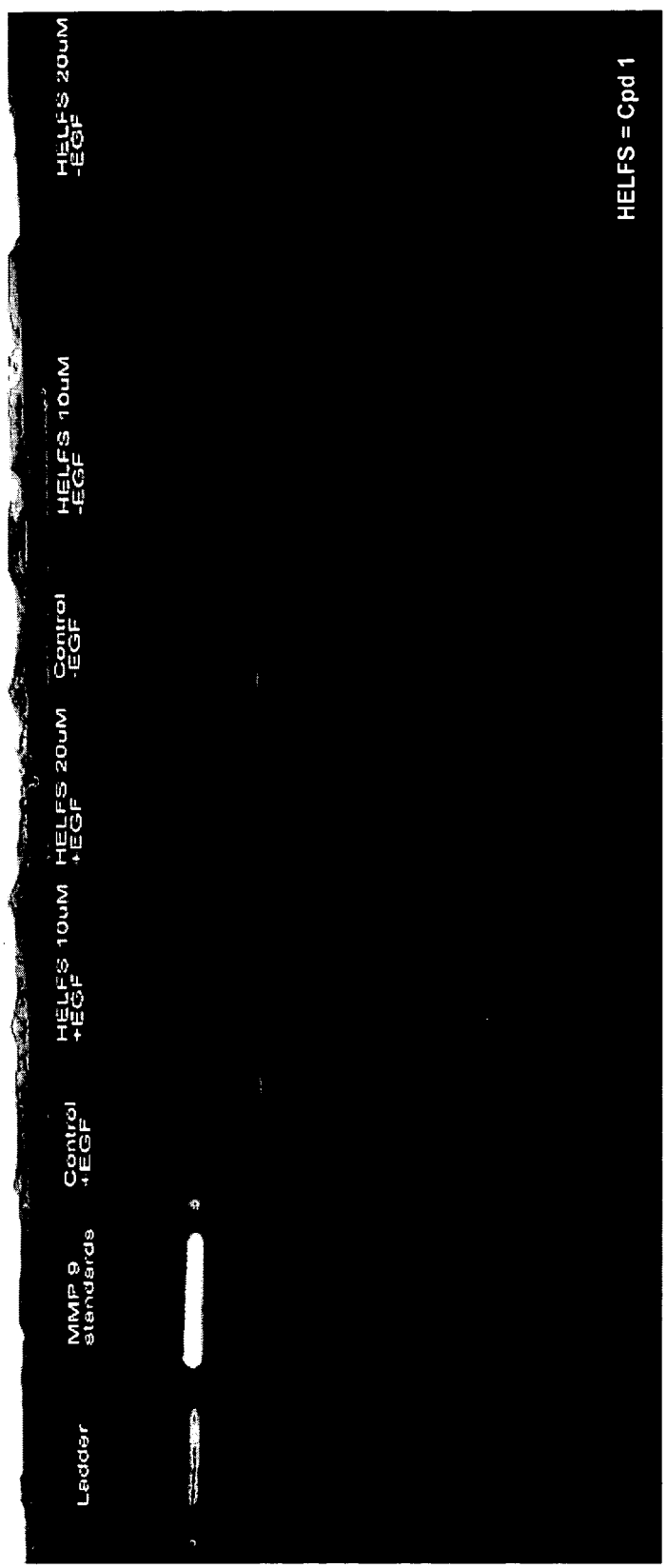
FIG. 23-25. Gelatin zymography (in the presence of 2 or 10 mM$Ca^{++}$) and Western blot (both assays used purified MMP-9, 92 kDa gelatinase, as a standard). The 10 μM and 20 μM concentrations of compound 1 inhibited the production and/or activity of MMP-9 generated by the human prostate cancer cells.
Figure 24:
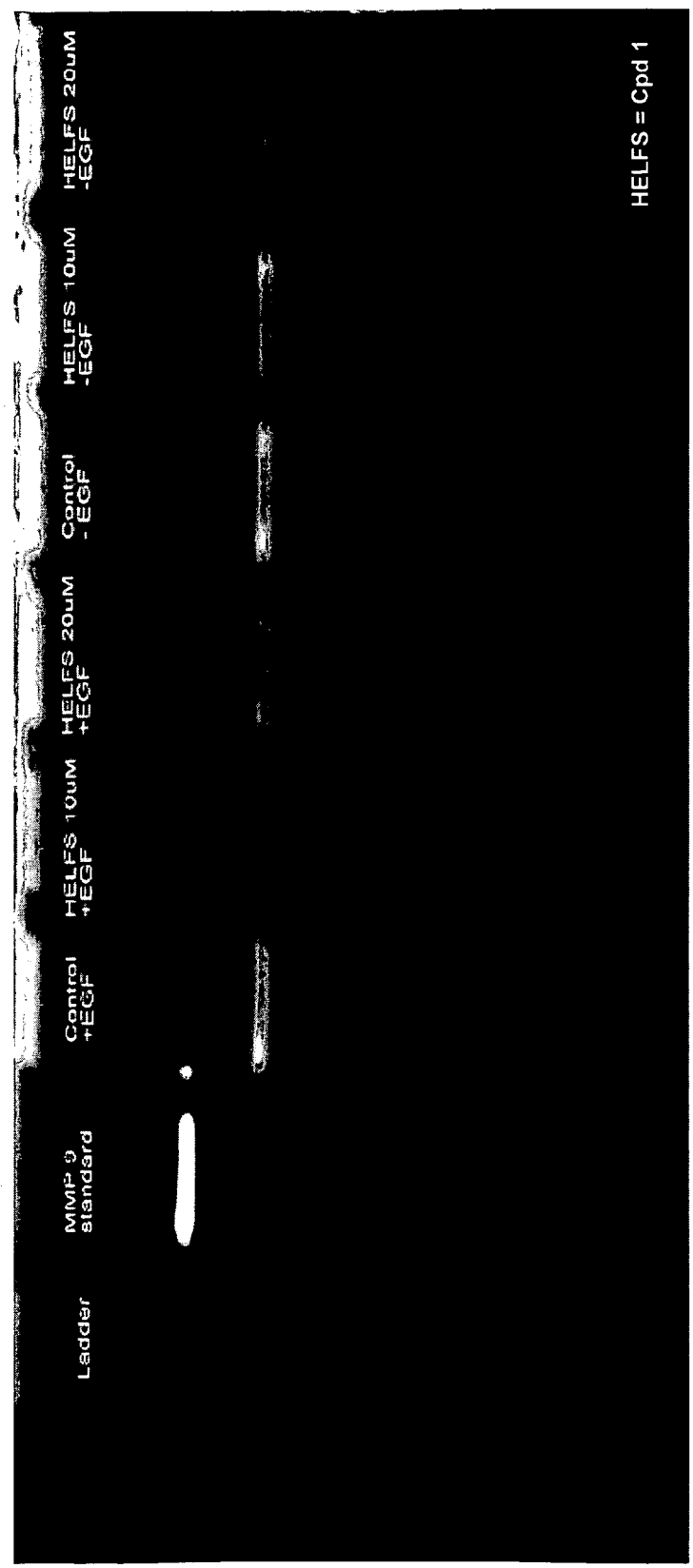
Figure 25:
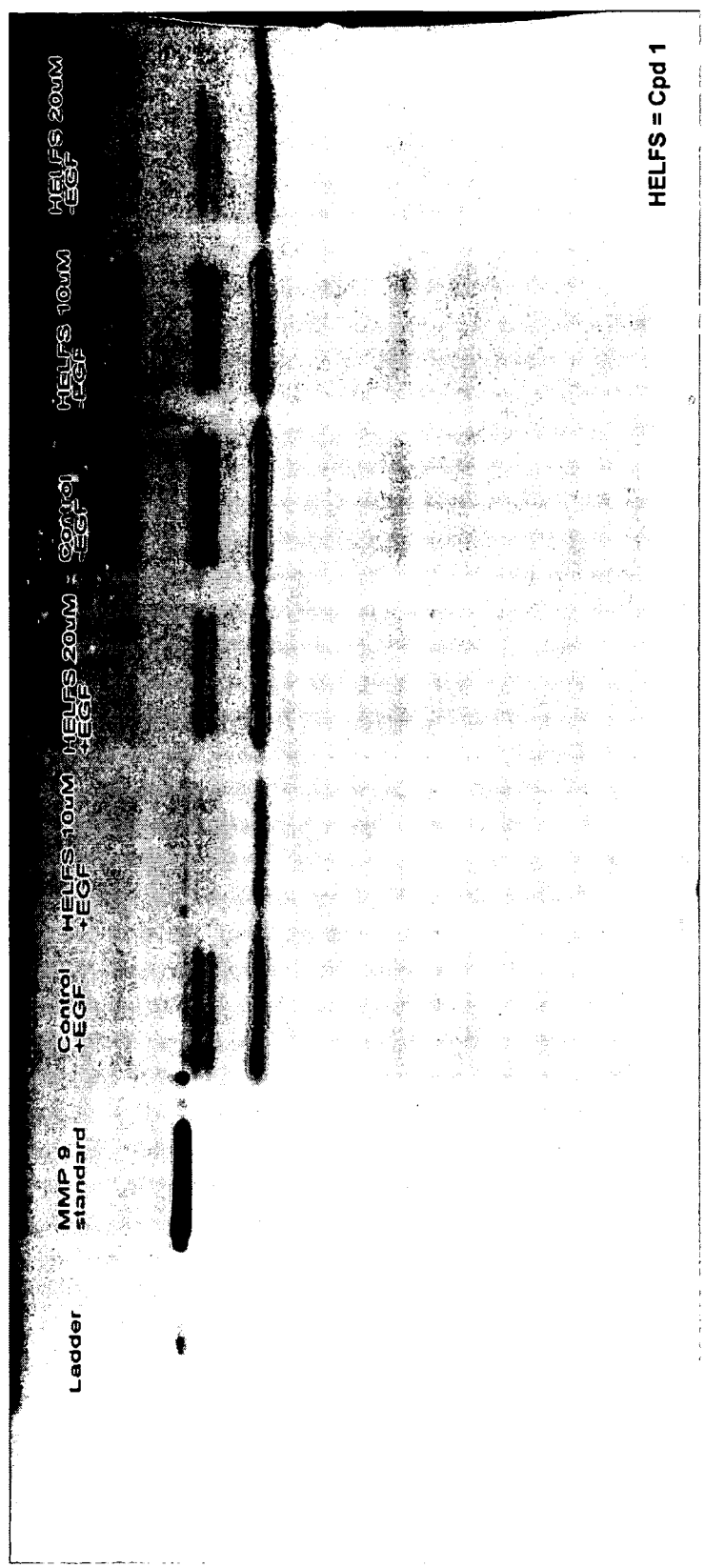

Compound 1 was evaluated in a cell culture model of cancer. In brief, PC-3 human prostate cancer cells were incubated in serum-free media for 48 hr (37° C., pH7.6) in the presence or absence of EGF and compound 1 was added to the cultures at a final concentration of 0, 10, and 20 μM. After the incubation, aliquots of the conditioned media were assayed for MMP-9 (gelatinase B) by either of two techniques, gelatin zymography (in the presence of 2 or 10 mMCa$^{++}$) and Western blot (both assays used purified MMP-9, 92 kDa gelatinase, as a standard). As shown in FIGS. 23-25, the 10 μM and 20 μM concentrations of compound 1 inhibited the production and/or activity of 9 generated by the human prostate cancer cells.

Discussion

While investigations have been conducted to improve curcumin through the synthesis of curcumin-based analogues and derivatives (14-18), previous efforts did not appreciate that installation of an electron-withdrawing group on the C-4 carbon (see FIG. 1) of curcumin and its analogues improves a number of pharmacologically important characteristics of such compounds.

As alluded to earlier, the biological activity of curcumin and its analogues is attributed to their ability to access and bind zinc ions. The discovery of the enhancement of zinc binding affinity through the installation of electron-donating and electron-withdrawing groups at strategic locations, namely the C-4 carbon and the aryl rings, on the curcumin skeleton is important for enhancing biological activity. In particular, the incorporation of an electron-withdrawing group on the C-4 carbon is shown to be essential for the improvement of zinc binding affinity, which leads to an enhancement in biological activity.

Published work which examined curcumin analog compounds having an electron-withdrawing group indicated contrasting effects of such a group. Lin and co-workers reported lower cytoxicity (higher IC$_{50}$), ie. a reduction of activity, with a curcumin analogue having an acetyl group at the C-4 position (compound 49 in ref. 10) in comparison with that of curcumin (compound 1 in ref. 14) when tested against human prostate cancer cells (14). On the contrary, Shih et al. reported reduced androgen receptor (AR) expression within cancer cells, ie. higher cytotoxicity, with a dimethylcurcumin analogue having a substituted phenylpropenal moiety (compound ASC-JM4 in ref. 11b) at low concentrations when compared to dimethylcurcumin (compound ASC-J9 in ref. 15b). However, Shih et al. did not publish on further curcumins having other substituents at the C-4 carbon. These studies indicate that researchers have not appreciated the importance of an electron-withdrawing group at the C-4 carbon of curcumin and its analogues.

As described herein, the placement of an electron-withdrawing group at the C-4 carbon of curcumin and curcumin analogues confers several advantages, such as improved water solubility, improved metal binding ability, and improved biological activity when compared to curcumin. Without wishing to be bound by theory, it is believed that the presence of an electron-withdrawing group at the C-4 position of curcumin and curcumin analogues stabilizes the enol form of the compound as well as the enolate formed from deprotonation at the C-4 carbon, thereby facilitating water solubility and chelation of metal cations, such as Zn$^{2+}$, by the resulting curcumin enolate. Accordingly, other curcumin analogues having electron-withdrawing groups at the C-4 carbon possess such prope and function in a similar manner.

Compounds of the subject invention are tested and exhibit activity consistent with those of the foregoing examples.

Specifically, the compounds of the subject invention are useful for the inhibition of matrix metalloproteinase activity as well as the inhibition of both cytokine production and NFκB activation in vivo and in vitro, and are useful for treating pathologies in subjects arising from matrix metalloproteinase activity, growth factor activity, cytokine production, and/or NFκB activation.

Although numerous experimental agents have been developed over the years with excellent potency as inhibitors of collagenases (MMP-1, MMP-8 and MMP-13) and other MMPs (e.g., the gelatinases, MMP-2 and MMP-9; the stromelysins, MMP-3 and MMP-10) (8), the only MMP-inhibitor (MMPI) drug approved by the U.S. FDA and regulatory agencies in Europe and Canada is a NON-ANTIBIOTIC formulation of doxycycline (subantimicrobial-dose doxycycline, SDD) called Periostat® marketed for the treatment of the most common of all chronic inflammatory diseases, periodontitis, which involves the destruction of collagen and other connective tissues in the gingiva, periodontal ligament, and bone, as mentioned previously (4). Oracea®, a sustained-release SDD, also administered systemically by the oral route, was recently approved by the US FDA and in Europe for the treatment of a chronic inflammatory skin condition, rosacea.

Several factors explain, at least in part, this difficulty in bringing MMPI drugs to clinical application: (1) It is recognized that MMPs play a role in various physiologic (not just pathologic) processes, such as processing anti-inflammatory cytokines and chemokines as well as modulating growth factors or cell surface receptors, and regulating cellular proliferation and apoptotic and immune responses (2, 3, 27). Therefore, the goal of MMPI therapy must be to dampen or modulate pathologic levels of MMPs, NOT to excessively inhibit them (2, 4, 27); and (2) Based on past experience with SDD, and other drug-development strategies, it may be desirable to chemically-modify compounds which incorporate the same or similar active sites for MMP-inhibition, which are derived from agents with a long history of safety in humans since, for chronic diseases, they are likely to have to be administered for long periods of time. Considering the MMPI drugs, Periostat® and Oracea®, these were based on the well-known drug, doxycycline, a tetracycline which was deliberately titrated down to subantimicrobial concentrations in the circulation, after oral administration, so that they would not produce antibiotic side-effects during long-term administration, but which would retain the Ca$^{++}$ and Zn$^{++}$ site at carbon-11 and carbon-12 to inhibit collagenases and gelatinases, as well as other pleiotropic benefits of those drugs (see ref. 4 for review). However, because of the concern for the side-effects of all tetracyclines including doxycycline, only a narrow (perhaps sub-optimal) range of non-antimicrobial blood levels of the drug (e.g., 0.3-0.8 µg ml) could be considered therapeutically useful because of the concern for the emergence of antibiotic-resistant bacteria at higher blood levels (and other concerns, such as increased sensitivity to sunburn).

The capability to down-regulate MMP production and activity, but not to inhibit these enzymes completely, has a significant impact on several diseases which are chronic afflictions particularly in adults and older age groups. As described herein, the compounds and compositions of the present invention inhibit the production of a variety of pro-inflammatory cytokines (e.g., IL-1β, TNFα, IL-6) which are also key participants in the pathogenesis of these chronic diseases. These diseases include, but are not limited to, impaired wound healing and other skin conditions (e.g., psoriasis (44)), periodontitis, arthritis, cardiovascular disease, osteoporosis, acute respiratory distress syndrome, and cancer. The development of an effective non-toxic modulator of MMPs and cytokines constitutes a significant advancement in pharmacotherapeutics. The safety and efficacy of the compounds of the present invention in vivo in diabetic complications in skin (e.g., skin aging/atrophy), and in inflammatory gingival disease and periodontal bone loss, and in cell and tissue culture models of arthritis and cardiac myocyte dysfunction and MMPs produced by prostate cancer cells are shown herein.

Using a severely hyperglycemic type I diabetic rat model, which produces increased levels of MMPs and pro-inflammatory cytokines compared to non-diabetic controls, the oral administration of compound 1 has been found to: (i) reduce MMP-2 and MMP-9 in plasma, (ii) reduce MMP-2 and MMP-8 in skin, and (iii) reduce MMP-9 and IL-1β in gingiva. Moreover, oral administration of compound 1 also reduced pathologic alveolar bone loss which, together with elevated MMPs and cytokines, is a signature event in both diabetes and periodontitis. All of these beneficial effects were accompanied by an apparent improvement in adverse events produced by the severe diabetic condition. Diabetic complications, not the severity of diabetes per se, were improved.

REFERENCES

1. Gross J and Lapiere C M. Collagenolytic activity in amphibian tissues: a tissue culture assay. Proc. Natl. Acad. Sci., 48: 1014-1022, 1962.

2. Sorsa T, Tjäderhane L, Konttinen Y T, Lauhrio A, et al. Matrix metalloproteinases: contribution to pathogenesis, diagnosis and treatment for periodontal inflammation. Ann. Med., 38: 306-321, 2006.

3. Roy R, Yang J and Moses M A. Matrix metalloproteinases as novel biomarkers and potential therapeutic targets in human cancer. J. Olin. Oncol., 27: 5287-5297, 2009.

4. Golub et al. (1998) "Tetracyclines Inhibit Connective Tissue Breakdown by Multiple Non-Antimicrobial Mechanisms" Adv. Dent. Res., 12, pp. 12-26.

5. Close, D R. (2001) "Matrix metalloproteinase inhibitors in rheumatic diseases." Ann. Rhuem. Dis., 60, pp. iii62-iii67.

6. (a) Dove, A. (2002) "MMP inhibitors: Glimmers of hope amidst clinical failures." Nature Med., 8 (2), p. 95. (b) Trivedi N R, Gilliland K L, Zhao W L, et al (2006). Gene Array expansion profiling in acne lesions reveals marked upregulation of genes involved in inflammation and matrix remodeling. Joural of Invest. Derm. 126 (5): 1071-1079; (c) Papakonatantinov E, Aletius A J, Glass E, et al. (2005) Matrix Metalloproteinases of epitheilial origin in facial sebum of patients with acne and their regulationby isotretindin. Journal of Invest. Derm 125 (4):673-684.

7. Borkakoti, N. (2004) "Matrix metalloprotease inhibitors: design from structure." Biochem Soc. Trans., vol. 32, part 1, pp. 17-20.

8. Peterson, J T. (2006) "The importance of estimating the therapeutic index in the development of matrix metalloproteinase inhibitors." Cardio. Res., 69, pp. 677-687.

9. Bachmeier, B E, et al. (2008) "Curcumin downregulates the inflammatory cytokines CXCL1 and -2 in breast cancer cells via NFκB." Carcinogenesis, 29 (4), pp. 779-789.

10. Kaur, G, at al. (2006) "Inhibition of oxidative stress and cytokine activity by curcumin in amelioration of endotoxin-induced experiemental hepatotoxicity." Clin. Exp. Immunol., 145, pp. 313-321.

11. Begum, A N, et al. (2008) "Curcumin structure-function, bioavailability, and efficacy in models of neuroinflammation and Alzheimer's disease." J. Pharm. Exp. Ther., 326 (1), pp. 196-208.

12. Banerji, A, et al. (2004) "Effect of curcumin on gelatinase A (MMP-2) activity in B16F10 melanoma cells." Cancer Lett., 211 (2), pp. 235-242.

13. Woo, M.-S., et al. (2005) "Curcumin suppresses phorbol ester-induced metric metalloproteinase-9 expression by inhibiting the PKC to MAPK signaling pathways in human astroglioma cells." Biochem. Biophys. Res. Comm., 335, 1017-1025.

14. Lin, L, et al. (2006) "Antitumor Agents. 250. Design and Synthesis of New Curcumin analogues as Potential Antiprostate cancer Agents." J. Med. Chem., 49 (13), pp. 3963-3972.

15. a) Lee et al. U.S. Pat. No. 7,355,081; b) Shih et al. POT International Application Publication WO 2008/085984.

16. Safavy et al. PCT International Application Publication WO 2008/051474.

17. Van Der Jagt et al. US Patent Application Publication 2006/0276536.

18. Pandol et al. U.S. Pat. No. 7,060,733.

19. Baum, L; Ng, A. (2004) "Curcumin interaction with copper and iron suggests one possible mechanism of action in Alzheimer's disease animal models." Journal of Alzheimer's Disease, 6 (4), pp. 367-377.

20. Heng, M. PCT International Application Publication WO 99/42094.

21. Singer, A. et al. (2007) "Curcumin Reduces Burn Progression in Rats," Acad. Emerg. Med., 14, pp. 1125-1129.

22. Sidhu, G S. et al. (1998) "Enhancement of wound healing by curcumin in animals," Wound Rep. Reg., 6, pp. 167-177.

23. Sidhu, G S. et al. (1999) "Curcumin enhances wound healing in streptozoticin induced diabetic rats and genetically diabetic mice," Wound Rep. Reg., 7, pp. 362-374.

24. Phan, T.-T. et al. (2001) "Protective effects of curcumin against oxidative damage on skin cells in vitro: Its implication for wound healing," J. Trauma, 51, pp. 927-931.

25. Budnikova, M V; Rubinov, D B. (2001) "Synthesis of Endocyclic Enol Methyl Ethers of 3-Acylthiotetronic Acids and Their Reactions with Amines," Russian Journal of Organic Chemistry, 37 (10), pp. 1478-1485.

26. Saito, K; Sato, T. (1978) "Diversity in the base-induced photoreactions of 3-acetyl-2,4-dioxothiolane (3-acetylthiotetronic acid)." Chem. Lett., pp. 307-310.

27. Sorsa T and Golub L M. (2005) "Is the excessive inhibition of matrix metalloproteinases (MMPs) by potent synthetic MMP inhibitors (MMPIs) desirable in periodontitis and other inflammatory diseases? That is: 'Leaky' MMPIs vs excessively efficient drugs" Oral Dis., 11, pp. 408-409.

28. Golub et al. (1996) "New therapeutic uses for an old family of drugs: travels of a dental researcher from the lab to the university's office of technology transfer and beyond." Technol. Health Care, 4, pp. 311-316.

29. Liu et al. (2001) "The Lipophilicity, Pharmacokinetics, and Cellular Uptake of Different Chemically-Modified Tetracyclines (CMTs)." Curr. Med. Chem., 8, pp. 243-252.

30. Yu Z et al. (1993) "Chemically-modified tetracycline normalizes collagen metabolism in diabetic rats: a dose-response study." *J Periodontal Res.*, 28 (6 Pt 1), pp. 420-428.

31. Ryan M E et. al. (2001) "Excessive matrix metalloproteinase activity in diabetes: inhibition by tetracycline analogues with zinc reactivity." *Curr Med Chem.*, 8 (3), pp. 305-316.

32. Ryan M E et al. (1999) "MMP-mediated events in diabetes." *Ann NY Acad Sri.*, 878, pp. 311-334.

33. Ramamurthy N S, Zebrowski E J & Golub L M. (1973) "Collagenolytic activity of alloxan diabetic rat gingivae." Diabetes, 22, pp. 272-274.

34. Golub L M, Greenwald R A, Zebrowski E J & Ramamurthy N S. (1978) "The effect of experimental diabetes on the molecular characteristics of rat tail tendon collagen." Biochim. Biophys. Acta, 534, pp. 73-81.

35. Schneir, M. and Golub, L. M. (1981) "The effect of streptozotocin diabetes on collagen metabolism." In Agarwal, M. K. (Ed.): Streptozotocin: Fundamentals and Therapy. Elsevier/North Holland Biomedical Press, pp. 161-182.

36. Schneir M, Ramamurthy N S & Golub L M. (1985) "Dietary ascorbic acid normalized diabetes-induced underhydroxylation of nascent type I collagen molecules." Collagen Rel. Res., 5, pp. 415-422,.

37. Leung M K, Folkes G A, Ramamurthy N S & Golub, L M. (1986) "Diabetes stimulates procollagen degradation in rat tendon in vitro." Biochim. Biophys. Acta, 880, pp. 147-152.

38. Schneir M, Imberman M, Ramamurthy N S & Golub L M. (1988) "Streptozotocin-induced diabetes and the rat periodontium: Decreased relative collagen production." Collagen Rel. Res., 8, pp. 221-232.

39. Schneir M, Ramamurthy N S & Golub L M. (1990) "Minocycline treatment of diabetic rats increases skin collagen production and mass." Matrix, 10, pp. 112-123.

40. Golub L M, Ramamurthy N S, Lee H M & Rifkin, B. (1990) Tetracycline administration prevents diabetes induced osteopenia in the rat." Res. Commun. Chem. Path. Pharmacol., 68, pp. 27-40.

41. Kaneko H, Sasaki T, Ramamurthy N S & Golub L M. (1990) "Tetracycline administration normalizes the structure and acid phosphatase activity of osteoclasts in streptozotocin-diabetic rats." Anatom. Rec., 227, pp. 427-436.

42. Golub L M, Evans R T, McNamara T F et al. A non-antimicrobial tetracycline inhibits gingival metalloproteinases and bone loss in Porphyromonas gingivalis—induced periodontitis in rats. Ann. N.Y. Acad. Sci., 732: 96-111, 1994.

43. Blankenberg, S, Rupprecht H J, Poirier O, Bickel C, Smieja M, Hafner G, Meyer J, Cambren F, Tiret L and Athero-Gene Investigators. Plasma concentrations and genetic variation of matrix metalloproteinase-9 and prognosis of patients with cardiovascular disease. Circulation 107: 1579-1585, 2003.

44. Patel R V, Clark L N, Lebwohl M, Weinberg J M. Treatment for psoriasis and the risk of malignancy. J Am Acad Dermatol 60 (6):1001-17, 2009.

45. Bingham, S. J., Tyman, J. H. P. Improved Synthesis of Alkyl Diacetylacetates. Organic Preparations and Procedures Int. 33, 357-361 (2001).

46. Dieckmann, W., Hoppe, J., Stein, R. On the Behavior of 1,3-Dicarbonyl Compounds with Phenyl Isocyanate. Chem. Ber. 37, 4627-4638 (1904).

47. Pabon H. H. J. Synthesis of Curcumin and Related compounds. Rec. Tray. Chim. 83, 379-386, (1964)

What is claimed is:

1. A compound having the structure

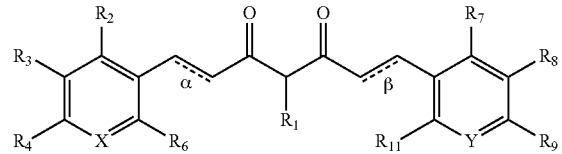

wherein bond α and β are each, independently, present or absent;

X is $CR_5$ or N; Y is $CR_{10}$ or N;

$R_1$ is —$SR_{12}$, —$SO_2R_{13}$, —$COR_{14}$, —$CSR_{14}$, —C(=$NR_{12}$)$R_{14}$, —C(=NH)$R_{14}$, —$SOR_{12}$, —$POR_{12}$, —P(=O)(O$R_{12}$) (O$R_{13}$), or —P(O$R_{12}$). (O$R_{13}$), wherein $R_{12}$ is $C_{1-10}$ alkyl, $C_{2-10}$ alkenyl, $C_{2-10}$ alkynyl, aryl, heteroaryl, or heterocyclyl;

$R_{13}$ is H, $C_{1-10}$ alkyl, $C_{2-10}$ alkenyl, $C_{2-10}$ alkynyl, aryl, heteroaryl, or heterocyclyl;

$R_{14}$ is $C_{2-10}$ alkyl, $C_{2-10}$ alkenyl, $C_{2-10}$ alkynyl, heteroaryl, heterocyclyl, methoxy, —$OR_{15}$, or —$NR_{16}R_{17}$, wherein $R_{15}$ is H, $C_{1-10}$ alkyl, $C_{2-10}$ alkenyl, $C_{2-10}$ alkynyl;

$R_{16}$ and $R_{17}$ are each, independently, H, $C_{1-10}$ alkyl, $C_{2-10}$ alkenyl, $C_{2-10}$ alkynyl, aryl, heteroaryl, or heterocyclyl;

$R_2$, $R_3$, $R_4$, $R_5$, $R_6$, $R_7$, $R_8$, $R_9$, $R_{10}$, and $R_{11}$ are each independently, H, halogen, —$NO_2$, —CN, —$NR_{28}R_{29}$, —$NHR_{28}R_{29}^+$, —$SR_{28}$, —$SO_2R_{28}$, —$OR_{28}$, —$CO_2R_{28}$, $CF_3$, $C_{1-10}$ alkyl, $C_{2-10}$ alkenyl, $C_{2-10}$ alkynyl, aryl, heteroaryl, or heterocyclyl;

wherein $R_{28}$ and $R_{29}$ are each, H, $CF_3$, $C_{1-10}$ alkyl, $C_{2-10}$ alkenyl, $C_{2-10}$ alkynyl, or —C(=O)-heterocyclyl; and wherein each occurrence of alkyl, alkenyl, or alkynyl is branched or unbranched, unsubstituted or substituted; or a salt thereof.

2. The compound of claim 1, wherein $R_1$ is —$SR_{12}$, —$SO_2R_{13}$, —$COR_{14}$, —$CSR_{14}$, —C(=$NR_{12}$)$R_{14}$, —C(=NH)$R_{14}$, or —$SOR_{12}$.

3. A compound of claim 2, wherein $R_1$ is —$COR_{14}$, —$CSR_{14}$, —C(=$NR_{12}$)$R_{14}$, or —C(=NH)$R_{14}$.

4. The compound of claim 1, having the structure

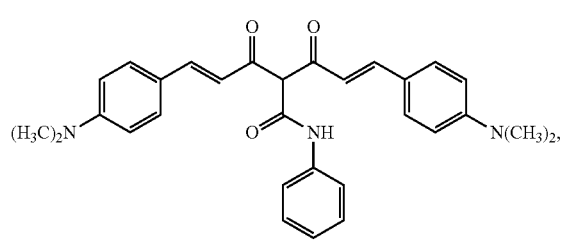

or a salt thereof.

5. The compound of claim 1 having the structure:

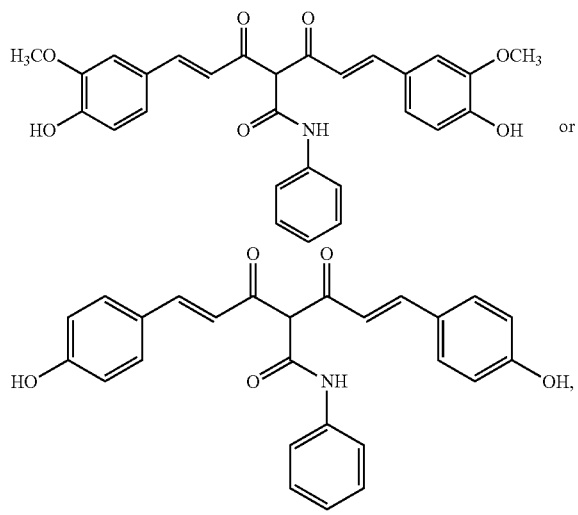

or a salt thereof.

6. The compound of claim 1 having the structure:

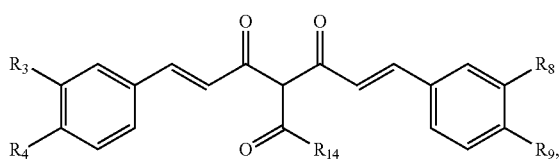

wherein $R_3$, $R_4$, $R_8$, and $R_9$ are each, independently, H, —$OCH_3$, or —OH; and $R_{14}$ is methoxy or —$N(CH_3)_2$, or a salt thereof.

7. The compound of claim 1 having the structure:

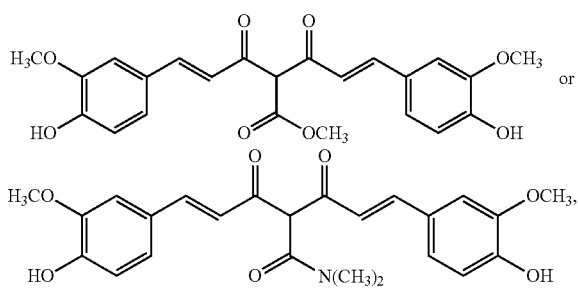

or salt thereof.

8. The compound of claim 1 having the structure:

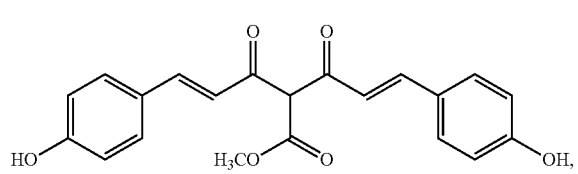

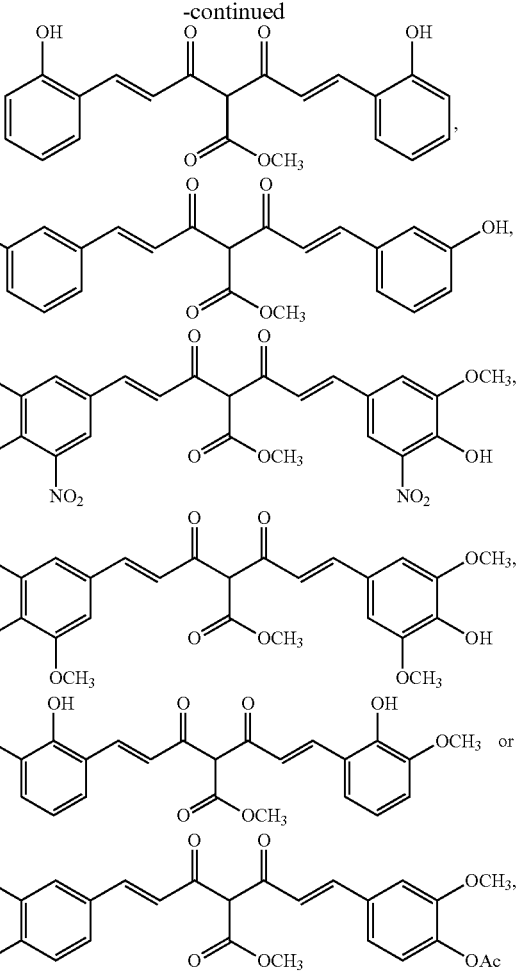

or a salt thereof.

9. The compound of claim 1 having the structure:

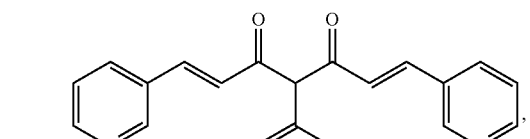

or a salt thereof.

10. The compound of claim 1 having the structure:

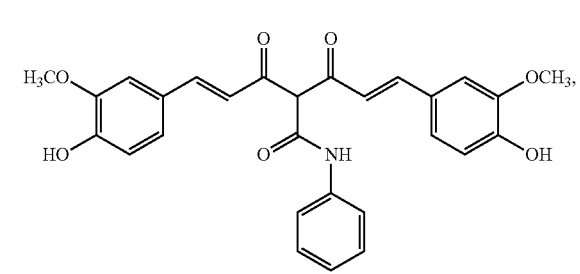 [SMILES: COc1cc(/C=C/C(=O)C(C(=O)/C=C/c2ccc(O)c(OC)c2)C(=O)Nc2ccccc2)ccc1O]

or a salt thereof.

11. The compound of claim 1 having the structure:
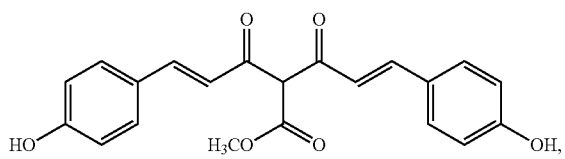
or a salt thereof.
12. The compound of claim 1 having the structure:
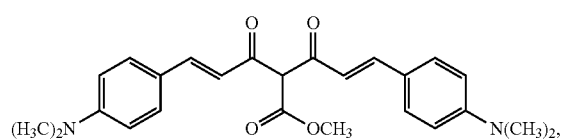
or a salt thereof.
13. A compound having the structure:
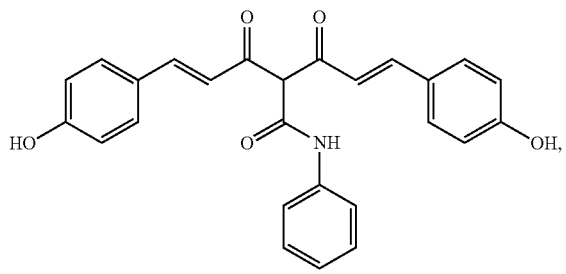 [SMILES: O=C(/C=C/c1ccc(O)cc1)C(C(=O)/C=C/c1ccc(O)cc1)C(=O)Nc1ccccc1]
or a salt thereof.
14. A compound having the structure:
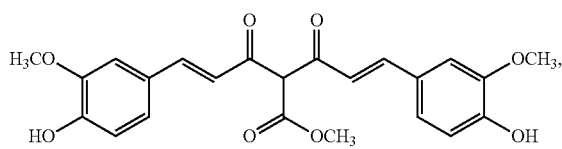 [SMILES: COC(=O)C(C(=O)/C=C/c1ccc(O)c(OC)c1)C(=O)/C=C/c1ccc(O)c(OC)c1]
or a salt thereof.
* * * * *